US008993510B2

(12) United States Patent
Gazit

(10) Patent No.: US 8,993,510 B2
(45) Date of Patent: *Mar. 31, 2015

(54) PEPTIDES AND METHODS USING SAME FOR DIAGNOSIS AND TREATMENT OF AMYLOID-ASSOCIATED DISEASE

(71) Applicant: Tel Aviv University Future Technology Development L.P., Tel-Aviv (IL)

(72) Inventor: Ehud Gazit, Ramat-HaSharon (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,414

(22) Filed: Aug. 26, 2013

(65) Prior Publication Data

US 2013/0338076 A1    Dec. 19, 2013

Related U.S. Application Data

(60) Division of application No. 12/654,461, filed on Dec. 22, 2009, which is a division of application No. 10/562,852, filed as application No. PCT/IL2004/000577 on Jun. 29, 2004, now abandoned, said application No. 10/562,852 is a continuation-in-part of application No. 10/901,243, filed on Jul. 29, 2004, now abandoned, which is a continuation-in-part of application No. PCT/IL03/00079, filed on Jan. 30, 2003, which is a continuation-in-part of application No. 10/235,852, filed on Sep. 6, 2002, now abandoned.

(60) Provisional application No. 60/483,180, filed on Jun. 30, 2003, provisional application No. 60/514,974, filed on Oct. 29, 2003, provisional application No. 60/352,578, filed on Jan. 31, 2002, provisional application No. 60/392,266, filed on Jul. 1, 2002, provisional application No. 60/436,453, filed on Dec. 27, 2002.

(51) Int. Cl.

| A61K 38/00 | (2006.01) |
|---|---|
| A61K 38/05 | (2006.01) |
| C07K 5/078 | (2006.01) |
| C07K 5/065 | (2006.01) |
| C07K 5/087 | (2006.01) |
| C07K 5/093 | (2006.01) |
| C07K 5/097 | (2006.01) |
| C07K 5/103 | (2006.01) |
| C07K 5/107 | (2006.01) |
| C07K 5/113 | (2006.01) |
| C07K 5/117 | (2006.01) |
| C07K 7/06 | (2006.01) |
| C07K 14/47 | (2006.01) |

(52) U.S. Cl.

CPC ......... *C07K 5/06156* (2013.01); *C07K 5/06078* (2013.01); *C07K 5/06165* (2013.01); *C07K 5/0812* (2013.01); *C07K 5/0819* (2013.01); *C07K 5/0823* (2013.01); *C07K 5/1008* (2013.01); *C07K 5/101* (2013.01); *C07K 5/1016* (2013.01); *C07K 5/1021* (2013.01); *C07K 5/1024* (2013.01); *C07K 7/06* (2013.01); *C07K 14/4711* (2013.01); *A61K 38/00* (2013.01)

USPC .......................................................... 514/1.1

(58) Field of Classification Search
None
See application file for complete search history.

(56) References Cited

U.S. PATENT DOCUMENTS

| 3,791,932 A | 2/1974 | Schuurs et al. |
|---|---|---|
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,626,540 A | 12/1986 | Capps et al. |
| 4,666,828 A | 5/1987 | Gusella |
| 4,683,202 A | 7/1987 | Mullis |
| 4,801,531 A | 1/1989 | Frossard |

(Continued)

FOREIGN PATENT DOCUMENTS

| AU | 2003207973 | 9/2003 |
|---|---|---|
| AU | 2004203461 | 11/2004 |
| DE | 3412445 | 10/1985 |
| DE | 10043282 | 3/2002 |
| EP | 0081122 | 6/1983 |

(Continued)

OTHER PUBLICATIONS

Official Action Dated Dec. 18, 2013 From the US Patent and Trademark Office Re. U.S. Appl. No. 13/884,989.
Communication Pursuant to Article 94(3) EPC Dated Apr. 14, 2010 From the European Patent Office Re.: Application No. 03704977.2.

(Continued)

*Primary Examiner* — Daniel E Kolker
*Assistant Examiner* — Aditi Dutt

(57) ABSTRACT

Peptides having at least 2 amino acids and no more than 15 amino acids are provided. The peptides comprise amino acid sequence X-Y or Y-X, wherein X is an aromatic amino acid and Y is any amino acid other than glycine. Also provided are pharmaceutical compositions and kits including such peptides as well as methods using same for diagnosing and treating amyloid associated diseases.

7 Claims, 34 Drawing Sheets
(9 of 34 Drawing Sheet(s) Filed in Color)

(56) References Cited

U.S. PATENT DOCUMENTS

| | | |
|---|---|---|
| 4,873,316 A | 10/1989 | Meade et al. |
| 4,879,219 A | 11/1989 | Wands et al. |
| 4,970,233 A | 11/1990 | McHugh |
| 5,011,771 A | 4/1991 | Bellet et al. |
| 5,192,659 A | 3/1993 | Simons |
| 5,272,057 A | 12/1993 | Smulson et al. |
| 5,281,521 A | 1/1994 | Trojanowski et al. |
| 5,556,744 A | 9/1996 | Weiner et al. |
| 5,593,937 A | 1/1997 | Saito et al. |
| 5,593,967 A | 1/1997 | Horwell et al. |
| 5,659,041 A | 8/1997 | Pollak et al. |
| 5,688,561 A | 11/1997 | Ichikawa et al. |
| 6,261,569 B1 | 7/2001 | Comis et al. |
| 6,303,567 B1 | 10/2001 | Findeis et al. |
| 6,359,112 B2 | 3/2002 | Kapurniotu et al. |
| 6,593,339 B1 | 7/2003 | Eek et al. |
| 6,610,478 B1 | 8/2003 | Takle et al. |
| 6,617,114 B1 | 9/2003 | Fowlkes et al. |
| 6,677,153 B2 | 1/2004 | Iversen |
| 6,689,753 B1 | 2/2004 | Soto-Jara |
| 7,732,479 B2 | 6/2010 | Gazit et al. |
| 7,781,396 B2 | 8/2010 | Gazit |
| 8,012,929 B2 | 9/2011 | Gazit |
| 2001/0007015 A1 | 7/2001 | Kapurniotu et al. |
| 2001/0012889 A1 | 8/2001 | LaFleur et al. |
| 2002/0035061 A1 | 3/2002 | Krieger et al. |
| 2003/0130484 A1 | 7/2003 | Gordon et al. |
| 2003/0225155 A1 | 12/2003 | Fernandez-Pol et al. |
| 2004/0052928 A1 | 3/2004 | Gazit |
| 2005/0020809 A1 | 1/2005 | Gazit |
| 2006/0234947 A1 | 10/2006 | Gazit |
| 2007/0021345 A1 | 1/2007 | Gazit |
| 2007/0135334 A1 | 6/2007 | Gazit |
| 2007/0138007 A1 | 6/2007 | Yemini et al. |
| 2009/0156471 A1 | 6/2009 | Gazit et al. |
| 2009/0209041 A1 | 8/2009 | Gazit |
| 2010/0022459 A1 | 1/2010 | Gazit |
| 2013/0225512 A1 | 8/2013 | Gazit et al. |

FOREIGN PATENT DOCUMENTS

| | | |
|---|---|---|
| EP | 0264166 | 4/1988 |
| EP | 0421946 | 4/1991 |
| EP | 0885904 | 12/1998 |
| FR | 1373316 | 9/1964 |
| IL | 210418 | 10/2012 |
| JP | 59-044313 | 3/1984 |
| JP | 60-040061 | 3/1985 |
| JP | 63-044895 | 2/1988 |
| JP | 02-295923 | 12/1990 |
| JP | 11-514333 | 12/1999 |
| JP | 2000-193661 | 7/2000 |
| JP | 2001-500852 | 1/2001 |
| JP | 2001-504334 | 4/2001 |
| JP | 2007-537699 | 12/2007 |
| WO | WO 80/00789 | 1/1980 |
| WO | WO 92/19253 | 11/1992 |
| WO | WO 95/08999 | 4/1995 |
| WO | WO 96/28471 | 9/1996 |
| WO | WO 96/39834 | 12/1996 |
| WO | WO 97/16191 | 5/1997 |
| WO | WO 98/08868 | 3/1998 |
| WO | WO 98/20135 | 5/1998 |
| WO | WO 99/27944 | 6/1999 |
| WO | WO 01/10457 | 2/2001 |
| WO | WO 01/21188 | 3/2001 |
| WO | WO 01/34631 | 5/2001 |
| WO | WO 01/45726 | 6/2001 |
| WO | WO 01/93836 | 12/2001 |
| WO | WO 03/063760 | 8/2003 |
| WO | WO 03/077866 | 9/2003 |
| WO | WO 03/077869 | 9/2003 |
| WO | WO 2005/000193 | 1/2005 |
| WO | WO 2006/006172 | 1/2006 |
| WO | WO 2007/043046 | 4/2007 |
| WO | WO 2009/000634 | 12/2008 |
| WO | WO 2009/095265 | 8/2009 |
| WO | WO 2012/066549 | 5/2012 |

OTHER PUBLICATIONS

Communication Pursuant to Article 94(3) EPC Dated Nov. 18, 2011 From the European Patent Office Re.: Application No. 04744917.8.
European Search Report and the European Search Opinion Dated Mar. 16, 2011 From the European Patent Office Re. Application No. 10191253.3.
Examination Report Dated Jan. 8, 2008 From the Government of India, Patent Office Re.: Application No. 1671/CHENP/2004.
Examination Report Dated Jan. 12, 2011 From the Government of India, Patent Office Re. Application No. 380/CHENP/2006.
Examination Report Dated Jun. 19, 2007 of the Government of India, Patent Office Re.: Application No. 1671/CHENP/2004.
Examiner's Report Dated Apr. 7, 2011 From the Australian Government, IP Australia Re. Application No. 2004251522.
Examiner's Report Dated Feb. 11, 2010 From the Australian Government, IP Australia Re.: Application No. 2004251522.
Examiner's Report Dated Feb. 17, 2009 From the Australian Government, IP Australia Re.: Application No. 2004203461.
Examiner's Report Dated Jun. 22, 2009 From the Australian Government, IP Australia Re.: Application No. 2004203461.
International Preliminary Report on Patentability Dated Jan. 22, 2009 From the International Bureau of WIPO Re.: Application No. PCT/IL2004/000577.
International Preliminary Report on Patentability Dated Jan. 25, 2007 From the International Bureau of WIPO Re.: Application No. PCT/IL2005/000754.
International Preliminary Report on Patentability Dated May 30, 2013 From the International Bureau of WIPO Re. Application No. PCT/IL2011/050010.
International Search Report and the Written Opinion Dated Mar. 28, 2006 From the International Searching Authority Re.: Application No. PCT/IL2005/000754.
International Search Report and the Written Opinion Dated Jan. 31, 2012 From the International Searching Authority Re. Application No. PCT/IL2011/050010.
International Search Report Dated Jul. 19, 2004 From the International Searching Authority Re.: Application No. PCT/IL03/01045.
Office Action Dated Jun. 4, 2008 From the Israeli Patent Office Re.: Application No. 163285.
Office Action Dated Nov. 5, 2009 From the Israel Patent Office Re. Application No. 172788 and Its Translation Into English.
Office Action Dated Nov. 5, 2009 From the Israel Patent Office Re.: Application No. 172788 and Its Translation Into English.
Office Action Dated Jan. 8, 2009 From the Israeli Patent Office Re.: Application No. 172788 and Its Translation Into English.
Office Action Dated Apr. 11, 2011 From the Israel Patent Office Re. Application No. 172788 and Its Translation Into English.
Official Action Dated May 2, 2008 From the US Patent and Trademark Office Re.: U.S. Appl. No. 11/656,542.
Official Action Dated Sep. 2, 2008 From the US Patent and Trademark Office Re.: U.S. Appl. No. 11/471,657.
Official Action Dated Oct. 3, 2012 From the US Patent and Trademark Office Re. U.S. Appl. No. 12/654,461.
Official Action Dated Oct. 5, 2010 From the US Patent and Trademark Office Re. U.S. Appl. No. 11/632,410.
Official Action Dated Oct. 7, 2010 From the US Patent and Trademark Office Re.: U.S. Appl. No. 12/385,471.
Official Action Dated Apr. 8, 2013 From the US Patent and Trademark Office Re. U.S. Appl. No. 11/632,410.
Official Action Dated Dec. 12, 2008 From the US Patent and Trademark Office Re.: U.S. Appl. No. 11/656,542.
Official Action Dated Jun. 14, 2010 From the US Patent and Trademark Office Re.: U.S. Appl. No. 12/458,163.
Official Action Dated May 15, 2009 From the US Patent and Trademark Office Re.: U.S. Appl. No. 11/471,657.
Official Action Dated Dec. 16, 2008 From the US Patent and Trademark Office Re.: U.S. Appl. No. 10/562,852.

(56) References Cited

OTHER PUBLICATIONS

Official Action Dated Mar. 16, 2010 From the US Patent and Trademark Office Re.: U.S. Appl. No. 12/385,471.
Official Action Dated Aug. 21, 2009 From the US Patent and Trademark Office Re.: U.S. Appl. No. 10/562,852.
Official Action Dated Feb. 23, 2006 From the US Patent and Trademark Office Re.: U.S. Appl. No. 10/235,852.
Official Action Dated Jan. 24, 2013 From the US Patent and Trademark Office Re. U.S. Appl. No. 11/632,410.
Official Action Dated Sep. 27, 2012 From the US Patent and Trademark Office Re. U.S. Appl. No. 11/632,410.
Requisition by the Examiner Dated Aug. 3, 2010 From the Canadian Intellectual Property Office Re. Application No. 2,473,987.
Requisition by the Examiner Dated May 5, 2011 From the Canadian Intellectual Property Office Re. Application No. 2,530,927.
Requisition by the Examiner Dated Jun. 11, 2012 From the Canadian Intellectual Property Office Re. Application No. 2,473,987.
Requisition by the Examiner Dated Jun. 25, 2013 From the Canadian Intellectual Property Office Re. Application No. 2,530,927.
Requisition by the Examiner Dated Jun. 30, 2011 From the Canadian Intellectual Property Office Re. Application No. 2,473,987.
Search Results: STN File, Registry, RN 379722-40-4 and Following Dated Dec. 31, 2001 for the Australian Patent Application No. 2004203461.
Supplementary European Search Report Dated Apr. 18, 2006 From the European Patent Office Re.: Application No. 03704977.2.
Supplementary Partial European Search Report Dated Dec. 9, 2009 From the European Patent Office Re.: Application No. 04744917.8.
Translation of Decision on Rejection Dated Jun. 5, 2012 From the State Intellectual Property Office of the People's Republic of China Re. Application No. 200480024846.3.
Translation of Notice of Reason for Rejection Dated Jun. 3, 2011 From the Japanese Patent Office Re.: Application No. 2006-518484.
Translation of Notice of Reason for Rejection Dated Mar. 9, 2010 From the Japanese Patent Office Re.: Application No. 2006-518484.
Translation of Notice of the Reason for Rejection Dated Oct. 22, 2009 From the Korean Intellectual Property Office Re.: Application No. 2004-7011868.
Translation of Office Action Dated Aug. 24, 2010 From the State Intellectual Property Office of the People's Republic of China Re. Application No. 200480024846.3.
Translation of Decision of Rejection Dated Apr. 3, 2012 From the Japanese Patent Office Re.: Application No. 2006-518484.
Translation of Reason for Rejection Dated Aug. 11, 2009 From the Japanese Patent Office Re.: Application No. 2003-563456.
Translation of the Notice of Reason of Rejection Dated Jul. 11, 2008 From the Japanese Patent Office Re.: Application No. 2003-563456.
Written Opinion Dated Jun. 15, 2006 From the International Preliminary Examining Authority Re.: Application No. PCT/IL03/00079.
Anguiano et al. "Protofibrillar Islet Amyloid Polypeptide Permeabilizes Synthetic Vesicles by a Pore-Like Mechanism That May Be Relevant to Type II Diabetes", Biochemistry, 41: 11338-11343, 2002.
Arvinte et al. "The Structure and Mechanism of Formation of Human Calcitonin Fibrils", The Journal of Biological Chemistry, 268(9): 6415-6422, 1993.
Austin et al. "Medical Progress: Calcitonin. Physiology and Pathophysiology", The New England Journal of Medicine, 304(5): 269-278, 1981.
Ausubel et al. Current Protocols in Molecular Biology, 1(Suppl.63).
Azriel et al. "Analysis of the Minimal Amyloid-Forming Fragment of the Islet Amyloid Polypeptide. An Experimental Support for the Key Role of the Phenylalanine Residue in Amyloid Formation", The Journal of Biological Chemistry, XP002555838, 276(36): 34156-34161, Sep. 7, 2001.
Balaram "De Novo Design: Backbone Conformational Constraints in Nucleating Helices and Beta-Hairpins", Journal of Peptide Research, 54: 195-199, 1999.

Balbach et al. "Supramolecular Structure in Full-Length Alzheimer's Beta-Amyloid Fibrils: Evidence for a Parallel Beta-Sheet Organization From Solid-State Nuclear Magnetic Resonance", Biophysical Journal, 83: 1205-1216, 2002.
Baltzer et al. "De Novo Design of Proteins—What Are the Rules?", Chemical Reviews, 101(10): 3153-3163, 2001.
Banerji et al. "A Lymphocyte-Specific Cellular Enhancer Is Located Downstream of the Joining Region in Immunoglobulin Heavy Chain Genes", Cell, 33: 729-740, 1983.
Bauer et al. "Interfacial Adsorption and Aggregation Associated Changes in Secondary Structure of Human Calcitonin Monitored by ATR-FTIR Spectroscopy", Biochemistry, 33: 12276-12282, 1994.
Benvenga et al. "Homology of Calcitonin With the Amyloid-Related Proteins", Journal of Endocrinological Investigation, 17: 119-122, 1994.
Berger et al. "Calcitonin-Like Immunoreactivity of Amyloid Fibrils in Medullary Thyroid Carcinomas", Virchows Archiv A Pathological Anatomy and Histopathology, 412: 543-551, 1988.
Bird et al. "Single-Chain Antigen-Binding Proteins", Science, 242(4877): 423-426, 1988.
Boerner et al. "Production of Antigen-Specific Human Monoclonal Antibodies From In Vitro-Primed Human Splenocytes", The Journal of Immunology, 147(1): 86-95, 1991.
Booth et al. "Instability, Unfolding and Aggregation of Human Lysozyme Variants Underlying Amyloid Fibrillogenesis", Nature, 385: 787-793, 1997.
Brown et al. "Human Spongiform Encephalopathy: The National Institutes of Health Series of 300 Cases of Experimentally Transmitted Disease", Annals of Neurology, 35(5): 513-529, May 1994.
Burger et al. "Incorporation of ?-Trifluoromethyl Substituted [Alpha]-Amino Acids Into C- and N-Terminal Position of Peptides and Peptide Mimetics Using Multicomponent Reactions", Tetrahedron, 54: 5915-5928, 1998.
Bursavich et al. "Designing Non-Peptide Peptidomimetics in the 21st Century: Inhibitors Targeting Comformational Ensembles", Journal of Medical Chemistry, 45(3): 541-558, 2002.
Byrne et al. "Mutiplex Gene Regulation: A Two-Tiered Approach to Transgene Regulation in Transgenic Mice", Proc. Natl. Acad. Sci. USA, 86: 5473-5477, 1989.
Calame et al. "Transcriptional Controlling Elements in the Immunoglobulin and T Cell Receptor Loci", Advances in Immunology, 43: 235-275, 1988.
Cherny et al. "The Formation of *Escherichia coli* Curli Amyloid Fibrils is Mediated by Prion-Like Peptide Repeats", Journal of Molecular Biology, 352(2): 245-252, 2005.
Chopin et al. "Analysis of Six Prophages in *Lactococcus lactis* IL1403: Different Genetic Structure of Temperate and Virulent Phage Populations", Nucleic Acids Research, 29(3): 644-651, 2001.
Choplin "Computers and the Medicinal Chemist", Comprehensive Medicinal Chemistry, 4(Chap.17.2): 33-58, 1990.
Chou et al. "Conformational Parameters for Amino Acids in Helical, Beta-Sheet, and Random Coil Regions Calculated From Proteins", Biochemistry, 13(2): 211-222, 1974.
Claessens et al. "Review Commentary: Pi-Pi Interactions in Self-Assembly", Journal of Physical Organic Chemistry, 10: 254-272, 1997.
Cole et al. "Human Monoclonal Antibodies", Molecular &. Cellular Biochemistry, 62(2): 109-120, 1984.
Cole et al. "The EBV-Hybridoma Technique and Its Application to Human Lung Cancer", Monoclonal Antibodies and Cancer Therapy, Proceedings of the Roche-UCLA Symposium, Park City, Utah, p. 77-96, 1985.
Cooper "Selective Amyloid Staining As A Function of Amyloid Composition and Structure. Histochemical Analysis of the Alkaline Congo Red. Standardized Toluidine Blue, and Iodine Methods", Laboratory Investigation, 31(3): 232-238, 1974.
Copp "Endocrine Regulation of Calcium Metabolism", Annual Reviews in Physiology, 32: 61-86, 1970.
Cote et al. "Generation of Human Monoclonal Antibodies Reactive With Cellular Antigens", Proc. Natl. Acad. Sci. USA, 80: 2026-2030, 1983.

(56) References Cited

OTHER PUBLICATIONS

Coughlan et al. "Factors Influencing the Processing and Function of the Amyloid Beta Precursor Protein—A Potential Therapeutic Target in Alzheimer's Disease?", Pharmacology and Therapeutics, 86: 111-144, 2000.
Damas et al. "Review: TTR Amyloidosis—Structural Features Leading to Protein Aggregation and Their Implications on Therapeutic Strategies", Journal of Structural Biology, 130: 290-299, 2000.
Edlund et al. "Cell-Specific Expression of the Rat Insuline Gene: Evidence for Role of Two Distinct 5' Flanking Elements", Science, 230(4278): 912-916, 1985.
Ferrannini "Insulin Resistance Versus Insulin Deficiency in Non-Insulin-Dependent Diabetes Mellitus: Problems and Prospects", Endocrine Reviews, 19(4): 477-490, 1998.
Findeis "Approaches to Discovery and Characterization of Inhibitors of Amyloid Beta-Peptide Polymerization", Biochimica et Biophysica Acta, 1502: 76-84, 2000.
Findeis et al. "Modified-Peptide Inhibitors of Amyloid B-Peptide Polymerization", Biochemistry, 38: 6791-6800, 1999.
Fingl et al. "Inroduction: General Principles", The Pharmacological Basis of Therapeutics, 5th Ed., Sec.I(Chap.1): 1-53, 1975.
Fishwild et al. "High-Avidity Hum IgGK Monoclonal Antibodies From a Novel Strain of Minilocus Transgenic Mice", Nature Biotechnology, 14: 845-851, 1996.
Forloni et al. "Anti-Amyloidogenic Activity of Tetracyclines: Studies in Vitro", FEBS Letters, 487(3): 404-407, 2001. Figs. 1,3.
Freshney "Animal Cell Culture—A Practical Approach", IRL Press.
Friedman "Chemistry, Nutrition, and Microbiology of D-Amino Acids", Journal of Agriculture and Food Chemistry, 47(9): 3457-3479, 1999.
Frydman-Marom et al. "Cognitive-Performance Recovery of Alzheimer's Disease Model Mice by Modulation of Early Soluble Amyloidal Assemblies", Angewnadte Chemie, International Edition, XP002601658, 48(11): 1981-1986, Jan. 1, 2009. p. 1985, col. 1, Line 4-p. 1986, col. 1, Line 4, Fig.1.
Gait "Oligonucleotide Synthesis—A Practical Approach", IRL Press.
Gajdusek "Unconventional Viruses and the Origin and Disappearance of Kuru", Science, 197(4307): 943-960, 1977.
Garofalo et al. "A Series of C-Terminal Amino Alcohol Dipeptide ABeta Inhibitors", Bioorganic & Medicinal Chemistry Letters, 12(21): 3051-3053, 2002.
Gazit "A Possible Role for 'Phi'-Stacking in the Self-Assembly of Amyloid Fibrils", The FASEB Journal, 16: 77-83, 2002.
Gazit "Global Analysis of Tandem Aromatic Optapeptide Repeats: The Significance of the Aroma-Glycine Motif", Bioinformatics Discovery Note, 18(6): 880-883, 2002.
Gazit "The 'Correctly Folded' State of Proteins: Is it a Metastable State?", Angewandte Chemie, International Edition, 41(2): 257-259, 2002.
Gillard et al. "Controlling Self-Assembly", Chemical European Journal, 3(12): 1933-1940, 1997.
Gillmore et al. "Amyloidosis A Review of Recent Diagnostic and Therapeutic Developments", British Journal of Haematology, 99: 245-256, 1997.
Glenner "Amyloid Deposits and Amyloidosis. The Beta-Fibrilloses (First of Two Parts)", The New England Journal of Medicine, 302(23): 1283-1292, 1980.
Gorman et al. "Alzheimer Beta-Amyloid Peptides, Structures of Amyloid Fibrils and Alternate Aggregation Products", Biopolymers, 60: 381-394, 2001. Claims 1-16, 22-26, 70-80, 91-100.
Gratcau "Le Curli du *coli*: Une Variete Physiologique d'Amilose [*coli*'s Curli or How Amyloid Can be Physiological]", Medecine Sciences, 18(6-7): p. 664, 2002.
Haeggqvist et al. "Medin: An Integral Fragment of Aortic Smooth Muscle Cell-Produced Lactadherin Forms the Most Common Human Amyloid", Proc. Natl. Acad. Sci. USA, 96: 8669-8674, 1999.
Han et al. "Technetium Complexes for the Quantitation of Brain Amyloid", Journal of the American Chemical Society, 118: 4506-4507, 1996.

Harlow et al. "Antibodies: A Laboratory Manual", Cold Spring Harbor Laboratory, p. III-IX, 1988.
Harrison et al. "Amyloid Peptides and Proteins in Review", Reviews in Physiology, Biochemistry and Pharmacology, 159: 1-77, 2007.
Hayden et al. "'A' Is for Amylin and Amyloid in Type 2 Diabetes Mellitus", JOP Journal of the Pancreas (Online), 2(4): 124-139, 2001.
Hoeppener et al. "Islet Amyloid and Type 2 Diabetes Mellitus", The New England Journal of Medicine, 343(6): 411-419, 2000.
Hoeppener et al. "The Complete Islet Amyloid Polypeptide Precursor Is Encoded by Two Exons", Biochemical & Biophysical Research Communications, 189: 1569-1577, 1993. Database, Accession No. S04016, 1993. Claims 1-16, 22-26.
Hoogenboom et al. "By-Passing Immunisation. Human Antibodies From Synthetic Repertoires of Germline VH Gene Segments Rearranged In Vitro", Journal of Molecular Biology, 227: 381-388, 1992.
Inbar et al. "Localization of Antibody-Combining Sites Within the Variable Portions of Heavy and Light Chains", Proc. Natl. Acad. Sci. USA, 69(9): 2659-2662, 1972.
Inglot "Comparison of the Antiviral Activity In Vitro of Some Non-Steroidal Anti-Inflammatory Drugs", Journal of General Virology, 4(2): 203-214, 1969.
Inouye et al "Synthesis and Biological Properties of the 10-Substituted Analogues of ACTH-(1-18)-NH2", Shionogi Research Laboratory, Fukushima-Ku, Osaka, p. 177-182, 1978.
Jelokhani-Niaraki et al "Changes in Conformation and Antimicrobial Properties Caused by Replacement of D-Amino Acids With Alpha-Aminoisobutyric Acid in the Gramicidin Backbbone: Synthesis and Circular Dichroic Studies", Journal of the Chemical Society Perkin Transactions, 2: 1 187-1193, 1992.
Johnson et al. "Islet Amyloid, Islet-Amiloid Polypeptide, and Diabetes Mellitus", The New England Journal of Medicine, 321(8): 513-518, 1989.
Jones et al. "Replacing the Complementarity-Determining Regions in a Human Antibody With Those From a Mouse", Nature, 321: 522-525, 1986.
Kahn et al. "Islet Amyloid: A Long-Recognized But Underappreciated Pathological Feature of Type 2 Diabetes", Diabetes, 48: 241-253, 1999.
Kamihira et al. "Conformational Transitions and Fibrillation Mechanism of Human Calcitonin as Studied by High-Resolution Solid-State 13C NMR [in Process Citation]", Protein Science, 9: 867-877, 2000.
Kanaori et al. "Study of Human Calcitonin Fibrillation by Proton Nuclear Magnetic Resonance Spectroscopy", Biochemistry, 34: 12138-12143, 1995.
Kapurniotu et al. "Structure-Based Design and Study of Non-Amyloidogenic, Double N-Methylated IAPP Amyloid Core Sequences as Inhibitors of IAPP Amyloid Formation and Cytotoxicity", Journal of Molecular Biology, 315: 339-350, 2002.
Kapurniotu et al. Database, Accession No. AAW93015, 1991.
Karle et al. "Structural Characteristics of Alpha-Helical Peptide Molecules Containing Aib Residues", Biochemistry, 29(29): 6747-6756, Jul. 24, 1990.
Kedar et al. "In Vitro Synthesis of 'Amyloid' Fibrils From Insulin, Calcitonin and Parathormone", Israel Journal of Medical Science, 12(10): 1137-1140, 1976.
Kilkarni et al. "Investigation of the Effect of Antisense Oligodeoxynucleotides to Islet Amyloid Polypeptide mRNA on Insulin Release, Content and Expression", Journal of Endocrinology, 151: 341-348, 1996.
Kohler et al. "Continuous Cultures of Fused Cells Secreting Antibody of Predefined Specifity", Nature, 256: 495-497. 1975.
Kozbor et al. "Specific Immunoglobulin Production and Enhanced Tumorigenicity Following Ascites Growth of Human Hybridomas", Journal of Immunological Methods, 81: 31-42, 1985.
Kuner et al. "Controlling Polmerization of Beta-Amyloid and Prion-Derived Peptides With Synthetic Smal Molecule Ligands", Journal of Biological Chemistry, 275(3): 1673-1678, 2000.
Kyle et al. "A Simple Method for Displaying the Hydropathic Character of a Protein", Journal of Molecular Biology, 157: 105-132, 1982.

(56) References Cited

OTHER PUBLICATIONS

Lansbury "Following Nature's Anti-Amyloid Strategy", Nature Biotechnology, 19(2): 112-113, 2001. p. 112, Left-Hand col., Paragraph 1-Middle col., Paragraph 1.

Larrick et al. "PCR Amplification of Antibody Genes", Methods: A Companion to Methods in Enzymology, 2(2): 106-110, 1991.

Lonberg et al. "Antigen-Specific Human Antibodies From Mice Comprising Four Distinct Genetic Modifications", Nature, 368(6474): 856-859, 1994.

Lonberg et al. "Human Antibodies From Transgenic Mice", International Review of Immunology, 13: 65-93, 1995.

Lowe et al. "Structure-Function Relationships for Inhibitors of Beta-Amyloid Toxicity Containing the Recognition Sequence KLVFF", Biochemistry, 40: 7882-7889, 2001.

Lyon et al. "Self-Assembly and Gelation of Oxidized Gluthathione in Organic Solvents", Journal of the American Chemical Society, 123: 4408-4413, 2001.

Maji et al. "Fibril-Forming Model Synthetic Peptides Containing 3-Aminophenylacetic Acid", Tetrahedron, 58(43): 8695-8702, 2002.

Marks et al. "By-Passing Immunization—Human Antibodies From V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Marshak et al. "Strategies for Protein Purification and Charcterization, A Laboratory Course Manual", Cold Spring Harbor Laboratory Press, 1996.

Mason et al. "Design Strategies for Anti-Amyloid Agents", Current Opinion in Structural Biology, 13: 1-7, 2003.

Maury et al. "Creation of Amyloid Fibrils From Mutant ASN187 Gelsolin Peptides", Biochemical and Biophysical Research Communications, 183(1): 227-231, 1992.

Mazor et al. "Identification and Characterization of a Novel Molecular-Recognition and Self-Assembly Domain Within the Islet Amyloid Polypeptide", Journal of Molecular Biology, 322: 1013-1024, 2002.

McGaughey et al. "Pi-Stacking Interactions. Alive and Well in Proteins", The Journal of Biological Chemistry, 273(25): 15458-15463, Jun. 19, 1998.

McLaurin et al. "Cyclohexanehexol Inhibitors of A? Aggregation Prevent and Reverse Alzheimer Phenotype in a Mouse Model", Nature Medicine, 12(7): 801-808, Jul. 2006.

Medore et al. "Fatal Familial Insomnia, A Prion Disease With A Mutation at Codon 178 of the Prion Protein Gene", The New England Journal of Medicine, 326(7): 444-449, 1992.

Merlini et al. "Intereaction of the Anthracycline 4'-Iodo-4'-Deoxydoxorubicin With Amyloid Fibrils: Inhibition of Amyloidogenesis", Proc. Natl. Acad. Sci. USA, 92: 2959-2963, 1995.

Moriatry et al. "Effects of Sequential Proline Substitutions on Amoyloid Formation by Human Amylin20-29", Biochemistry, 38: 1811-1818, 1999.

Morrison "Success in Specification", Nature, 368(6474): 812-813, 1994.

Mosmann "Rapid Colorimetric Assay for Cellular Growth and Survival: Application to Proliferation and Cytotoxicity Assays", Journal of Immunological Methods, 65: 55-63, 1983.

Mosselman et al. "Islet Amyloid Polipeptide: Identification and Chromosomal Localization of the Human Gene", FEBS Letters, 239(2): 227-232, 1988.

Mosselman et al. "The Complete Islet Amyloid Polypeptide Precursor Is Encoded by Two Exons", FEBS Letters, 247: 154-158, 1989, Database Accession No. S04016.

Mutter "Studies on the Coupling Rates in Liquid-Phase Peptide Synthesis Using Competition Experiments", International Journal of Peptide Protein Research, 13: 274-277, 1979.

Nadin et al. "Synthesis and Gamma-Secretase Activity of APP Substrate-Based Hydroxyethylene Dipeptide Isosteres", Bioorganic & Medicinal Chemistry Letters, 13(1): 37-41, Jan. 2003.

Neuberger "Generating High-Avidity Human Mabs in Mice", Nature Biotechnology, 14: 826, 1996.

Noursadeghi et al. "Role of Scrum Amyloid P. Component in Bacterial Infection: Protection of the Host or Protection of the Pathogen", Proc. Natl. Acad. Sci. USA, PNAS, 97(26): 14584-14589, Dec. 19, 2000.

Novials et al. "Reduction of Islet Amylin Expression and Basal Secretion by Adenovirus-Mediated Delivery of Amylin Antisense cDNA", Pancreas, 17(2): 182-186, 1998.

Offen et al. "A Low Molecular Weight Copper Chelator Crosses the Blood-Brain Barrier and Attenuates Experimental Autoimmune Encephalomyelitis", Journal of Neurochemistry, 89: 1241-1251, 2004.

Orlandi et al. "Cloning Immunoglobulin Variable Domains for Expression by the Polymerase Chain Reaction", Proc. Natl. Acad. Sci. USA, 86: 3833-3837, 1989.

Pack et al. "Improved Bivalent Miniantibodies, With Identical Avidity as Whole Anitbodies, Produced by High Cell Density Fermentation of *Escherichia coli*", Bio/Technology, 11: 1271-1277, 1993.

Pavia et al. "Antimicrobial Activity of Nicotine Against a Spectrum of Bacterial and Fungal Pathogens", Journal of Medical Microbiology, 49(7): 675-676, 2000.

Perbal "A Practical Guide to Molecular Cloning", Wiley-Interscience Publication.

Petkova et al. "A Structural Model for Alzheimer's Beta-Amyloid Fibrils Based on Experimental Constraints From Solid State NMR", Proc. Natl. Acad. Sci. USA, 99(26): 16742-16747, 2002.

Pettmann et al. "Morphological and Biochemical Maturation of Neurones Cultured in the Absence of Glial Cells", Nature, 281: 378-380, 1979.

Pinkert et al. "An Albumin Enhancer Located 10 Kb Upstream Functions Along With Its Promoter to Direct Efficient, Liver-Specific Expression in Transgenic Mice", Genes & Development, 1: 268-276, 1987.

Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.

Porter "The Hydrolysis of Rabbit Gamma-Globulin and Antibodies With Crystalline Papain", Biochemical Journal, 73: 119-126, 1959.

Presta "Antibody Engineering", Current Opinion in Structural Biology, 2: 593-596, 1992.

Puchtler et al. "A Review of Early Concepts of Amyloid in Context With Contemporary Chemical Literature From 1839 to 1859", The Journal of Histochemistry and Cytochemistry, 14(2): 123-134, 1966.

Reches et al. "Amyloid Fibril Formation by Pentapeptide and Tetrapeptide Fragments of Human Calcitonin", The Journal of Biological Chemistry, XP002276670, 277(38): 35475-35480, 2002.

Reches et al. "Casting Metal Nanowires Within Discrete Self-Assembled Peptide Nanotubes", Science, 300: 625-627, Apr. 2003.

Reza et al "Self-Assembling Organic Nanotubes Based on A Cyclic Peptide Architecture", Nature, 366: 324-327, 1993.

Riechmann et al. "Reshaping Human Antibodies for Therapy", Nature, 332: 323-329, 1988.

Sambrook et al. "Molecular Cloning: A Laboratory Manual", 2nd Edition, Cold Spring Harbor Laboratory,1989.

Sano "Prevention of Alzheimer's Disease: Where We Stand", Current Neurology and Neuroscience Reports, 2(5): 392-399, Oct. 2002. Abstract.

Schoetz et al. "Determination of the Cis-Trans Isomerization Barrier of Several L-Peptidyl-L-Proline Dipeptides by Dynamic Capillary Electrophoresis and Computer Simulation", Electrophoresis, 22(12): 2409-2415, Aug. 1, 2001.

Seino "S20G Mutation of the Amylin Gene Is Associated With Type II Diabetes in Japanes", Diabetologia, 44: 906-909, 2001.

Shetty et al. "Aromatic Pi-Stacking in Solution as Revealed Through the Aggregation of Phenylacetylene Macrocycles", Journal of the American Chemical Society, 118: 1019-1027, 1996.

Sigel-Causey et al. "Phylogeny of the Pelecaniformes: Molecular Systematics of A Privative Group", Avian Molecular Evolution and Systematics, academic Press, p. 159-171, NBCI GenBank, Accession No. AAB58518, 1997.

(56) References Cited

OTHER PUBLICATIONS

Sigma "Alphabetical List of Compounds: Phe-Phe, Phe-Pro, Phe-Val", Biochemicals and Reagents for Life Science Research, p. 774, 2000-2001.
Solomon et al. "Disaggregation of Alzheimer Beta-Amyloid by Site-Directed MAb", Proc. Natl. Acad. Sci. USA, 94: 4109-4112, 1997.
Soto et al. "Beta-Sheet Breaker Peptides Inhibit Fibrillogenesis in A Rat Brain Model of Amyloidosis: Implications for Alzheimer's Therapy", Nature Medicine, 4(7): 822-826, Jul. 1998.
Soto et al. "Inhibition of Alzheimer's Amyloidosis by Peptides That Prevent Beta-Sheet Conformation", Biochemical and Biophysical Research Communications, 226(3): 672-680, 1996.
Stephenson et al. "The 'Promiscuous Drug Concept' With Applications to Alzheimer's Disease", FEBS Letters, 579: 1338-1342, 2005.
Stites et al. "Tables of Content", Basic & Clinical Immunology, 8th Ed.: 12 P.
Sun et al. "Aromatic Van der Waals Clusters: Structure and Nonrigidity", Journal of Physical Chemistry, 100: 13348-13366, 1996.
Tenidis et al. "Identification of A Penta- and Hexapeptide of Islet Amyloid Polypeptide (IAPP) With Amyloidogenic and Cytotoxic Propereties", Journal of Molecular Biology, 295(4): 1055-1071, 2000.
Tjernberg et al. "Arrest of Beta-Amyloid Fibril Formation by A Pentapeptide Ligand", The Journal of Biological Chemistry, 271(15): 8545-8548, Apr. 12, 1996.
Tjernberg et al. "Controlling Amyloid Beta-Peptide Fibril Formation With Protease-Stable Ligands", The Journal of Biological Chemistry, 272(19): 12601-12605, 1997.
Toniolo et al. "Control of Peptide Conformation by the Thorpe-Ingold Effect (CAlpha-Tetrasubstitution)", Biopolymers (Peptide Science), 60(6): 396-419, 2001.
Tonkinson et al. "Antisense Oligodeoxynucleotides as Clinical Therapeutic Agents", Cancer Investigation, 14(1): 54-65, 1996.
Trivedi et al. "Second Generation 'Peptoid' CCK-B Receptor Antagonists: Identification and Development of N-(Adamantyloxycarbonyl)-Alpha-Methyl-(R)-Tryptophan Derivative (CI-1015) With An Improved Pharmacokinetic Profile", Journal of Medicinal Chemistry, XP002625505, 41: 38-45, Jan. 1, 1998. p. 44, col. 1, Lines 35-54, Compounds 25, 26.
Tsai et al. "Synthesis of AIB-Containing Peptidomimetics as Potential Inhibitors of Alzheimer's Gamma-Secretase", 218th ACS National Meeting, New Orleans, USA, Meeting Abstract, MEDI-018, 1999. Abstract.
Verhoeyen et al. "Reshaping Human Antibodies: Grafting An Antilysozyme Activity", Science, 239: 1534-1536, 1988.
Vescovi et al. "Synthesis and Functional Studies of THF-Gramicidin Hybrid Ion Channels", Organic & Biomolecular Chemistry, 1(16): 2983-2997, Aug. 21, 2003.
Vidal et al. "A Stop-Codon Mutation in the BRI Gene Associated With Familial British Dementia", Nature, 399: 776-781, 1999.
Westermark "Amyloid and Polypeptide Hormones: What is Their Interrelationship?", Amyloid: International Journal of Experimental & Clinical Investigation, 1: 47-60, 1994.
Westermark "Islet Amyloid Polypeptide: Pinpointing Amino Acid Residues Linked to Amyloid Fibril Formation", Proc. Natl. Acad. Sci. USA, 87: 5036-5040, 1990.
Whitlow et al. "Single-Chain Fv Proteins and Their Fusion Proteins", Methods: A Companion to Methods in Enzymology, 2(2): 97-105, 1991.
Wilesmith et al. "Bovine Spongiform Encephalopathy", Current Topics in Microbiology & Immunology, 172: 21-38, 1991.
Winoto et al. "A Novel, Inducible and T Cell-Specific Enhancer Located at the 3' End of the T Cell Receptor Alpha Locus", The EMBO Journal, 8(3): 729-733, 1989.
Winter et al. "Man-Made Antibodies", Nature, 349: 293-299, 1991. No.
Wolfenden et al. "Affinities of Amino Acid Side Chains for Solvent Water", Biochemistry, 20: 849-855, 1981.
Yamada et al. "Study of the Enzymatic Degradation of Endomorphin Analogs Containing Alpha,Alpha-Disubstituted Glycine", Peptide Science, 2000: 421-424, 2001.
Yang et al. "Curcumin Inhibits Formation of Amyloid Beta Oligomers and Fibrils, Binds Plaques, and Reduces Amyloid In Vivo", The Journal of Biological Chemistry, 280(7): 5892-5901, Feb. 18, 2005.
Zaidi et al. "Forty Years of Calcitonin—Where Are We Now? A Tribute to the Work of Iain Macintyre, FRS", Bone, 30(5): 655-663, 2002.
Notice of Reason for Rejection Dated Feb. 25, 2014 From the Japanese Patent Office Re. Application No. 2012-165656 and Its Translation Into English.
Gazit "Mechanistic Studies of Process of Amyolid Fibrils Formation by the Use of Peptide Fragments and Analogues: Implications for the Design of Fibrillization Inhibitors", Current Medicinal Chemistry, 9(19): 1725-1735, Oct. 2002.
European Search Report and the European Search Report Dated Mar. 19, 2014 From the European Patent Office Re. Application No. 13191182.8.
Venkatraman et al. "Design of Folded Peptides", Chemical Reviews, XP002720975, 101(10): 3131-3152, Oct. 2001. p. 3134-3135.
Notification of Office Action Dated Jun. 12, 2014 From The State Intellectual Property Office of the People's Republic of China Re. Application No. 201180055035.X and Its Translation Into English.
Official Action Dated Sep. 3, 2014 From the US Patent and Trademark Office Re. U.S. Appl. No. 13/884,989.

Fig. 2a                    Fig. 2b

```
        1                                    37
Rodent KCNTATCATQRLANFLVRSSNNLGPVLPPTNVGSNTY   SEQ ID NO: 152

Human  KCNTATCATQRLANFLVHSSNN|FGAILSS|TNVGSNTY   SEQ ID NO: 153
```

| | | |
|---|---|---|
| wt | NH2-NFGAILSS-COOH | SEQ ID NO: 1 |
| N1A | NH2-<u>A</u>FGAILSS-COOH | SEQ ID NO: 2 |
| F2A | NH2-N<u>A</u>GAILSS-COOH | SEQ ID NO: 3 |
| G3A | NH2-NF<u>A</u>AILSS-COOH | SEQ ID NO: 4 |
| I5A | NH2-NFGA<u>A</u>LSS-COOH | SEQ ID NO: 5 |
| L6A | NH2-NFGAI<u>A</u>SS-COOH | SEQ ID NO: 6 |

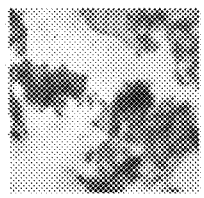 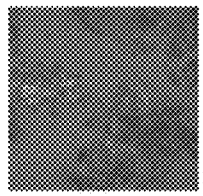 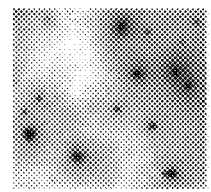 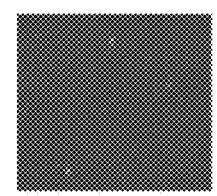
Fig. 6a  Fig. 6b  Fig. 6c  Fig. 6d
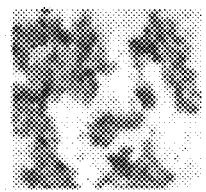 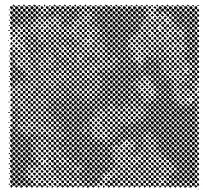 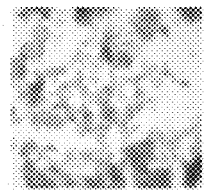 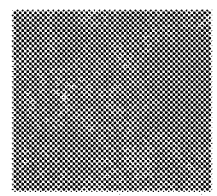
Fig. 6e  Fig. 6f  Fig. 6g  Fig. 6h
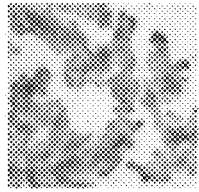 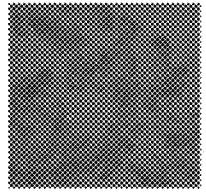 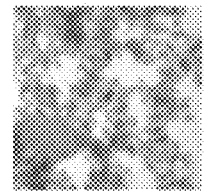 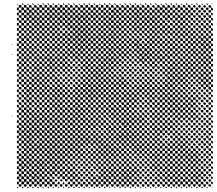
Fig. 6i  Fig. 6j  Fig. 6k  Fig. 6l
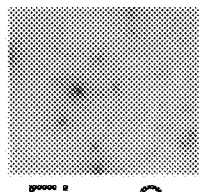 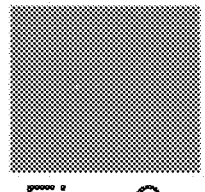
Fig. 6m  Fig. 6n

|   | M | K | C | N | T | A | T | C | A | T | Q | R | L | A |
|---|---|---|---|---|---|---|---|---|---|---|---|---|---|---|
| SEQ ID NO: 164 | 1 | | | | | | | | | | | | | |
| SEQ ID NO: 165 | 2 | ATGAAATGCAACACCGCGACCTGCGCGACCCAGCGCCTGGCG |
| SEQ ID NO: 166 | 3 | ATGAAATGCAACACTGCCACATGTGCAACCCAGCGCCTGGCA |

|   | M | F | L | V | H | S | S | N | N | F | G | A | I | L |
|---|---|---|---|---|---|---|---|---|---|---|---|---|---|---|
| SEQ ID NO: 164 | 1 | | | | | | | | | | | | | |
| SEQ ID NO: 165 | 2 | AACTTTCTGGTGCATAGCAGCAACAACTTTGGCGCGATTCTG |
| SEQ ID NO: 166 | 3 | AATTTTTTAGTTCATTCCAGCAACAACTTTGGTGCCATTCTC |

|   | S | S | T | N | V | G | S | N | T | Y |
|---|---|---|---|---|---|---|---|---|---|---|
| SEQ ID NO: 164 | 1 | | | | | | | | | |
| SEQ ID NO: 165 | 2 | AGCAGCACCAACGTGGGCAGCAACACCTAT |
| SEQ ID NO: 166 | 3 | TCATCTACCAACGTGGGATCCAATACATAT |

Synthetic gene
Human cDNA

Fig. 8a

Fig. 18a          Fig. 18b
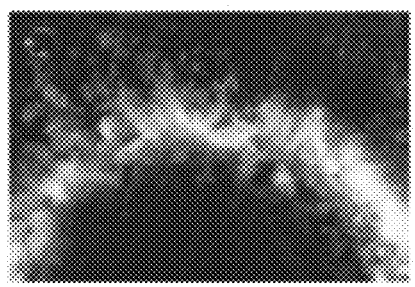
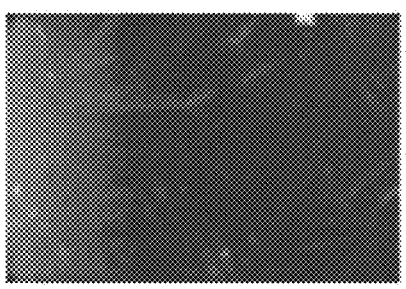
Fig. 18c          Fig. 18d
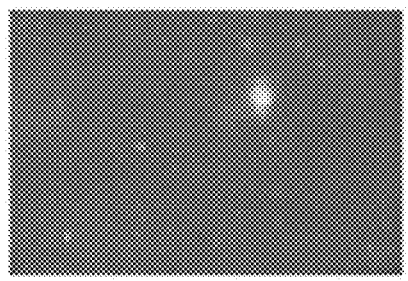
Fig. 18e          Fig. 18f

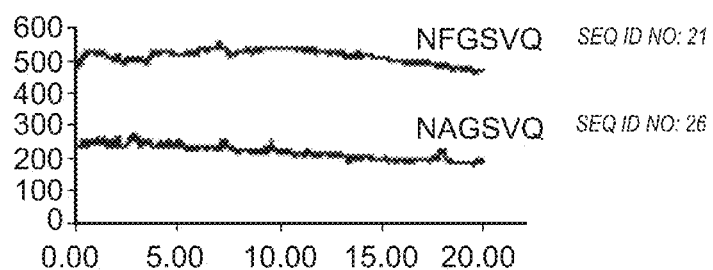
Fig. 19a
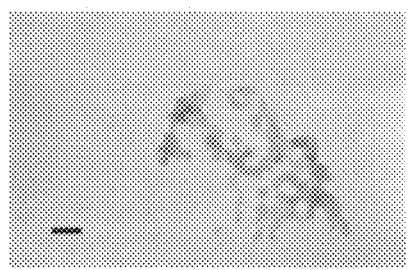 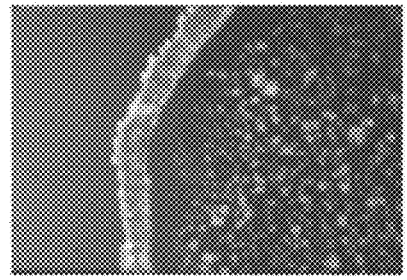
Fig. 19b        Fig. 19c
Fig. 20a    NH₂-CGNLSTCMLGTYTQDFNKFHTFPQTAIGVGAP-COOH
SEQ ID NOs: 158 and 179
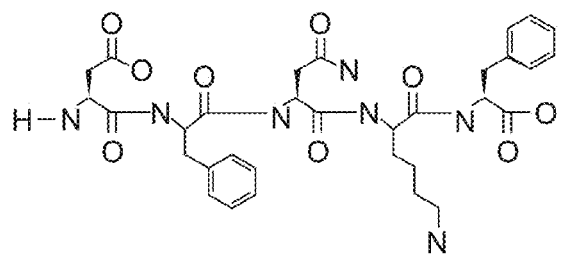
Fig. 20b

 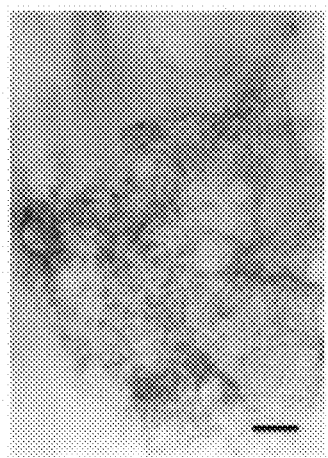
Fig. 21a    Fig. 21b
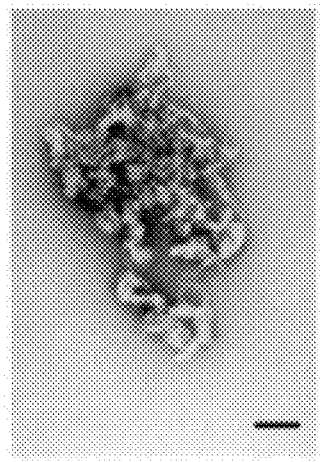 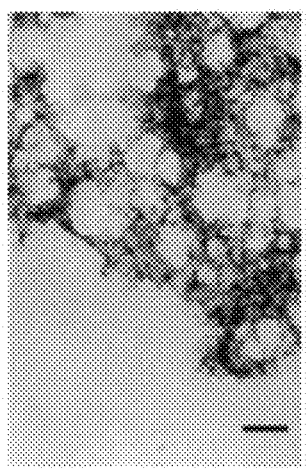
Fig. 21c    Fig. 21d

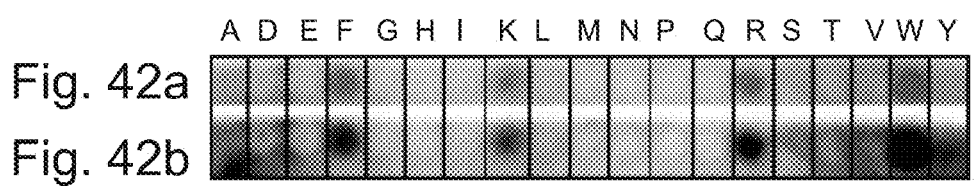
Fig. 42a
Fig. 42b
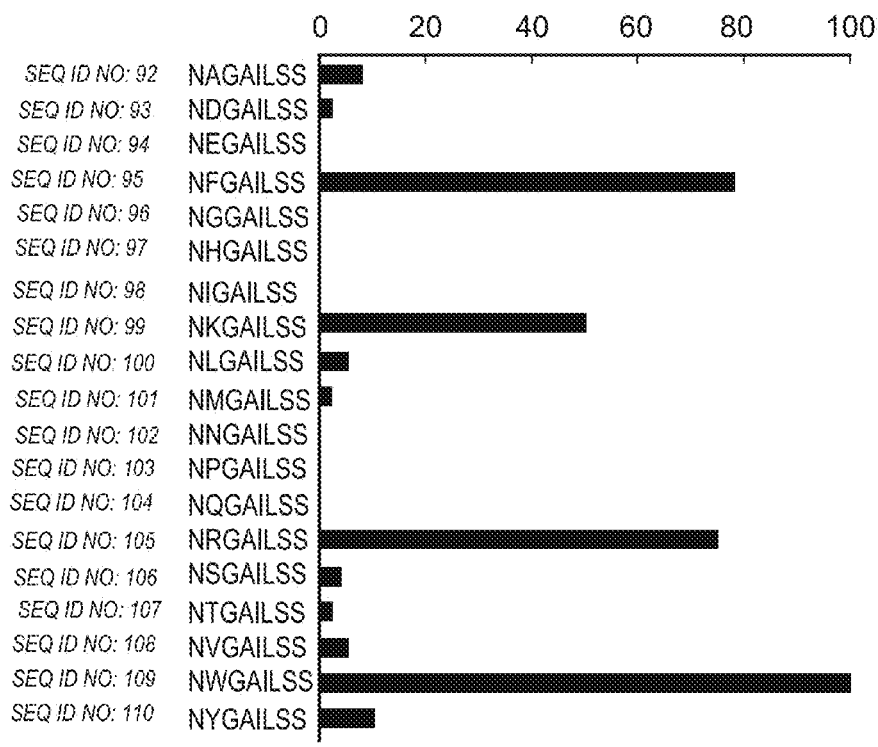
Fig. 42c

SEQUENCE LISTING

<160> NUMBER OF SEQ ID NOS: 181

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Asn Phe Gly Ala Ile Leu Ser Ser
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Ala Phe Gly Ala Ile Leu Ser Ser
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Asn Ala Gly Ala Ile Leu Ser Ser
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic peptide

<400> SEQUENCE: 4

Asn Phe Ala Ala Ile Leu Ser Ser
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Asn Phe Gly Ala Ala Leu Ser Ser
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Asn Phe Gly Ala Ile Ala Ser Ser
1               5

```
<210> SEQ ID NO 7
<211> LENGTH: 5
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Any aromatic amino acid
<220> FEATURE:
<221> NAME/KEY: misc_feature
<222> LOCATION: (2)..(2)
<223> OTHER INFORMATION: Any amino acid, but glycine
<220> FEATURE:
<221> NAME/KEY: misc_feature
<222> LOCATION: (3)..(5)
<223> OTHER INFORMATION: Any amino acid

<400> SEQUENCE: 7

Xaa Xaa Xaa Xaa Xaa
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide

<400> SEQUENCE: 8

Ala Phe Gly Ala Ile Leu
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide

<400> SEQUENCE: 9

Asn Ala Gly Ala Ile Leu
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Asn Phe Gly Ala Ala Leu
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Asn Phe Gly Ala Ile Ala
1               5

<210> SEQ ID NO 12
<211> LENGTH: 6
```

```
<212> TYPE: PRT
<213> ORGANISM: Artificial sequence
<220> FEATURE:
<223> OTHER INFORMATION: Synthetic peptide

<400> SEQUENCE: 12

Asn Phe Ala Ala Ile Leu
1               5

<210> SEQ ID NO 13
<211> LENGTH: 5
<212> TYPE: PRT
<213> ORGANISM: Artificial sequence
<220> FEATURE:
<223> OTHER INFORMATION: Synthetic peptide

<400> SEQUENCE: 13

Phe Ala Ala Ile Leu
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Asn Phe Leu Val His Ser Ser Asn Asn
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic peptide

<400> SEQUENCE: 15

Asn Phe Leu Val His Ser Ser
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic peptide

<400> SEQUENCE: 16

Phe Leu Val His Ser Ser
1               5

<210> SEQ ID NO 17
<211> LENGTH: 5
<212> TYPE: PRT
<213> ORGANISM: Artificial sequence
<220> FEATURE:
<223> OTHER INFORMATION: Synthetic peptide

<400> SEQUENCE: 17

Asn Phe Leu Val His
1               5

<210> SEQ ID NO 18
<211> LENGTH: 5
```

```
<212> TYPE: PRT
<213> ORGANISM: Artificial sequence
<220> FEATURE:
<223> OTHER INFORMATION: Synthetic peptide

<400> SEQUENCE: 18

Phe Leu Val His Ser
1               5

<210> SEQ ID NO 19
<211> LENGTH: 4
<212> TYPE: PRT
<213> ORGANISM: Artificial sequence
<220> FEATURE:
<223> OTHER INFORMATION: Synthetic peptide

<400> SEQUENCE: 19

Phe Leu Val His
1

<210> SEQ ID NO 20
<211> LENGTH: 8
<212> TYPE: PRT
<213> ORGANISM: Artificial sequence
<220> FEATURE:
<223> OTHER INFORMATION: Synthetic peptide

<400> SEQUENCE: 20

Asn Phe Gly Ser Val Gln Val Phe
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic peptide

<400> SEQUENCE: 21

Asn Phe Gly Ser Val Gln
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic peptide

<400> SEQUENCE: 22

Asn Phe Gly Ser Val
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic peptide

<400> SEQUENCE: 23

Phe Gly Ser Val Gln
1               5

<210> SEQ ID NO 24
<211> LENGTH: 4
```

```
<212> TYPE: PRT
<213> ORGANISM: Artificial sequence
<220> FEATURE:
<223> OTHER INFORMATION: Synthetic peptide

<400> SEQUENCE: 24

Gly Ser Val Gln
1

<210> SEQ ID NO 25
<211> LENGTH: 4
<212> TYPE: PRT
<213> ORGANISM: Artificial sequence
<220> FEATURE:
<223> OTHER INFORMATION: Synthetic peptide

<400> SEQUENCE: 25

Phe Gly Ser Val
1

<210> SEQ ID NO 26
<211> LENGTH: 6
<212> TYPE: PRT
<213> ORGANISM: Artificial sequence
<220> FEATURE:
<223> OTHER INFORMATION: Synthetic peptide

<400> SEQUENCE: 26

Asn Ala Gly Ser Val Gln
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic peptide

<400> SEQUENCE: 27

Asp Phe Asn Lys Phe
1               5

<210> SEQ ID NO 28
<211> LENGTH: 4
<212> TYPE: PRT
<213> ORGANISM: Artificial sequence
<220> FEATURE:
<223> OTHER INFORMATION: Synthetic peptide

<400> SEQUENCE: 28

Phe Asn Lys Phe
1

<210> SEQ ID NO 29
<211> LENGTH: 4
<212> TYPE: PRT
<213> ORGANISM: Artificial sequence
<220> FEATURE:
<223> OTHER INFORMATION: Synthetic peptide

<400> SEQUENCE: 29

Asp Phe Asn Lys
1

<210> SEQ ID NO 30
<211> LENGTH: 3
<212> TYPE: PRT
```

<213> ORGANISM: Artificial sequence
<220> FEATURE:
<223> OTHER INFORMATION: Synthetic peptide

<400> SEQUENCE: 30

Asp Phe Asn
1

<210> SEQ ID NO 31
<211> LENGTH: 5
<212> TYPE: PRT
<213> ORGANISM: Artificial sequence
<220> FEATURE:
<223> OTHER INFORMATION: Synthetic peptide

<400> SEQUENCE: 31

Asp Ala Asn Lys Phe
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic peptide

<400> SEQUENCE: 32

Leu Phe Asn Gln Thr Gly
1               5

<210> SEQ ID NO 33
<211> LENGTH: 6
<212> TYPE: PRT
<213> ORGANISM: Artificial sequence
<220> FEATURE:
<223> OTHER INFORMATION: Synthetic peptide

<400> SEQUENCE: 33

Ser Phe Phe Ser Phe Leu
1               5

<210> SEQ ID NO 34
<211> LENGTH: 5
<212> TYPE: PRT
<213> ORGANISM: Artificial sequence
<220> FEATURE:
<223> OTHER INFORMATION: Synthetic peptide

<400> SEQUENCE: 34

Phe Glu Asn Lys Phe
1               5

<210> SEQ ID NO 35
<211> LENGTH: 5
<212> TYPE: PRT
<213> ORGANISM: Artificial sequence
<220> FEATURE:
<223> OTHER INFORMATION: Synthetic peptide

<400> SEQUENCE: 35

Ser Phe Asn Asn Gly
1               5

<210> SEQ ID NO 36
<211> LENGTH: 6
<212> TYPE: PRT
<213> ORGANISM: Artificial sequence

```
<220> FEATURE:
<223> OTHER INFORMATION: Synthetic peptide

<400> SEQUENCE: 36

Leu Gln Asn Phe Thr Leu
1               5

<210> SEQ ID NO 37
<211> LENGTH: 6
<212> TYPE: PRT
<213> ORGANISM: Artificial sequence
<220> FEATURE:
<223> OTHER INFORMATION: Synthetic peptide

<400> SEQUENCE: 37

Thr Leu Ile Phe Gly Gly
1               5

<210> SEQ ID NO 38
<211> LENGTH: 6
<212> TYPE: PRT
<213> ORGANISM: Artificial sequence
<220> FEATURE:
<223> OTHER INFORMATION: Synthetic peptide

<400> SEQUENCE: 38

Arg Ala Leu Asp Phe Ala
1               5

<210> SEQ ID NO 39
<211> LENGTH: 6
<212> TYPE: PRT
<213> ORGANISM: Artificial sequence
<220> FEATURE:
<223> OTHER INFORMATION: Synthetic peptide

<400> SEQUENCE: 39

Gly Leu Val Phe Val Ser
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic peptide

<400> SEQUENCE: 40

Gly Thr Phe Gln Ile Asn
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic peptide

<400> SEQUENCE: 41

Ser Gly Ile Phe Thr Asn
1               5

<210> SEQ ID NO 42
<211> LENGTH: 5
<212> TYPE: PRT
<213> ORGANISM: Artificial sequence
<220> FEATURE:
```

<223> OTHER INFORMATION: Synthetic peptide

<400> SEQUENCE: 42

Glu Arg Gly Phe Phe
1               5

<210> SEQ ID NO 43
<211> LENGTH: 6
<212> TYPE: PRT
<213> ORGANISM: Artificial sequence
<220> FEATURE:
<223> OTHER INFORMATION: Synthetic peptide

<400> SEQUENCE: 43

Arg Asp Phe Leu Asp Arg
1               5

<210> SEQ ID NO 44
<211> LENGTH: 5
<212> TYPE: PRT
<213> ORGANISM: Artificial sequence
<220> FEATURE:
<223> OTHER INFORMATION: Synthetic peptide

<400> SEQUENCE: 44

Ser Asn Phe Leu Asn
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic peptide

<400> SEQUENCE: 45

Asn Phe Leu Val His Pro Pro
1               5

<210> SEQ ID NO 46
<211> LENGTH: 8
<212> TYPE: PRT
<213> ORGANISM: Artificial sequence
<220> FEATURE:
<223> OTHER INFORMATION: Synthetic peptide

<400> SEQUENCE: 46

Asn Phe Gly Ala Ile Leu Ser Ser
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic peptide

<400> SEQUENCE: 47

Asn Ile Gly Ala Ile Leu Ser Ser
1               5

<210> SEQ ID NO 48
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 48

Asn Leu Gly Ala Ile Leu Ser Ser
1               5

<210> SEQ ID NO 49
<211> LENGTH: 8
<212> TYPE: PRT
<213> ORGANISM: Artificial sequence
<220> FEATURE:
<223> OTHER INFORMATION: Synthetic peptide

<400> SEQUENCE: 49

Asn Val Gly Ala Ile Leu Ser Ser
1               5

<210> SEQ ID NO 50
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 50
aaatgcaaca ccgcgacctg cgcg                                          24

<210> SEQ ID NO 51
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 51
acccagcgcc tggcgaactt tctggtgcat                                    30

<210> SEQ ID NO 52
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 52
agcagcaaca actttggcgc gattctgagc                                    30

<210> SEQ ID NO 53
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 53
agcaccaacg tgggcagcaa cacctattaa tga                                33

<210> SEQ ID NO 54
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 54
tcgttgtgca taattact                                                 18
```

```
<210> SEQ ID NO 55
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 55
ccgcgctaag actcgtcgtg cttgcacccg                                      30

<210> SEQ ID NO 56
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 56
cgcttgaaag accacgtatc gtcgttgttg aaa                                  33

<210> SEQ ID NO 57
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 57
tttacgttgt ggcgctggac gcgctgggtc gcggac                               36

<210> SEQ ID NO 58
<211> LENGTH: 114
<212> TYPE: DNA
<213> ORGANISM: Artificial sequence
<220> FEATURE:
<223> OTHER INFORMATION: Modified IAPP cDNA for expression in bacteria

<400> SEQUENCE: 58
atgaaatgca acaccgcgac ctgcgcgacc cagcgcctgg cgaactttct ggtgcatagc     60
agcaacaact tggcgcgcat tctgagcagc accaacgtgg gcagcaacac ctat          114

<210> SEQ ID NO 59
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 59
gggtttccat gggccatcac catcaccatc acgaaaaatg caacaccgcg acctgc        56

<210> SEQ ID NO 60
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 60
gggtttgcgg ccgctcatta ataggtgttg ctgcc                                35

<210> SEQ ID NO 61
<211> LENGTH: 10
<212> TYPE: PRT
<213> ORGANISM: Artificial sequence
```

```
<220> FEATURE:
<223> OTHER INFORMATION: Synthetic peptide

<400> SEQUENCE: 61

Lys Cys Asn Thr Ala Thr Cys Ala Thr Gln
1               5                   10

<210> SEQ ID NO 62
<211> LENGTH: 10
<212> TYPE: PRT
<213> ORGANISM: Artificial sequence
<220> FEATURE:
<223> OTHER INFORMATION: Synthetic peptide

<400> SEQUENCE: 62

Cys Asn Thr Ala Thr Cys Ala Thr Gln Arg
1               5                   10

<210> SEQ ID NO 63
<211> LENGTH: 10
<212> TYPE: PRT
<213> ORGANISM: Artificial sequence
<220> FEATURE:
<223> OTHER INFORMATION: Synthetic peptide

<400> SEQUENCE: 63

Asn Thr Ala Thr Cys Ala Thr Gln Arg Leu
1               5                   10

<210> SEQ ID NO 64
<211> LENGTH: 10
<212> TYPE: PRT
<213> ORGANISM: Artificial sequence
<220> FEATURE:
<223> OTHER INFORMATION: Synthetic peptide

<400> SEQUENCE: 64

Thr Ala Thr Cys Ala Thr Gln Arg Leu Ala
1               5                   10

<210> SEQ ID NO 65
<211> LENGTH: 10
<212> TYPE: PRT
<213> ORGANISM: Artificial sequence
<220> FEATURE:
<223> OTHER INFORMATION: Synthetic peptide

<400> SEQUENCE: 65

Ala Thr Cys Ala Thr Gln Arg Leu Ala Asn
1               5                   10

<210> SEQ ID NO 66
<211> LENGTH: 10
<212> TYPE: PRT
<213> ORGANISM: Artificial sequence
<220> FEATURE:
<223> OTHER INFORMATION: Synthetic peptide

<400> SEQUENCE: 66

Thr Cys Ala Thr Gln Arg Leu Ala Asn Phe
1               5                   10

<210> SEQ ID NO 67
<211> LENGTH: 10
<212> TYPE: PRT
<213> ORGANISM: Artificial sequence
<220> FEATURE:
```

<223> OTHER INFORMATION: Synthetic peptide

<400> SEQUENCE: 67

Cys Ala Thr Gln Arg Leu Ala Asn Phe Leu
1               5                   10

<210> SEQ ID NO 68
<211> LENGTH: 10
<212> TYPE: PRT
<213> ORGANISM: Artificial sequence
<220> FEATURE:
<223> OTHER INFORMATION: Synthetic peptide

<400> SEQUENCE: 68

Ala Thr Gln Arg Leu Ala Asn Phe Leu Val
1               5                   10

<210> SEQ ID NO 69
<211> LENGTH: 10
<212> TYPE: PRT
<213> ORGANISM: Artificial sequence
<220> FEATURE:
<223> OTHER INFORMATION: Synthetic peptide

<400> SEQUENCE: 69

Thr Gln Arg Leu Ala Asn Phe Leu Val His
1               5                   10

<210> SEQ ID NO 70
<211> LENGTH: 10
<212> TYPE: PRT
<213> ORGANISM: Artificial sequence
<220> FEATURE:
<223> OTHER INFORMATION: Synthetic peptide

<400> SEQUENCE: 70

Gln Arg Leu Ala Asn Phe Leu Val His Ser
1               5                   10

<210> SEQ ID NO 71
<211> LENGTH: 10
<212> TYPE: PRT
<213> ORGANISM: Artificial sequence
<220> FEATURE:
<223> OTHER INFORMATION: Synthetic peptide

<400> SEQUENCE: 71

Arg Leu Ala Asn Phe Leu Val His Ser Ser
1               5                   10

<210> SEQ ID NO 72
<211> LENGTH: 10
<212> TYPE: PRT
<213> ORGANISM: Artificial sequence
<220> FEATURE:
<223> OTHER INFORMATION: Synthetic peptide

<400> SEQUENCE: 72

Leu Ala Asn Phe Leu Val His Ser Ser Asn
1               5                   10

<210> SEQ ID NO 73
<211> LENGTH: 10
<212> TYPE: PRT
<213> ORGANISM: Artificial sequence
<220> FEATURE:
<223> OTHER INFORMATION: Synthetic peptide

<400> SEQUENCE: 73

Ala Asn Phe Leu Val His Ser Ser Asn Asn
1               5                   10

<210> SEQ ID NO 74
<211> LENGTH: 10
<212> TYPE: PRT
<213> ORGANISM: Artificial sequence
<220> FEATURE:
<223> OTHER INFORMATION: Synthetic peptide

<400> SEQUENCE: 74

Asn Phe Leu Val His Ser Ser Asn Asn Phe
1               5                   10

<210> SEQ ID NO 75
<211> LENGTH: 10
<212> TYPE: PRT
<213> ORGANISM: Artificial sequence
<220> FEATURE:
<223> OTHER INFORMATION: Synthetic peptide

<400> SEQUENCE: 75

Phe Leu Val His Ser Ser Asn Asn Phe Gly
1               5                   10

<210> SEQ ID NO 76
<211> LENGTH: 10
<212> TYPE: PRT
<213> ORGANISM: Artificial sequence
<220> FEATURE:
<223> OTHER INFORMATION: Synthetic peptide

<400> SEQUENCE: 76

Leu Val His Ser Ser Asn Asn Phe Gly Ala
1               5                   10

<210> SEQ ID NO 77
<211> LENGTH: 10
<212> TYPE: PRT
<213> ORGANISM: Artificial sequence
<220> FEATURE:
<223> OTHER INFORMATION: Synthetic peptide

<400> SEQUENCE: 77

Val His Ser Ser Asn Asn Phe Gly Ala Ile
1               5                   10

<210> SEQ ID NO 78
<211> LENGTH: 10
<212> TYPE: PRT
<213> ORGANISM: Artificial sequence
<220> FEATURE:
<223> OTHER INFORMATION: Synthetic peptide

<400> SEQUENCE: 78

His Ser Ser Asn Asn Phe Gly Ala Ile Leu
1               5                   10

<210> SEQ ID NO 79
<211> LENGTH: 10
<212> TYPE: PRT
<213> ORGANISM: Artificial sequence
<220> FEATURE:
<223> OTHER INFORMATION: Synthetic peptide

```
<400> SEQUENCE: 79

Ser Ser Asn Asn Phe Gly Ala Ile Leu Ser
1               5                   10

<210> SEQ ID NO 80
<211> LENGTH: 10
<212> TYPE: PRT
<213> ORGANISM: Artificial sequence
<220> FEATURE:
<223> OTHER INFORMATION: Synthetic peptide

<400> SEQUENCE: 80

Ser Asn Asn Phe Gly Ala Ile Leu Ser Ser
1               5                   10

<210> SEQ ID NO 81
<211> LENGTH: 10
<212> TYPE: PRT
<213> ORGANISM: Artificial sequence
<220> FEATURE:
<223> OTHER INFORMATION: Synthetic peptide

<400> SEQUENCE: 81

Asn Asn Phe Gly Ala Ile Leu Ser Ser Thr
1               5                   10

<210> SEQ ID NO 82
<211> LENGTH: 10
<212> TYPE: PRT
<213> ORGANISM: Artificial sequence
<220> FEATURE:
<223> OTHER INFORMATION: Synthetic peptide

<400> SEQUENCE: 82

Asn Phe Gly Ala Ile Leu Ser Ser Thr Asn
1               5                   10

<210> SEQ ID NO 83
<211> LENGTH: 10
<212> TYPE: PRT
<213> ORGANISM: Artificial sequence
<220> FEATURE:
<223> OTHER INFORMATION: Synthetic peptide

<400> SEQUENCE: 83

Phe Gly Ala Ile Leu Ser Ser Thr Asn Val
1               5                   10

<210> SEQ ID NO 84
<211> LENGTH: 10
<212> TYPE: PRT
<213> ORGANISM: Artificial sequence
<220> FEATURE:
<223> OTHER INFORMATION: Synthetic peptide

<400> SEQUENCE: 84

Gly Ala Ile Leu Ser Ser Thr Asn Val Gly
1               5                   10

<210> SEQ ID NO 85
<211> LENGTH: 10
<212> TYPE: PRT
<213> ORGANISM: Artificial sequence
<220> FEATURE:
<223> OTHER INFORMATION: Synthetic peptide

<400> SEQUENCE: 85
```

```
Ala Ile Leu Ser Ser Thr Asn Val Gly Ser
 1               5                   10

<210> SEQ ID NO 86
<211> LENGTH: 10
<212> TYPE: PRT
<213> ORGANISM: Artificial sequence
<220> FEATURE:
<223> OTHER INFORMATION: Synthetic peptide

<400> SEQUENCE: 86

Ile Leu Ser Ser Thr Asn Val Gly Ser Asn
 1               5                   10

<210> SEQ ID NO 87
<211> LENGTH: 10
<212> TYPE: PRT
<213> ORGANISM: Artificial sequence
<220> FEATURE:
<223> OTHER INFORMATION: Synthetic peptide

<400> SEQUENCE: 87

Leu Ser Ser Thr Asn Val Gly Ser Asn Thr
 1               5                   10

<210> SEQ ID NO 88
<211> LENGTH: 10
<212> TYPE: PRT
<213> ORGANISM: Artificial sequence
<220> FEATURE:
<223> OTHER INFORMATION: Synthetic peptide

<400> SEQUENCE: 88

Ser Ser Thr Asn Val Gly Ser Asn Thr Tyr
 1               5                   10

<210> SEQ ID NO 89
<211> LENGTH: 8
<212> TYPE: PRT
<213> ORGANISM: Artificial sequence
<220> FEATURE:
<223> OTHER INFORMATION: Synthetic peptide

<400> SEQUENCE: 89

Asn Ala Gly Ala Ile Leu Ser Ser
 1               5

<210> SEQ ID NO 90
<211> LENGTH: 10
<212> TYPE: PRT
<213> ORGANISM: Artificial sequence
<220> FEATURE:
<223> OTHER INFORMATION: Peptide array consensus sequence
<220> FEATURE:
<221> NAME/KEY: misc_feature
<222> LOCATION: (4)..(4)
<223> OTHER INFORMATION: Any amino acid, but cysteine

<400> SEQUENCE: 90

Ser Asn Asn Xaa Gly Ala Ile Leu Ser Ser
 1               5                   10

<210> SEQ ID NO 91
<211> LENGTH: 8
<212> TYPE: PRT
<213> ORGANISM: Artificial sequence
<220> FEATURE:
```

<223> OTHER INFORMATION: Synthetic peptide

<400> SEQUENCE: 91

Asn Ala Gly Ala Ile Leu Ser Ser
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic peptide

<400> SEQUENCE: 92

Asn Ala Gly Ala Ile Leu Ser Ser
1               5

<210> SEQ ID NO 93
<211> LENGTH: 8
<212> TYPE: PRT
<213> ORGANISM: Artificial sequence
<220> FEATURE:
<223> OTHER INFORMATION: Synthetic peptide

<400> SEQUENCE: 93

Asn Asp Gly Ala Ile Leu Ser Ser
1               5

<210> SEQ ID NO 94
<211> LENGTH: 8
<212> TYPE: PRT
<213> ORGANISM: Artificial sequence
<220> FEATURE:
<223> OTHER INFORMATION: Synthetic peptide

<400> SEQUENCE: 94

Asn Glu Gly Ala Ile Leu Ser Ser
1               5

<210> SEQ ID NO 95
<211> LENGTH: 8
<212> TYPE: PRT
<213> ORGANISM: Artificial sequence
<220> FEATURE:
<223> OTHER INFORMATION: Synthetic peptide

<400> SEQUENCE: 95

Asn Phe Gly Ala Ile Leu Ser Ser
1               5

<210> SEQ ID NO 96
<211> LENGTH: 8
<212> TYPE: PRT
<213> ORGANISM: Artificial sequence
<220> FEATURE:
<223> OTHER INFORMATION: Synthetic peptide

<400> SEQUENCE: 96

Asn Gly Gly Ala Ile Leu Ser Ser
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

Asn His Gly Ala Ile Leu Ser Ser
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic peptide

<400> SEQUENCE: 98

Asn Ile Gly Ala Ile Leu Ser Ser
1               5

<210> SEQ ID NO 99
<211> LENGTH: 8
<212> TYPE: PRT
<213> ORGANISM: Artificial sequence
<220> FEATURE:
<223> OTHER INFORMATION: Synthetic peptide

<400> SEQUENCE: 99

Asn Lys Gly Ala Ile Leu Ser Ser
1               5

<210> SEQ ID NO 100
<211> LENGTH: 8
<212> TYPE: PRT
<213> ORGANISM: Artificial sequence
<220> FEATURE:
<223> OTHER INFORMATION: Synthetic peptide

<400> SEQUENCE: 100

Asn Leu Gly Ala Ile Leu Ser Ser
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic peptide

<400> SEQUENCE: 101

Asn Met Gly Ala Ile Leu Ser Ser
1               5

<210> SEQ ID NO 102
<211> LENGTH: 8
<212> TYPE: PRT
<213> ORGANISM: Artificial sequence
<220> FEATURE:
<223> OTHER INFORMATION: Synthetic peptide

<400> SEQUENCE: 102

Asn Asn Gly Ala Ile Leu Ser Ser
1               5

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 103

Asn Pro Gly Ala Ile Leu Ser Ser
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

Asn Gln Gly Ala Ile Leu Ser Ser
1               5

<210> SEQ ID NO 105
<211> LENGTH: 8
<212> TYPE: PRT
<213> ORGANISM: Artificial sequence
<220> FEATURE:
<223> OTHER INFORMATION: Synthetic peptide

<400> SEQUENCE: 105

Asn Arg Gly Ala Ile Leu Ser Ser
1               5

<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Asn Ser Gly Ala Ile Leu Ser Ser
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide

<400> SEQUENCE: 107

Asn Thr Gly Ala Ile Leu Ser Ser
1               5

<210> SEQ ID NO 108
<211> LENGTH: 8
<212> TYPE: PRT
<213> ORGANISM: Artificial sequence
<220> FEATURE:
<223> OTHER INFORMATION: Synthetic peptide

<400> SEQUENCE: 108

Asn Val Gly Ala Ile Leu Ser Ser
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109
```

```
Asn Trp Gly Ala Ile Leu Ser Ser
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic peptide

<400> SEQUENCE: 110

Asn Tyr Gly Ala Ile Leu Ser Ser
1               5

<210> SEQ ID NO 111
<211> LENGTH: 6
<212> TYPE: PRT
<213> ORGANISM: Artificial sequence
<220> FEATURE:
<223> OTHER INFORMATION: Synthetic peptide

<400> SEQUENCE: 111

Asn Phe Gly Ala Ile Leu
1               5

<210> SEQ ID NO 112
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 112

Phe Phe Pro
1

<210> SEQ ID NO 113
<211> LENGTH: 4
<212> TYPE: PRT
<213> ORGANISM: Artificial sequence
<220> FEATURE:
<223> OTHER INFORMATION: Synthtic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (2)..(3)
<223> OTHER INFORMATION: D-Stereoisomer
<220> FEATURE:
<221> NAME/KEY: misc_feature
<222> LOCATION: (4)..(4)
<223> OTHER INFORMATION: D and L methyl alanine

<400> SEQUENCE: 113

Xaa Phe Asn Xaa
1

<210> SEQ ID NO 114
<211> LENGTH: 4
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (4)..(4)
<223> OTHER INFORMATION: D and L methyl alanine

<400> SEQUENCE: 114

Xaa Asn Phe Xaa
1

<210> SEQ ID NO 115
<211> LENGTH: 2
<212> TYPE: PRT
<213> ORGANISM: Artificial sequence
<220> FEATURE:
<223> OTHER INFORMATION: Synthetic peptide

<400> SEQUENCE: 115

Tyr Tyr
1

<210> SEQ ID NO 116
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: amidated amino acid

<400> SEQUENCE: 116

Tyr Tyr
1

<210> SEQ ID NO 117
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine

<400> SEQUENCE: 117

Xaa Phe Phe
1

<210> SEQ ID NO 118
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: D and L methyl alanine

<400> SEQUENCE: 118

Asn Tyr Xaa
1
```

```
<210> SEQ ID NO 119
<211> LENGTH: 3
<212> TYPE: PRT
<213> ORGANISM: Artificial sequence
<220> FEATURE:
<223> OTHER INFORMATION: Synthetic peptide

<400> SEQUENCE: 119

Asn Tyr Pro
1

<210> SEQ ID NO 120
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 120

Asn Tyr Pro
1

<210> SEQ ID NO 121
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer
<220> FEATURE:
<221> NAME/KEY: misc_feature
<222> LOCATION: (2)..(2)
<223> OTHER INFORMATION: D and L methyl alanine

<400> SEQUENCE: 121

Tyr Xaa
1

<210> SEQ ID NO 122
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer

<400> SEQUENCE: 122

Pro Tyr
1

<210> SEQ ID NO 123
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer
```

```
<400> SEQUENCE: 123

Tyr Pro
1

<210> SEQ ID NO 124
<211> LENGTH: 6
<212> TYPE: PRT
<213> ORGANISM: Artificial sequence
<220> FEATURE:
<223> OTHER INFORMATION: Synthetic peptide

<400> SEQUENCE: 124

Ala Asn Phe Leu Val His
1               5

<210> SEQ ID NO 125
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (4)..(4)
<223> OTHER INFORMATION: D and L methyl alanine

<400> SEQUENCE: 125

Xaa Asn Phe Xaa Val His
1               5

<210> SEQ ID NO 126
<211> LENGTH: 5
<212> TYPE: PRT
<213> ORGANISM: Artificial sequence
<220> FEATURE:
<223> OTHER INFORMATION: Synthetic peptide

<400> SEQUENCE: 126

Ala Asn Phe Leu Val
1               5

<210> SEQ ID NO 127
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D and L methyl alanine
<220> FEATURE:
<221> NAME/KEY: misc_feature
<222> LOCATION: (4)..(4)
<223> OTHER INFORMATION: D and L methyl alanine

<400> SEQUENCE: 127

Xaa Asn Phe Xaa Val
1               5

<210> SEQ ID NO 128
<211> LENGTH: 3
<212> TYPE: PRT
<213> ORGANISM: Artificial sequence
<220> FEATURE:
```

```
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 128

Phe Phe Pro
1

<210> SEQ ID NO 129
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (2)..(3)
<223> OTHER INFORMATION: D-Stereoisomer
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 129

Xaa Phe Asn Xaa
1

<210> SEQ ID NO 130
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: D-Stereoisomer

<400> SEQUENCE: 130

Phe Asn Pro
1

<210> SEQ ID NO 131
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 131

Xaa Asn Phe Xaa
1

<210> SEQ ID NO 132
<211> LENGTH: 6
<212> TYPE: PRT
<213> ORGANISM: Artificial sequence
```

```
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 132

Gln Lys Leu Val Phe Phe
1               5

<210> SEQ ID NO 133
<211> LENGTH: 2
<212> TYPE: PRT
<213> ORGANISM: Artificial sequence
<220> FEATURE:
<223> OTHER INFORMATION: Synthetic peptide

<400> SEQUENCE: 133

Tyr Tyr
1

<210> SEQ ID NO 134
<211> LENGTH: 4
<212> TYPE: PRT
<213> ORGANISM: Artificial sequence
<220> FEATURE:
<223> OTHER INFORMATION: Synthetic peptide

<400> SEQUENCE: 134

Asn Tyr Tyr Pro
1

<210> SEQ ID NO 135
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 135

Tyr Tyr Xaa
1

<210> SEQ ID NO 136
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)

<400> SEQUENCE: 136

Xaa Tyr Tyr
1

<210> SEQ ID NO 137
<211> LENGTH: 4
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 137

Xaa Tyr Tyr Xaa
1

<210> SEQ ID NO 138
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer
<220> FEATURE:
<221> NAME/KEY: misc_feature
<222> LOCATION: (4)..(4)
<223> OTHER INFORMATION: D-Stereoisomer

<400> SEQUENCE: 138

Asn Tyr Tyr Pro
1

<210> SEQ ID NO 139
<211> LENGTH: 3
<212> TYPE: PRT
<213> ORGANISM: Artificial sequence
<220> FEATURE:
<223> OTHER INFORMATION: Synthetic peptide

<400> SEQUENCE: 139

Pro Tyr Tyr
1

<210> SEQ ID NO 140
<211> LENGTH: 3
<212> TYPE: PRT
<213> ORGANISM: Artificial sequence
<220> FEATURE:
<223> OTHER INFORMATION: Synthetic peptide

<400> SEQUENCE: 140

Tyr Tyr Pro
1

<210> SEQ ID NO 141
<211> LENGTH: 4
<212> TYPE: PRT
<213> ORGANISM: Artificial sequence
<220> FEATURE:
<223> OTHER INFORMATION: Synthetic peptide

<400> SEQUENCE: 141

Pro Tyr Tyr Pro
1
```

```
<210> SEQ ID NO 142
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer

<400> SEQUENCE: 142

Tyr Tyr
1

<210> SEQ ID NO 143
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 143

Pro Xaa
1

<210> SEQ ID NO 144
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer

<400> SEQUENCE: 144

Phe Pro
1

<210> SEQ ID NO 145
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 145

Trp Xaa
1

<210> SEQ ID NO 146
<211> LENGTH: 2
<212> TYPE: PRT
<213> ORGANISM: Artificial sequence
<220> FEATURE:
<223> OTHER INFORMATION: Synthetic peptide
<220> FEATURE:
```

```
<221> NAME/KEY: misc_feature
<222> LOCATION: (1)..(2)
<223> OTHER INFORMATION: D-Stereoisomer

<400> SEQUENCE: 146

Trp Pro
1

<210> SEQ ID NO 147
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D-Stereoisomer

<400> SEQUENCE: 147

Phe Pro
1

<210> SEQ ID NO 148
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: D-Stereoisomer

<400> SEQUENCE: 148

Pro Phe
1

<210> SEQ ID NO 149
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D-Stereoisomer
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 149

Cys Trp Xaa
1

<210> SEQ ID NO 150
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: D-Stereoisomer
<220> FEATURE:
<221> NAME/KEY: misc_feature
<222> LOCATION: (3)..(3)
<223> OTHER INFORMATION: Alpha-aminoisobutyric acid (Aib)
```

```
<400> SEQUENCE: 150

Cys Trp Xaa
1

<210> SEQ ID NO 151
<211> LENGTH: 5
<212> TYPE: PRT
<213> ORGANISM: Artificial sequence
<220> FEATURE:
<223> OTHER INFORMATION: Synthetic peptide

<400> SEQUENCE: 151

Asp Ala Asn Lys Ala
1               5

<210> SEQ ID NO 152
<211> LENGTH: 37
<212> TYPE: PRT
<213> ORGANISM: Artificial sequence
<220> FEATURE:
<223> OTHER INFORMATION: Rodent IAPP derived amino acid sequence

<400> SEQUENCE: 152

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 153
<211> LENGTH: 37
<212> TYPE: PRT
<213> ORGANISM: Artificial sequence
<220> FEATURE:
<223> OTHER INFORMATION: Human IAPP derived amino acid sequence

<400> SEQUENCE: 153

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 154
<211> LENGTH: 7
<212> TYPE: PRT
<213> ORGANISM: Artificial sequence
<220> FEATURE:
<223> OTHER INFORMATION: Synthetic peptide

<400> SEQUENCE: 154

Asn Phe Gly Ser Val Gln Phe
1               5

<210> SEQ ID NO 155
<211> LENGTH: 8
<212> TYPE: PRT
<213> ORGANISM: Artificial sequence
<220> FEATURE:
<223> OTHER INFORMATION: Synthetic peptide

<400> SEQUENCE: 155
```

```
Asn Phe Gly Ser Val Gln Phe Val
1               5

<210> SEQ ID NO 156
<211> LENGTH: 8
<212> TYPE: PRT
<213> ORGANISM: Artificial sequence
<220> FEATURE:
<223> OTHER INFORMATION: Synthetic peptide

<400> SEQUENCE: 156

Asn Phe Gly Ser Val Gln Phe Ala
1               5

<210> SEQ ID NO 157
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 157

Xaa Asn Phe Xaa Val His Ser Ser
1               5

<210> SEQ ID NO 158
<211> LENGTH: 32
<212> TYPE: PRT
<213> ORGANISM: Artificial sequence
<220> FEATURE:
<223> OTHER INFORMATION: Human Calcitonin derived amino acid sequence

<400> SEQUENCE: 158

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 159
<211> LENGTH: 4
<212> TYPE: PRT
<213> ORGANISM: Artificial sequence
<220> FEATURE:
<223> OTHER INFORMATION: Synthetic peptide

<400> SEQUENCE: 159

Gly Ala Ile Leu
1

<210> SEQ ID NO 160
<211> LENGTH: 5
<212> TYPE: PRT
<213> ORGANISM: Artificial sequence
<220> FEATURE:
<223> OTHER INFORMATION: Synthetic peptide

<400> SEQUENCE: 160

Lys Leu Val Phe Phe
1               5
```

<210> SEQ ID NO 161
<211> LENGTH: 7
<212> TYPE: PRT
<213> ORGANISM: Artificial sequence
<220> FEATURE:
<223> OTHER INFORMATION: Synthetic peptide

<400> SEQUENCE: 161

Lys Leu Val Phe Phe Ala Glu
1               5

<210> SEQ ID NO 162
<211> LENGTH: 8
<212> TYPE: PRT
<213> ORGANISM: Artificial sequence
<220> FEATURE:
<223> OTHER INFORMATION: Synthetic peptide

<400> SEQUENCE: 162

Asn Phe Gly Ser Val Gln Phe Val
1               5

<210> SEQ ID NO 163
<211> LENGTH: 7
<212> TYPE: PRT
<213> ORGANISM: Artificial sequence
<220> FEATURE:
<223> OTHER INFORMATION: Synthetic peptide

<400> SEQUENCE: 163

Gly Asn Asn Gln Gln Asn Tyr
1               5

<210> SEQ ID NO 164
<211> LENGTH: 38
<212> TYPE: PRT
<213> ORGANISM: Artificial sequence
<220> FEATURE:
<223> OTHER INFORMATION: WT hIAPP expressed by the synthetic gene

<400> SEQUENCE: 164

Met Lys Cys Asn Thr Ala Thr Cys Ala Thr Gln Arg Leu Ala Met Phe
1               5                   10                  15

Leu Val His Ser Ser Asn Asn Phe Gly Ala Ile Leu Ser Ser Thr Asn
            20                  25                  30

Val Gly Ser Asn Thr Tyr
        35

<210> SEQ ID NO 165
<211> LENGTH: 114
<212> TYPE: DNA
<213> ORGANISM: Artificial sequence
<220> FEATURE:
<223> OTHER INFORMATION: WT hIAPP coding synthetic gene

<400> SEQUENCE: 165
atgaaatgca acactgccac atgtgcaacc cagcgcctgg caaattttt agttcattcc      60 agcaacaact tggtgccat tctctcatct accaacgtgg gatccaatac atat          114

<210> SEQ ID NO 166
<211> LENGTH: 114
<212> TYPE: DNA
<213> ORGANISM: Homo sapiens
<220> FEATURE:

<221> NAME/KEY: misc_feature
<223> OTHER INFORMATION: Human IAPP coding sequence

<400> SEQUENCE: 166
atgaaatgca acaccgcgac ctgcgcgacc cagcgcctgg cgaactttct ggtgcatagc    60
agcaacaact ttggcgcgat tctgagcagc accaacgtgg gcagcaacac ctat         114

<210> SEQ ID NO 167
<211> LENGTH: 12
<212> TYPE: DNA
<213> ORGANISM: Artificial sequence
<220> FEATURE:
<223> OTHER INFORMATION: Factor Xa cleavage site coding sequence
      positioned downstream to the MBP tag in pMAL-c2X IAPP vector

<400> SEQUENCE: 167
atcgagggta gg                                                        12

<210> SEQ ID NO 168
<211> LENGTH: 30
<212> TYPE: DNA
<213> ORGANISM: Artificial sequence
<220> FEATURE:
<223> OTHER INFORMATION: NCOI restriction site followed by a 6XHis tag
      coding sequence and a V8 protease cleavage site cloned downstream
      to the MBP tag in the pMAL-c2X IAPP vector

<400> SEQUENCE: 168
accatgggcc atcaccatca ccatcacgaa                                     30

<210> SEQ ID NO 169
<211> LENGTH: 10
<212> TYPE: PRT
<213> ORGANISM: Artificial sequence
<220> FEATURE:
<223> OTHER INFORMATION: Synthetic peptide

<400> SEQUENCE: 169

Thr Gln Arg Leu Ala Asn Phe Leu Val Glu
1               5                   10

<210> SEQ ID NO 170
<211> LENGTH: 10
<212> TYPE: PRT
<213> ORGANISM: Artificial sequence
<220> FEATURE:
<223> OTHER INFORMATION: Synthetic peptide

<400> SEQUENCE: 170

Gln Arg Leu Ala Asn Phe Leu Val Glu Ser
1               5                   10

<210> SEQ ID NO 171
<211> LENGTH: 10
<212> TYPE: PRT
<213> ORGANISM: Artificial sequence
<220> FEATURE:
<223> OTHER INFORMATION: Synthetic peptide

<400> SEQUENCE: 171

Arg Leu Ala Asn Phe Leu Val Glu Ser Ser
1               5                   10

<210> SEQ ID NO 172
<211> LENGTH: 10
<212> TYPE: PRT

```
<213> ORGANISM: Artificial sequence
<220> FEATURE:
<223> OTHER INFORMATION: Synthetic peptide

<400> SEQUENCE: 172

Leu Ala Asn Phe Leu Val Glu Ser Ser Asn
1               5                   10

<210> SEQ ID NO 173
<211> LENGTH: 10
<212> TYPE: PRT
<213> ORGANISM: Artificial sequence
<220> FEATURE:
<223> OTHER INFORMATION: Synthetic peptide

<400> SEQUENCE: 173

Ala Asn Phe Leu Val Glu Ser Ser Asn Asn
1               5                   10

<210> SEQ ID NO 174
<211> LENGTH: 10
<212> TYPE: PRT
<213> ORGANISM: Artificial sequence
<220> FEATURE:
<223> OTHER INFORMATION: Synthetic peptide

<400> SEQUENCE: 174

Asn Phe Leu Val Glu Ser Ser Asn Asn Phe
1               5                   10

<210> SEQ ID NO 175
<211> LENGTH: 10
<212> TYPE: PRT
<213> ORGANISM: Artificial sequence
<220> FEATURE:
<223> OTHER INFORMATION: Synthetic peptide

<400> SEQUENCE: 175

Phe Leu Val Glu Ser Ser Asn Asn Phe Gly
1               5                   10

<210> SEQ ID NO 176
<211> LENGTH: 10
<212> TYPE: PRT
<213> ORGANISM: Artificial sequence
<220> FEATURE:
<223> OTHER INFORMATION: Synthetic peptide

<400> SEQUENCE: 176

Leu Val Glu Ser Ser Asn Asn Phe Gly Ala
1               5                   10

<210> SEQ ID NO 177
<211> LENGTH: 10
<212> TYPE: PRT
<213> ORGANISM: Artificial sequence
<220> FEATURE:
<223> OTHER INFORMATION: Synthetic peptide

<400> SEQUENCE: 177

Val Glu Ser Ser Asn Asn Phe Gly Ala Ile
1               5                   10

<210> SEQ ID NO 178
<211> LENGTH: 10
<212> TYPE: PRT
<213> ORGANISM: Artificial sequence
```

```
<220> FEATURE:
<223> OTHER INFORMATION: Synthetic peptide

<400> SEQUENCE: 178

Glu Ser Ser Asn Asn Phe Gly Ala Ile Leu
1               5                   10

<210> SEQ ID NO 179
<211> LENGTH: 32
<212> TYPE: PRT
<213> ORGANISM: Artificial sequence
<220> FEATURE:
<223> OTHER INFORMATION: Partial amino acid sequence of human Calcitonin

<400> SEQUENCE: 179

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 180
<211> LENGTH: 4
<212> TYPE: PRT
<213> ORGANISM: Artificial sequence
<220> FEATURE:
<223> OTHER INFORMATION: Factor Xa cleavage site coled downstrem to the
      MBP tag in the pMAL-c2X IAPP vector

<400> SEQUENCE: 180

Ile Glu Gly Arg
1

<210> SEQ ID NO 181
<211> LENGTH: 10
<212> TYPE: PRT
<213> ORGANISM: Artificial sequence
<220> FEATURE:
<223> OTHER INFORMATION: Amino acid sequence coded by the NCOI
      restriction site followed by a 6XHis tag and a V8 protease
      cleavage site.

<400> SEQUENCE: 181

Thr Met Gly His His His His His His Glu
1               5                   10
```

PEPTIDES AND METHODS USING SAME FOR DIAGNOSIS AND TREATMENT OF AMYLOID-ASSOCIATED DISEASE

RELATED APPLICATIONS

This application is a division of U.S. patent application Ser. No. 12/654,461 filed on Dec. 22, 2009, which is a division of U.S. patent application Ser. No. 10/562,852 filed on Apr. 19, 2006, now abandoned, which is a National Phase Application of PCT Patent Application No. PCT/IL2004/000577 filed on Jun. 29, 2004, which claims the benefit of priority from U.S. Provisional Patent Application Nos. 60/483,180 filed on Jun. 30, 2003, and 60/514,974, filed on Oct. 29, 2003.

U.S. patent application Ser. No. 10/562,852 is also a continuation-in-part (CIP) of U.S. patent application Ser. No. 10/901,243 filed on Jul. 29, 2004, now abandoned, which is continuation-in-part (CIP) of PCT Patent Application No. PCT/IL03/00079 filed on Jan. 30, 2003, which claims the benefit of priority from U.S. Provisional Patent Application Nos. 60/352,578 filed on Jan. 31, 2002, 60/392,266 filed on Jul. 1, 2002, and 60/436,453 filed on Dec. 27, 2002. PCT Patent Application No. PCT/IL03/00079 is also a continuation-in-part (CIP) of U.S. patent application Ser. No. 10/235,852 filed on Sep. 6, 2002, now abandoned.

The contents of all the above patent applications are incorporated herein by reference.

FIELD AND BACKGROUND OF THE INVENTION

The present invention relates to peptides and antibodies directed thereagainst which can be used to diagnose, prevent, and treat amyloid-associated diseases, such as Type II diabetes mellitus and Alzheimer's disease.

Amyloid material deposition (also referred to as amyloid plaque formation) is a central feature of a variety of unrelated pathological conditions including Alzheimer's disease, prion-related encephalopathies, type II diabetes mellitus, familial amyloidosis and light-chain amyloidosis.

Amyloid material is composed of a dense network of rigid, nonbranching proteinaceous fibrils of indefinite length that are about 80 to 100 Å in diameter. Amyloid fibrils contain a core structure of polypeptide chains arranged in antiparallel or parallel β-pleated sheets lying with their long axes perpendicular to the long axis of the fibril [Both et al. (1997) Nature 385:787-93; Glenner (1980) N. Eng. J. Med. 302:1283-92; Balbach et al. (2002) Biophys J. 83:1205-16].

Approximately twenty amyloid fibril proteins have been identified in-vivo and correlated with specific diseases. These proteins share little or no amino acid sequence homology, however the core structure of the amyloid fibrils is essentially the same. This common core structure of amyloid fibrils and the presence of common substances in amyloid deposits suggest that data characterizing a particular form of amyloid material may also be relevant to other forms of amyloid material and thus can be implemented in template design for the development of drugs against amyloid-associated diseases such as type II diabetes mellitus, Alzheimer's dementia or diseases and prion-related encephalopathies.

Furthermore, amyloid deposits do not appear to be inert in vivo, but rather are in a dynamic state of turnover and can even regress if the formation of fibrils is halted [Gillmore et al. (1997) Br. J. Haematol. 99:245-56].

Thus, therapies designed to inhibiting the production of amyloid polypeptides or inhibiting amyloidosis may be useful for treating amyloid associated diseases.

Inhibition of the production of amyloid polypeptides—Direct inhibition of the production of amyloid polypeptides may be accomplished, for example, through the use of antisense oligonucleotides such as against human islet amyloid polypeptide messenger RNA (mRNA). In vitro, the addition of antisense oligonucleotides or the expression of antisense complementary DNA against islet amyloid polypeptide mRNA increased the insulin mRNA and protein content of cells, demonstrating the potential effectiveness of this approach [Kulkarni et al. (1996) J. Endocrinol. 151:341-8; Novials et al. (1998) Pancreas 17:182-6]. However, no experimental results demonstrating the in vivo effectiveness of such antisense molecules have been demonstrated.

Inhibition of the formation of amyloid fibrils—Amyloid, including islet amyloid, contains potential stabilizing or protective substances, such as serum amyloid P component, apolipoprotein E, and perlecan. Blocking their binding to developing amyloid fibrils could inhibit amyloidogenesis [Kahn et al. (1999) Diabetes 48:241-53], as could treatment with antibodies specific for certain parts of an amyloidogenic protein [Solomon et al. (1997) Proc. Natl. Acad. Sci. USA 94:4109-12].

The following summarizes current attempts to engineer drugs having the capability of destabilizing amyloid structures.

Destabilizing compounds—Heparin sulfate has been identified as a component of all amyloids and has also been implicated in the earliest stages of inflammation-associated amyloid induction. Kisilevsky and co-workers (Nature Med. 1:143-148, 1995) described the use of low molecular weight anionic sulfonate or sulfate compounds that interfere with the interaction of heparin sulfate with the inflammation-associated amyloid precursor and the β peptide of Alzheimer's disease (AD). Heparin sulfate specifically influences the soluble amyloid precursor (SAA2) to adopt an increased β-sheet structure characteristic of the protein-folding pattern of amyloids. These anionic sulfonate or sulfate compounds were shown to inhibit heparin accelerated Aβ fibril formation and were able to disassemble preformed fibrils in vitro, as monitored by electron micrography. Moreover, these compounds substantially arrested murine splenic inflammation-associated amyloid progression in vivo in acute and chronic models. However, the most potent compound [i.e., poly-(vinylsulfonate)] showed acute toxicity. Similar toxicity has been observed with another compound, IDOX (Anthracycline 4'-iodo-4'-deoxy-doxorubicin), which has been observed to induce amyloid resorption in patients with immunoglobin light chain amyloidosis (AL) [Merlini et al. (1995) Proc. Natl. Acad. Sci. USA 92:2959-63].

Destabilizing antibodies—Anti-β-amyloid monoclonal antibodies have been shown to be effective in disaggregating β-amyloid plaques and preventing β-amyloid plaque formation in vitro (U.S. Pat. No. 5,688,561). However, no experimental results demonstrating the in vivo effectiveness of such antibodies have been demonstrated.

Destabilizing peptides—The finding that the addition of synthetic peptides that disrupt the β-pleated sheets ("β-sheet breakers") dissociated fibrils and prevented amyloidosis [Soto et al. (1998) Nat. Med. 4:822-6] is particularly promising from a clinical point of view. In brief, a penta-residue peptide inhibited amyloid beta-protein fibrillogenesis, disassembled preformed fibrils in vitro and prevents neuronal death induced by fibrils in cell culture. In addition, the beta-sheet breaker peptide significantly reduced amyloid beta-protein deposition in vivo and completely blocked the formation of amyloid fibrils in a rat brain model of amyloidosis.

Small molecules—The potential use of small molecules which bind the amyloid polypeptide, stabilizing the native fold of the protein has been attempted in the case of the transthyretin (TTR) protein [Peterson (1998) Proc. Natl. Acad. Sci. USA 95:12965-12960; Oza (1999) Bioorg. Med. Chem. Lett. 9:1-6]. Thus far, it has been demonstrated that molecules such as thyroxine and flufenamic acid are capable of preventing the conformation change, leading to amyloid formation. However, the use of the compounds in animal models has not been proved yet and might be compromised due to the presence in blood or proteins, other than TTR, capable of binding these ligands.

Antioxidants—Another proposed therapy has been the intake of antioxidants in order to avoid oxidative stress and maintain amyloid proteins in their reduced state (i.e., monomers and dimers). The use of sulfite was shown to lead to more stable monomers of the TTR both in vitro and in vivo [Altland (1999) Neurogenetics 2:183-188]. However, a complete characterization of the antioxidant effect is still not available and the interpretation of results concerning possible therapeutic strategies remains difficult.

While reducing the present invention to practice, the present inventors have demonstrated that contrary to the teachings of U.S. Pat. No. 6,359,112 to Kapurniotu, peptide aggregation into amyloid fibrils is governed by aromatic interactions. Such findings enable to efficiently and accurately design peptides, which can be used to diagnose and treat amyloid-associated diseases.

SUMMARY OF THE INVENTION

According to one aspect of the present invention there is provided a peptide comprising amino acid sequence X-Y or Y-X, wherein X is an aromatic amino acid and Y is any amino acid other than glycine, the peptide being at least 2 and no more than 15 amino acids in length.

According to another aspect of the present invention there is provided a peptide comprising an amino acid sequence selected from the group consisting of SEQ ID NOs. 4, 12-19, 27-45, 112-123, 125 and 127, the peptide being at least 2 and no more than 15 amino acids in length.

According to yet another aspect of the present invention there is provided a peptide comprising an amino acid sequence selected from the group consisting of SEQ ID NOs. 4, 12-19, 27-45, 112-123, 125 and 127, the peptide being at least 2 and no more than 15 amino acids in length.

According to still another aspect of the present invention there is provided a peptide selected from the group consisting of SEQ ID NOs. 4, 12-19, 27-45, 112-123, 125 and 127.

According to an additional aspect of the present invention there is provided a method of treating or preventing an amyloid-associated disease in an individual, the method comprising providing to the individual a therapeutically effective amount of a peptide including the amino acid sequence X-Y or Y-X, wherein X is an aromatic amino acid and Y is any amino acid other than glycine, the peptide being at least 2 and no more than 15 amino acids in length.

According to further features in preferred embodiments of the invention described below, the peptide is an active ingredient of a pharmaceutical composition which also includes a physiologically acceptable carrier.

According to still further features in the described preferred embodiments the peptide is expressed from a nucleic acid construct.

According to yet an additional aspect of the present invention there is provided a pharmaceutical composition for treating or preventing an amyloid-associated disease comprising as an active ingredient a peptide including the amino acid sequence X-Y or Y-X, wherein X is an aromatic amino acid and Y is any amino acid other than glycine, the peptide being at least 2 and no more than 15 amino acids in length and a pharmaceutically acceptable carrier or diluent.

According to still further features in the described preferred embodiments at least one amino acid of the at least 2 and no more than 15 amino acids of the peptide is a D stereoisomer.

According to still further features in the described preferred embodiments at least one amino acid of the at least 2 and no more than 15 amino acids of the peptide is an L stereoisomer.

According to still further features in the described preferred embodiments the peptide is two amino acids in length and Y is a β-sheet breaker amino acid.

According to still further features in the described preferred embodiments the peptide is as set forth in SEQ ID NO: 145.

According to still further features in the described preferred embodiments the peptide is 3 amino acids in length, whereas Y is an aromatic amino acid and an amino acid residue attached to the amino acid sequence X-Y or Y-X is a β-sheet breaker amino acid.

According to still further features in the described preferred embodiments the β-sheet breaker amino acid is at a C-terminus of the peptide.

According to still further features in the described preferred embodiments the peptide is at least 3 amino acids in length and includes a thiolated amino acid at an N-terminus thereof.

According to still an additional aspect of the present invention there is provided a nucleic acid construct comprising a polynucleotide segment encoding a peptide including the amino acid sequence X-Y or Y-X, wherein X is an aromatic amino acid and Y is any amino acid other than glycine, the peptide being at least 2 and no more than 15 amino acids in length.

According to still further features in the described preferred embodiments the nucleic acid construct further comprises a promoter.

According to a further aspect of the present invention there is provided an antibody or an antibody fragment comprising an antigen recognition region capable of binding a peptide including the amino acid sequence X-Y or Y-X, wherein X is an aromatic amino acid and Y is any amino acid other than glycine, the peptide being at least 2 and no more than 15 amino acids in length.

According to still further features in the described preferred embodiments Y is a polar uncharged amino acid selected from the group consisting of serine, threonine, asparagine, glutamine and natural derivatives thereof.

According to still further features in the described preferred embodiments Y is a β-sheet breaker amino acid.

According to still further features in the described preferred embodiments the β-sheet breaker amino acid is a naturally occurring amino acid.

According to still further features in the described preferred embodiments the naturally occurring amino acid is selected from the group consisting of proline, aspartic acid, glutamic acid, glycine, lysine and serine.

According to still further features in the described preferred embodiments the β-sheet breaker amino acid is a synthetic amino acid.

According to still further features in the described preferred embodiments the synthetic amino acid is a Cα-methylated amino acid.

According to still further features in the described preferred embodiments the Cα-methylated amino acid is α-aminoisobutyric acid.

According to still further features in the described preferred embodiments the peptide is a linear or cyclic peptide.

According to still further features in the described preferred embodiments the peptide is selected from the group consisting of SEQ ID NOs. 4, 12-19, 27-45, 112-123, 125 and 127.

According to still further features in the described preferred embodiments the peptide is at least 4 amino acids in length and includes at least two serine residues at a C-terminus thereof.

According to still further features in the described preferred embodiments the peptide is at least 3 amino acids in length and whereas at least one of the amino acids of the peptide other than X-Y is a polar uncharged amino acid selected from the group consisting of serine, threonine, asparagine, glutamine and natural derivatives thereof.

According to still further features in the described preferred embodiments the peptide is at least 3 amino acids in length and whereas at least one of the amino acids of the peptide other than X-Y is a is a β-sheet breaker amino acid.

According to still further features in the described preferred embodiments the β-sheet breaker amino acid is a naturally occurring amino acid.

According to still further features in the described preferred embodiments the naturally occurring amino acid is selected from the group consisting of proline, aspartic acid, glutamic acid, glycine, lysine and serine.

According to still further features in the described preferred embodiments the β-sheet breaker amino acid is a synthetic amino acid.

According to still further features in the described preferred embodiments the synthetic amino acid is a Cα-methylated amino acid.

According to still further features in the described preferred embodiments the Cα-methylated amino acid is α-aminoisobutyric acid.

According to still further features in the described preferred embodiments the β-sheet breaker amino acid is located downstream to the X-Y in the peptide.

According to still further features in the described preferred embodiments the β-sheet breaker amino acid is located upstream to the X-Y in the peptide.

According to still further features in the described preferred embodiments the peptide is at least 3 amino acids in length and whereas at least one of the amino acids of the peptide is a positively charged amino acid and at least one of the amino acid residues of the peptide is a negatively charged amino acid.

According to still further features in the described preferred embodiments the positively charged amino acid is selected from the group consisting of lysine, arginine, and natural and synthetic derivatives thereof.

According to still further features in the described preferred embodiments the negatively charged amino acid is selected from the group consisting of aspartic acid, glutamic acid and natural and synthetic derivatives thereof.

According to yet a further aspect of the present invention there is provided a pharmaceutical composition for treating or preventing an amyloid-associated disease comprising as an active ingredient an antibody or an antibody fragment having an antigen recognition region capable of binding a peptide including the amino acid sequence X-Y or Y-X, wherein X is an aromatic amino acid and Y is any amino acid other than glycine, the peptide being at least 2 and no more than 15 amino acids in length and a pharmaceutical acceptable carrier or diluent.

According to still a further aspect of the present invention there is provided a method of treating or preventing an amyloid-associated disease in an individual, the method comprising providing to the individual therapeutically effective amount of an antibody or an antibody fragment having an antigen recognition region capable of binding a peptide including the amino acid sequence X-Y or Y-X, wherein X is an aromatic amino acid and Y is any amino acid other than glycine, the peptide being at least 2 and no more than 15 amino acids in length.

According to still a further aspect of the present invention there is provided a peptide having the general Formula:

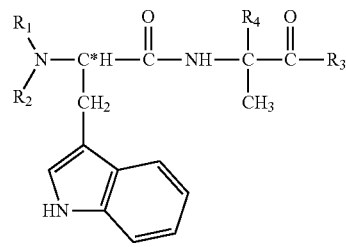

wherein:

C* is a chiral carbon having a D configuration.

$R_1$ and $R_2$ are each independently selected from the group consisting of hydrogen, alkyl, cycloalkyl, aryl, carboxy, C-thiocarb;

$R_3$ is selected from the group consisting of hydroxy, alkoxy, aryloxy, thiohydroxy, thioalkoxy, thioaryloxy, halo and amine; and $R_4$ is alkyl.

According to still a further aspect of the present invention there is provided a method of treating or preventing an amyloid-associated disease in an individual, the method comprising providing to the individual a therapeutically effective amount of a peptide having the general Formula:

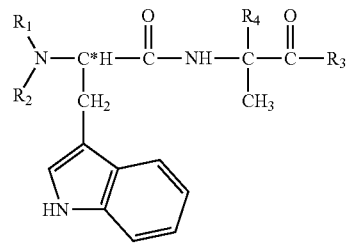

wherein:

C* is a chiral carbon having a D configuration.

$R_1$ and $R_2$ are each independently selected from the group consisting of hydrogen, alkyl, cycloalkyl, aryl, carboxy, C-thiocarb;

$R_3$ is selected from the group consisting of hydroxy, alkoxy, aryloxy, thiohydroxy, thioalkoxy, thioaryloxy, halo and amine; and $R_4$ is alkyl.

According to still further features in the described preferred embodiments $R_4$ is methyl.

According to still further features in the described preferred embodiments $R_1$ and $R_2$ are each hydrogen and $R_3$ is hydroxy.

According to still further features in the described preferred embodiments the peptide is a cyclic peptide.

The present invention successfully addresses the shortcomings of the presently known configurations by providing novel peptides, compositions and methods, which can be used to diagnose and treat amyloid associated diseases such as type II Diabetes mellitus.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2a-c are schematic illustrations of amyloid binding with the inhibitory aromatic reagents: Ro 47-1816/001 (FIG. 2a), Thioflavin T (FIG. 2b) and CR dye (FIG. 2c).

FIG. 3a is a sequence alignment of human and rodent IAPP. A block indicates a seven amino acid sub-sequence illustrating the major inconsistencies between the sequences. The "basic amyloidogenic unit" is presented by bold letters and underlined. FIG. 3b illustrates the chemical structure of the wild type IAPP peptide (SEQ ID NO: 1). FIG. 3c illustrates the primary sequences and SEQ ID NOs. of the peptides derived from the basic amyloidogenic unit.

FIGS. 6a-n are photomicrographs illustrating Congo Red binding to pre-assembled IAPP peptides. Normal field and polarized field micrographs are shown respectively for each of the following aged peptide suspensions: N1A peptide (FIGS. 6a-b), F2A peptide (FIGS. 6c-d), G3A peptide (FIGS. 6e-f), wild type peptide (FIGS. 6g-h), I5A peptide (FIGS. 6i-j) and L6A (FIGS. 6k-l). Buffer with Congo red reagent was used as a negative control visualized with and without polarized light as shown in FIGS. 6m and 6n, respectively.

FIG. 8a is a nucleic acid sequence alignment of wild type hIAPP and a corresponding sequence modified according to a bacterial codon usage. Modified bases are underlined.

FIG. 16a illustrates a short-term kinetic assay. FIG. 16b illustrates a long-term kinetic assay.

FIGS. 18a-f are photomicrographs illustrating Congo Red binding to pre-assembled Medin-derived peptides. Polarized field micrographs are shown for each of the following aged peptide suspensions: NFGSVQFA—FIG. 18a, NFGSVQ—FIG. 18b, NFGSV—FIG. 18c, FGSVQ—FIG. 18d, GSVQ—FIG. 18e and FGSV—FIG. 18f.

FIGS. 19a-c depict the effect of an alanine mutation on the amyloidogenic features of the hexapeptide amyloidogenic fragment of Medin. FIG. 19a—is a graph illustrating light absorbance at 405 nm as a function of time during fibril formation thus reflecting the aggregation kinetics of Medin-derived alanine mutant; FIG. 19b is an electron micrograph of "aged" Medin-derived alanine mutant, The scale bar represents 100 nm; FIG. 19c—is a photomicrograph illustrating Congo Red binding to pre-assembled Medin-derived peptide mutant.

FIGS. 20a-b are the amino acid sequence of human Calcitonin (FIG. 20a) and chemical structure of an amyloidogenic peptide fragment of human Calcitonin (FIG. 20b). Underlined are residues 17 and 18 which are important to the oligomerization state and hormonal activity of Calcitonin [Kazantzis (2001) Eur. J. Biochem. 269:780-791].

FIGS. 21a-d are electron micrographs of "aged" Calcitonin-derived peptides. DFNKF—FIG. 21a, DFNK—FIG. 21b, FNKF—FIG. 21c and DFN—FIG. 21d. The indicated scale bar represents 100 nm.

FIG. 24a is an electron micrograph of "aged" Calcitonin-derived alanine mutant. The scale bar represents 100 nm; FIG. 24b—is a photomicrograph illustrating Congo Red binding to pre-assembled Calcitonin-derived peptide mutant; FIG. 24c is a graph showing secondary structures in the mutant peptide as determined by Fourier transformed infrared spectroscopy.

FIGS. 42a-c illustrate the binding of IAPP—NFGAILSS to analogues of the minimal amyloidogenic sequence SNNX-GAILSS (X=any natural amino acid but cysteine). FIG. 42a shows short exposure of the bound peptide-array. FIG. 42b shows long exposure of the bound peptide-array. FIG. 42c shows quantitation of the short exposure (FIG. 42a) using densitometry and arbitrary units.

FIG. 44a—ANFLVH; FIG. 44b—ANFLV; FIG. 44c—Aib-NF-Aib-VH; and FIG. 44d—Aib-NF-Aib-V. The indicated scale bar represents 100 nm.

FIG. 45a—ANFLVH; FIG. 45b—ANFLV; FIG. 45c—Aib-NF-Aib-VH; FIG. 45d—Aib-NF-Aib-V.

FIG. 46a—wild-type peptide ANFLVH and the corresponding Aib modified peptide as designated by arrows. FIG. 46b-wild-type ANFLVH and the corresponding Aib modified peptide as designated by errows.

FIG. 49a shows the results of the first round of selection of IAPP fibrilization inhibitors. EG1=D-Phe-D-Phe-D-Pro; EG2=Aib-D-Phe-D-Asn-Aib; EG3=D-Phe-D-Asn-D-Pro; EG4=Aib-Asn-Phe-Aib; EG5=Gln-Lys-Leu-Val-Phe-Phe; EG6=Tyr-Tyr; EG7=Tyr-Tyr-NH2; EG8=Aib-Phe-Phe. FIG. 49b shows the results of the second round of selection of IAPP fibrilization inhibitors. EG13=Asn-Tyr-Aib; EG14=Asn-Tyr-Pro; EG15=D-Pro-D-Tyr-D-Asn; EG16=D-Tyr-Aib; EG17=D-Pro-D-Tyr; EG18=D-Tyr-D-Pro. FIG. 49c shows the results of the third round of selection of IAPP fibrilization inhibitors. d-F—P=D-Phe-Pro; P-d-F=Pro-D-Phe; EG19=Asn-Tyr-Tyr-Pro; EG20=Tyr-Tyr-Aib; EG21=Aib-Tyr-Tyr; EG22=Aib-Tyr-Tyr-Aib; EG23=D-Asn-Tyr-Tyr-D-Pro. FIG. 49d shows the results of the forth round of selection of IAPP fibrilization inhibitors. EG24=Pro-Tyr-Tyr; EG25=Tyr-Tyr-Pro; EG26=Pro-Tyr-Tyr-Pro; EG27=D-Tyr-D-Tyr; EG28=D-Pro-Aib; EG29=D-Phe-D-Pro; EG30=D-Trp-Aib; EG31=D-Trp-D-Pro.

FIG. 51a shows Aβ alone. FIGS. 51b-c shows two different field of Aβ incubated in the presence of the inhibitor.

DESCRIPTION OF THE PREFERRED EMBODIMENTS

Figure 1:
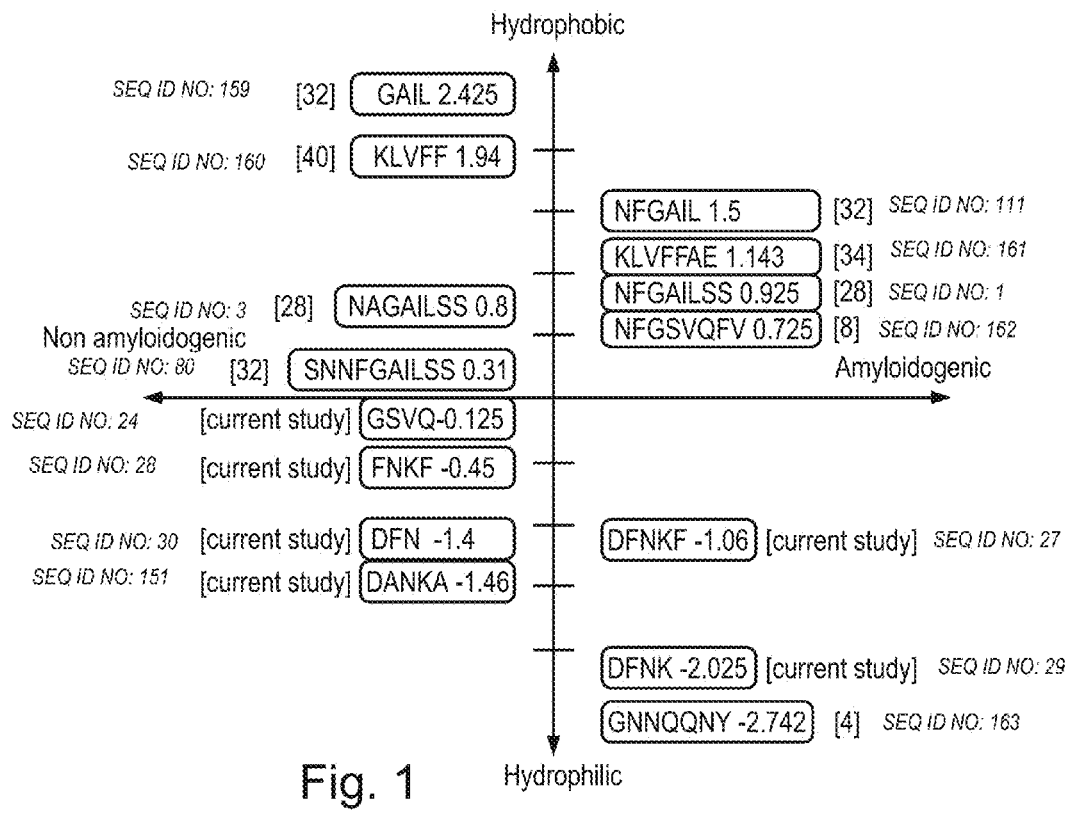
FIG. 1 is a schematic illustration depicting the self-assembly ability and hydrophobicity of a group of peptides from a number of amyloid proteins as deduced using Kyte and Dolittle scale. Note, that no correlation is observed between hydrophobicity and the amyloidogenic potential of the analyzed peptides. The only apparent indication for potential amyloid fibril formation in this group of peptide is a combination of aromatic nature and minimal length.

The present invention is of novel peptides, antibodies directed thereagainst, compositions including same and methods of utilizing each for diagnosing or treating amyloid associated diseases such as type II Diabetes mellitus.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Numerous therapeutic approaches for prevention of amyloid fibril formation or disaggreagtion of amyloid material have been described in the prior art. However, current therapeutic approaches are limited by cytotoxicity, non-specificity and delivery barriers.

While reducing the present invention to practice and while searching for a novel therapeutic modality to amyloid associated diseases, such as Type II diabetes mellitus, the present inventor has identified a sequence characteristic of amyloid forming peptides, which directs fibril formation. This finding suggests that ordered amyloidogenesis involves a specific pattern of molecular interactions rather than the previously described mechanism involving non-specific hydrophobic interactions [Petkova (2002) Proc. Natl. Acad. Sci. USA 99:16742-16747].

As is further illustrated hereinbelow and in the Examples section which follows, the present inventor attributed a pivotal role for aromatic residues in amyloid formation. The involvement of aromatic residues in the process of amyloid formation is in-line with the well-established role of π-stacking interactions in molecular recognition and self-assembly [Gillard et al (1997) Chem. Eur. J. 3: 1933-40; Claessens and Stoddart, (1997) J. Phys. Org. Chem. 10: 254-72; Shetty et al (1996) J. Am. Chem. Soc. 118: 1019-27; McGuaghey et al (1998) π-Stacking interactions: Alive and well in proteins. J. Biol. Chem. 273, 15458-15463; Sun and Bernstein (1996) J. Phys. Chem. 100: 13348-66]. π-stacking interactions are non-bonded interactions which are formed between planar aromatic rings. The steric constrains associated with the formation of those ordered stacking structures have a fundamental role in self-assembly processes that lead to the formation of supramolecular structures. Such π-stacking interactions, which are probably entropy driven, play a central role in many biological processes such as stabilization of the double-helix structure of DNA, core-packing and stabilization of the tertiary structure of proteins, host-guest interactions, and porphyrin aggregation in solution [for further review on the possible role of π-stacking interaction in the self-assembly of amyloid fibrils see Gazit (2002) FASEB J. 16:77-83].

The present inventor demonstrated the ability of short aromatic peptide sequences, as short as di-peptides (see Example 45-47), to mediate molecular recognition, enabling for the first time, to generate highly efficient diagnostic, prophylactic and therapeutic peptides which can be utilized to treat or diagnose diseases characterized by amyloid plaque formation.

Thus, according to one aspect of the present invention there is provided a peptide which includes the amino acid sequence X-Y or Y-X, wherein X is an aromatic amino acid and Y is any amino acid other than glycine. Examples of peptides that include this sequence are set forth in SEQ ID Nos. 4, 12-19, 27-45, 112-123, 125 and 127. As is shown by the results presented in Examples 36-39 of the Examples section which follows, the present inventor have uncovered that contrary to the teachings of the prior art, it is aromaticity rather than hydrophobicity which dictates amyloid self-assembly. Thus, the aromatic amino acid of the peptides of the present invention is pivotal to the formation of amyloid fibrils.

The aromatic amino acid can be any naturally occurring or synthetic aromatic residue including, but not limited to, phenylalanine, tyrosine, tryptophan, phenylglycine, or modificants, precursors or functional aromatic portions thereof. Examples of aromatic residues which can form a part of the peptides of present invention are provided in Table 2 below.

As is demonstrated by the results provided in the Examples section which follows, the present invention facilitates the design of peptides exhibiting varying degrees of self-aggregation kinetics and aggregate structure.

As used herein, the phrase "self-aggregation" refers to the capability of a peptide to form aggregates (e.g. fibrils) in an aqueous solution. The ability of a peptide to self-aggregate and the kinetics and type of such self-aggregation determines a use for the peptide in treating or diagnosing amyloid diseases.

Since aggregation kinetics and aggregate structures are largely determined by the specific residue composition and possibly the length of the peptides generated (see FIG. 1), the present invention encompasses both longer peptides (e.g., 10-50 amino acids), which include the sequences set forth in SEQ ID NOs: 4. 12-19, 27-45, 112-123, 125, 127, 128-147 or 148, or preferably shorter peptides (e.g., 2-15 amino acids, preferably at least 2, at least 3, at least 4, at least 5, at least 6, at least 8, at least-10, say 12 amino acids, preferably no more than 15 amino acids) including any of these sequences.

In order to enhance the rate of amyloid formation, the peptides of the present invention preferably include at least one polar and uncharged amino acid including but not limited to serine, threonine, asparagine, glutamine or natural or synthetic derivatives thereof (see Table 2).

According to one embodiment of this aspect of the present invention, amino acid residue Y is the polar and uncharged amino acid.

According to another embodiment of this aspect of the present invention, the peptide includes at least 3 amino acids, the X-Y/Y-X amino acid sequence described hereinabove and an additional polar and uncharged amino acid positioned either upstream (N-Terminal end) or downstream (C-Terminal end) of the X-Y/Y-X sequence.

The peptides of the present invention, can be at least 3 amino acid in length and may include at least one pair of positively charged (e.g., lysine and arginine) and negatively charged (e.g., aspartic acid and glutamic acid) amino acids (e.g., SEQ ID NOs. 27-29). Such amino acid composition may be preferable, since as shown in Examples 21 of the Examples section, it is likely that electrostatic interactions between opposing charges may direct the formation of ordered antiparallel structure.

Yet additionally, the peptide of the present invention can be 4 amino acids in length and include two serine residues at the C-terminal end of the X-Y/Y-X sequence.

Still additionally, the peptide of the present invention can be at least 3 amino acids in length and include a thiolated amino acid residue (i.e., including a sulfur ion), preferably at an N-terminal end thereof (e.g., SEQ ID NOs: 149 and 150, D-Cys-D-Trp-Aib and L-Cys-D-Trp-Aib, respectively as well as their acytelated and amidated forms). Such a peptide configuration is highly valuable since it provides reducing properties to the peptide and as such can serve both as a reducing agent and as an antioxidant both may be critical for neuroprotection (Offen et al. (2004) J. Neurochem. 89:1241-51); and as an amyloid inhibitor. Examples of thiolated amino acids include, but are not limited to, the naturally occurring amino acids cysteine and methionine and synthetic amino acids such as Tyr ($SO_3H$).

Since the present inventor has identified the sequence characteristics governing fibril formation, the teachings of the present invention also enable design of peptides which would not aggregate into fibrils and be capable of either preventing or reducing fibril formation or disrupting preformed fibrils and thus can be used as a therapeutic agents.

For example, a peptide encompassed by SEQ ID NO: 9, 10, 11, 17, 19, 25 or 30 can be utilized for therapy since as is shown in the Examples section which follows, such a peptide displays no aggregation (SEQ ID NO: 9) or slow aggregation kinetics as compared to the wild type peptide (SEQ ID NOs: 9 and 10). It is conceivable that since amyloid formation is a very slow process, these peptide sequences will completely inhibit or significantly delay amyloidosis under physiological conditions.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, Tic, naphtylalanine (NaI), phenylisoserine, threoninol, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 2-continued

| Non-conventional amino acid | Code | Non-conventional amino acid | Code |
|---|---|---|---|
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the present peptides are preferably utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

For therapeutic application, the peptides of the present invention preferably include at least one β-sheet breaker amino acid residue, which is positioned in the peptide sequence as described below. Peptides which include such β-sheet breaker amino acids retain recognition of amyloid polypeptides but prevent aggregation thereof (see Examples 40-45 of the Examples section which follows). According to one preferred embodiment of this aspect of the present invention, the β-sheet breaker amino acid is a naturally occurring amino acid such as proline (e.g., SEQ ID NOs. 45, 112, 119, 120, 122, 123, 128, 130, 134, 138, 139, 140, 141, 143, 144, 146, 147 and 148, see background section) which is characterized by a limited phi angle of about −60 to +25 rather than the typical beta sheet phi angle of about −120 to −140 degrees, thereby disrupting the beta sheet structure of the amyloid fibril. Other β-sheet breaker amino acid residues include, but are not limited to aspartic acid, glutamic acid, glycine, lysine and serine (according to Chou and Fasman (1978) Annu. Rev. Biochem. 47, 258).

According to another preferred embodiment of this aspect of the present invention, the β-sheet breaker amino acid residue is a synthetic amino acid such as a Cα-methylated amino acid, which conformational constrains are restricted [Balaram, (1999) J. Pept. Res. 54, 195-199]. Unlike natural amino acids, Cα-methylated amino acids have a hydrogen atom attached to the $C_\alpha$, which affects widely their sterical properties regarding the $\phi$ and $\psi$ angels of the amide bond. Thus, while alanine has a wide range of allowed $\phi$ and $\psi$ conformations, α-aminoisobutyric acid (Aib, see Table 2, above) has limited $\phi$ and $\psi$ conformations. Hence, peptides of the present invention which are substituted with at least one Aib residue are capable of binding amyloid polypeptides but prevent aggregation thereof (see Examples 40-44). Such peptides are set forth in SEQ ID NOs: 113, 114, 117, 118, 121, 135, 136, 137, 143, 145, 149, 129 and 131.

The β-sheet breaker amino acid of this aspect of the present invention can be located at position Y of the X-Y/Y-X amino acid sequence of the peptide (see for Example SEQ ID NOs: 123, 143, 144, 145, 146, 147, 148). Alternatively, the peptides of this aspect of the present invention can be at least 3 amino acids and include the breaker amino acid in any position other than the X-Y/Y-X amino acid sequence (see for example SEQ ID NO: 117).

The β-sheet breaker amino acid may be positioned upstream of the aromatic residue (see SEQ ID NO: 122) or downstream thereto (see SEQ ID NO: 123).

According to one preferred embodiment of this aspect of the present invention the peptide is three amino acids in length, wherein Y is an aromatic amino acid and an amino acid residue attached to the amino acid sequence X-Y or Y-X is a β-sheet breaker amino acid, which is preferably attached at the C-terminus of the peptide (e.g., SEQ ID NOs: 135 and 140).

According to another preferred embodiment of this aspect of the present invention the peptide is two amino acids in length and Y is a β-sheet breaker amino acid (e.g., SEQ ID NOs: 121, 143-148).

According to a most preferred embodiment of this aspect of the present invention the peptide is a dipeptide having the following general formula:

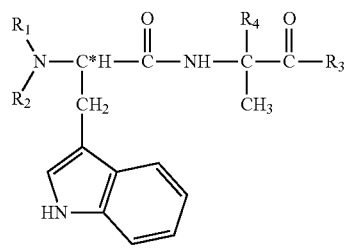

wherein:

C* is a chiral carbon having a D configuration (also referred to in the art as R-configuration).

$R_1$ and $R_2$ are each independently selected from the group consisting of hydrogen, alkyl, cycloalkyl, aryl, carboxy, thiocarboxy, C-carboxylate and C-thiocarboxylate;

$R_3$ is selected from the group consisting of hydroxy, alkoxy, aryloxy, thiohydroxy, thioalkoxy, thioaryloxy, halo and amine; and $R_4$ is alkyl.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, halo, hydroxy, cyano, nitro and amino.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, halo, hydroxy, cyano, nitro and amino.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, cycloalkyl, halo, hydroxy, alkoxy, thiohydroxy, thioalkoxy, cyano, nitro and amino.

A "hydroxy" group refers to an —OH group.

An "alkoxy" group refers to both an —O-alkyl and an —O-cycloalkyl group, as defined herein.

An "aryloxy" group refers to an —O-aryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to an —S-aryl group, as defined herein.

A "carboxy" group refers to a —C(=O)—R' group, where R' is hydrogen, halo, alkyl, cycloalkyl or aryl, as defined herein.

A "thiocarboxy" group refers to a —C(=S)—R' group, where R' is as defined herein for R'.

A "C-carboxylate" group refers to a —C(=O)—O—R' groups, where R' is as defined herein.

A "C-thiocarboxylate" group refers to a —C(=S)—O—R' groups, where R' is as defined herein.

A "halo" group refers to fluorine, chlorine, bromine or iodine.

An "amine" group refers to an —NR'R" group where R' is as defined herein and R" is as defined for R'.

A "nitro" group refers to an —NO$_2$ group.

A "cyano" group refers to a —C≡N group.

Preferably, $R_4$ is methyl, such that the compound above is D-tryptophane-alpha-aminobutyric acid (also referred to herein as D-Trp-aib or D-tryptophane-alpha-methyl-alanine), or a derivative thereof.

It will be appreciated that unmodified di-peptides, peptides of L-configuration, peptides which are of a reversed configuration (i.e., C-to-N sequence of tryptophane (D/L) and alpha-methyl alanine), or alternatively, macromolecules (e.g., peptides, immobilized peptides) which encompass the above-described peptide sequence, are known (see e.g., WO 02/094857, WO 02/094857, EP Pat. No. 966,975, U.S. Pat. Nos. 6,255,286, 6,251,625, 6,162,828 and 5,304,470). However, such molecules are chemically and biologically different than the above described peptide, which unique activity is strictly dependent on its structure.

The peptides of the present invention are preferably utilized in a linear form, although it will be appreciated that in cases where cyclization does not severely interfere with peptide characteristics, cyclic forms of the peptide can also be utilized.

Cyclic peptides can either be synthesized in a cyclic form or configured so as to assume a cyclic form under desired conditions (e.g., physiological conditions).

For example, a peptide according to the teachings of the present invention can include at least two cysteine residues flanking the core peptide sequence. In this case, cyclization can be generated via formation of S—S bonds between the two Cys residues. Side-chain to side chain cyclization can also be generated via formation of an interaction bond of the formula —(—CH2-)n-S—CH2-C—, wherein n=1 or 2, which is possible, for example, through incorporation of Cys or homoCys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH2)n-COOH)—C(R)H—COOH or H—N((CH2)n-COOH)—C(R)H—NH2, wherein n=1-4, and further wherein R is any natural or non-natural side chain of an amino acid.

Thus, the present invention provides conclusive data as to the identity of the structural determinant of amyloid peptides, which directs fibril assembly.

As such, the present invention enables design of a range of peptide sequences, which can be utilized for prevention/treatment or diagnosis of amyloidosis.

As is described in Examples 6-35, the present inventor identified the consensus aromatic sequence of the present invention (SEQ ID NO: 7) in numerous amyloid related proteins, thereby conclusively showing that the present invention enables accurate identification of amyloidogenic fragments in essentially all amyloidogenic proteins.

Figure 2C:
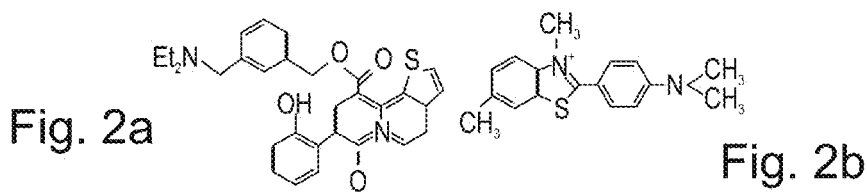
Figure 2C:
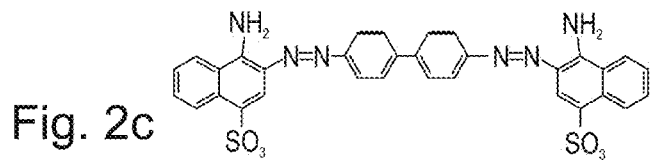

Furthermore, the fact that small aromatic molecules, such as Ro 47-1816/001 [Kuner et al. (2000) J. Biol. Chem. 275: 1673-8, see FIG. 2a] and 3-p-toluoyl-2-[4'-(3-diethylamino-propoxy)-phnyl]-benzofuran [Twyman (1999) Tetrahedron Letters 40:9383-9384] have been demonstrated effective in inhibiting the polymerization of the beta polypeptide of Alzheimer's disease [Findeis et al. (2000) Biochem. Biophys. Acta 1503:76-84], while amyloid specific dyes such as Congo-Red (FIG. 2b) and thioflavin T (FIG. 2c), which contain aromatic elements are generic amyloid formation inhibitors, substantiate the recognition motif of the present invention as sufficient for amyloid self-assembly.

The availability of the peptides of the present invention allows for the generation of antibodies directed thereagainst, which may be used to dissociate or prevent the formation of amyloid plaques (U.S. Pat. No. 5,688,561).

The term "antibody" refers to intact antibody molecules as well as functional fragments thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; and (v) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of V$_H$ and V$_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

For human applications, the antibodies of the present invention are preferably humanized. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

As is mentioned hereinabove, one specific use for the peptides of the present invention is prevention or treatment of diseases associated with amyloid plaque formation.

Thus, according to yet another aspect of the present invention, there is provided a method of treating an amyloid-associated disease in an individual. Preferred individual subjects according to the present invention are mammals such as canines, felines, ovines, porcines, equines, bovines, humans and the like.

The term "treating" refers to reducing or preventing amyloid plaque formation, or substantially decreasing plaque occurrence in the affected tissue. The phrase "amyloid plaque" refers to fibrillar amyloid as well as aggregated but not fibrillar amyloid, hereinafter "protofibrillar amyloid", which may be pathogenic as well. For example, an aggregated but not necessarily fibrillar form of IAPP was found to be toxic in culture. As shown by Anaguiano and co-workers [(2002) Biochemistry 41:11338-43] protofibrillar IAPP, like protofibrillar α-synucelin, which is implicated in Parkinson's disease pathogenesis, permeabilized synthetic vesicles by a pore-like mechanism. The formation of the IAPP amyloid pore was temporally correlated to the formation of early IAPP oligomers and disappearance thereof to the appearance of amyloid fibrils. These results suggest that protofibrillar IAPP may be critical to type II diabetes mellitus as other protofibrillar proteins are critical to the development of Alzheimer's and Parkinson's diseases.

Amyloid-associated diseases treated according to the present invention include, but are not limited to, type II diabetes mellitus, Alzheimer's disease (AD), early onset Alzheimer's disease, late onset Alzheimer's disease, presymptomatic Alzheimer's disease, Perkinson's disease, SAA amyloidosis, hereditary Icelandic syndrome, multiple myeloma, medullary carcinoma, aortic medical amyloid, Insulin injection amyloidosis, prion-systematic amyloidosis, choronic inflammation amyloidosis, Huntington's disease, senile systemic amyloidosis, pituitary gland amyloidosis, Hereditary renal amyloidosis, familial British dementia, Finnish hereditary amyloidosis, familial non-neuropathic amyloidosis [Gazit (2002) Curr. Med. Chem. 9:1667-1675] and prion diseases including scrapie of sheep and goats and bovine spongiform encephalopathy (BSE) of cattle [Wilesmith and Wells (1991) Curr Top Microbiol Immunol 172: 21-38] and human prion diseases including (i) kuru, (ii) Creutzfeldt-Jakob Disease (CJD), (iii) Gerstmann-Streussler-Sheinker Disease (GSS), and (iv) fatal familial insomnia (FFI) [Gajdusek (1977) Science 197: 943-960; Medori, Tritschler et al. (1992) N Engl J Med 326: 444-449].

The method includes providing to the individual a therapeutically effective amount of the peptide of the present invention. The peptide can be provided using any one of a variety of delivery methods. Delivery methods and suitable formulations are described hereinbelow with respect to pharmaceutical compositions.

It will be appreciated that when utilized for treatment of amyloid diseases, the peptide of the present invention includes an amino acid sequence suitable for preventing fibril formation, reducing fibril formation, or disaggregating formed aggregates by competitive destabilization of the preformed aggregate. For example, SEQ ID NOs: 45, 112-123, 125, 127, 128-149 and 150 can be utilized for treatment of amyloid diseases, particularly type II diabetes mellitus since as shown in Example 35 and in Example 45 of the Examples section which follows, such sequences interfere with IAPP self-assembly as demonstrated by the decreased ability of the amyloidogenic peptide to bind thioflavin T in the presence of inhibitory peptides.

Alternatively, the peptides set forth in SEQ ID NOs: 10 or 11 can be used as potent inhibitors of type II diabetes since as shown in the Examples section which follows, substitution of either leucine or isoleucine in the peptide elicits very slow kinetics of aggregation. Since amyloid formation in vivo is a very slow process, it is conceivable that under physiological conditions no fibrilization will occur upon the substitution of isoleucine or leucine to alanine in the context of the full length IAPP.

Alternatively, self-aggregating peptides such as those set forth in SEQ ID NOs. 17, 19 and 28-30, can be used as potent inhibitors of amyloid fibrilization, since such peptides can form heteromolecular complexes which are not as ordered as the homomolecular assemblies formed by amyloid fragments.

It will be appreciated that since one of the main obstacles in using short peptide fragments in therapy is their proteolytic degradation by stereospecific cellular proteases, the peptides of the present invention are preferably synthesized from D-isomers of natural amino acids [i.e., inverso peptide analogues, Tjernberg (1997) J. Biol. Chem. 272:12601-5, Gazit (2002) Curr. Med. Chem. 9:1667-1675].

Additionally, the peptides of the present invention include retro, inverso and retro-inverso analogues thereof. It will be appreciated that complete or extended partial retro-inverso analogues of hormones have generally been found to retain or enhance biological activity. Retro-inversion has also found application in the area of rational design of enzyme inhibitors (see U.S. Pat. No. 6,261,569).

As used herein a "retro peptide" refers to peptides which are made up of L-amino acid residues which are assembled in opposite direction to the native peptide sequence.

Retro-inverso modification of naturally occurring polypeptides involves the synthetic assembly of amino acids with α-carbon stereochemistry opposite to that of the corresponding L-amino acids, i.e., D- or D-allo-amino acids in inverse order to the native peptide sequence. A rerto inverso analogue, thus, has reversed termini and reversed direction of peptide bonds, while essentially maintaining the topology of the side chains as in the native peptide sequence.

Additionally, since one of the main issues in amyloid fibril formation is the transition of the amyloid polypeptide from the native form to stacked β-strand structure, inhibitory peptides preferably include N-methylated amino acids which constrain peptide-backbone due to steric effects [Kapurniotu (2002) 315:339-350]. For example, aminoisobutyric acid (Aib or methyl alanine) is known to stabilize an α-helical structure in short natural peptides. Furthermore, the N-methylation also affects the intermolecular NH to CO H-bonding ability, thus suppressing the formation of multiplayer β-strands, which are stabilized by H-bonding interactions.

It will be further appreciated that addition of organic groups such as a cholyl groups to the N-terminal or C-terminal of the peptides of the present invention is preferred since it was shown to improve potency and bioavailability (e.g., crossing the blood brain barrier in the case of neurodegenerative diseases) of therapeutic peptides [Findeis (1999) Biochemistry 38:6791-6800]. Furthermore, introducing a charged amino acid to the recognition motif, may result in electrostatic repulsion which inhibits further growth of the amyloid fibrils [Lowe (2001) J. Mol. Biol. 40:7882-7889].

As mentioned hereinabove, the antibodies of the present invention may also be used to treat amyloid-associated diseases.

The peptides and/or antibodies of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide or antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the peptides or antibodies of the present invention can also be expressed from a nucleic acid construct administered to the individual employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the peptides or antibodies of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5'LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Because of the self-aggregating nature of the peptides of the present invention it is conceivable that such peptides can also be used as potent detectors of amyloid fibrils/plaques in biological samples. This is of a special significance to amyloid-associated diseases such as Alzheimer's disease wherein unequivocal diagnosis can only be made after postmortem examination of brain tissues for the hallmark neurofibrillary tangles (NFT) and neuritic plaques.

Thus, according to yet another aspect of the present invention there is provided a method of detecting a presence or an absence of an amyloid fibril in a biological sample.

The method is effected by incubating the biological sample with a peptide of the present invention capable of co-aggregating with the amyloid fibril and detecting the peptide, to thereby detect the presence or the absence of amyloid fibril in the biological sample. A variety of peptide reagents, which are capable of recognizing conformational ensembles are known in the art some of which are reviewed in Bursavich (2002) J. Med. Chem. 45(3): 541-58 and in Baltzer Chem. Rev. 101(10):3153-63.

The biological sample utilized for detection can be any body sample such as blood (serum or plasma), sputum, ascites fluids, pleural effusions, urine, biopsy specimens, isolated cells and/or cell membrane preparation. Methods of obtaining tissue biopsies and body fluids from mammals are well known in the art.

The peptide of the present invention is contacted with the biological sample under conditions suitable for aggregate formation (i.e., buffer, temperature, incubation time etc.); suitable conditions are described in Example 2 of the Examples section. Measures are taken not to allow pre-aggregation of peptides prior to incubation with the biological sample. To this end freshly prepared peptide stocks are preferably used.

Protein complexes within a biological sample can be detected via any one of several methods known in the art, which methods can employ biochemical and/or optical detection schemes.

To facilitate complex detection, the peptides of the present invention are highlighted preferably by a tag or an antibody. It will be appreciated that highlighting can be effected prior to, concomitant with or following aggregate formation, depending on the highlighting method. As used herein the term "tag" refers to a molecule, which exhibits a quantifiable activity or characteristic. A tag can be a fluorescent molecule including chemical fluorescers such as fluorescein or polypeptide fluorescers such as the green fluorescent protein (GFP) or related proteins. In such case, the tag can be quantified via its fluorescence, which is generated upon the application of a suitable excitatory light. Alternatively, a tag can be an epitope tag, a fairly unique polypeptide sequence to which a specific antibody can bind without substantially cross reacting with other cellular epitopes. Such epitope tags include a Myc tag, a Flag tag, a His tag, a leucine tag, an IgG tag, a streptavidin tag and the like.

Alternatively, aggregate detection can be effected by the antibodies of the present invention.

Thus, this aspect of the present invention provides a method of assaying or screening biological samples, such as body tissue or fluid suspected of including an amyloid fibril.

It will be appreciated that such a detection method can also be utilized in an assay for uncovering potential drugs useful in prevention or disaggregation of amyloid deposits. For example, the present invention may be used for high throughput screening of test compounds. Typically, the co-aggregating peptides of the present invention are radiolabeled, to reduce assay volume. A competition assay is then effected by monitoring displacement of the label by a test compound [Han (1996) J. Am. Chem. Soc. 118:4506-7 and Esler (1996) Chem. 271:8545-8].

It will be appreciated that the peptides of the present invention may also be used as potent detectors of amyloid deposits in-vivo. A designed peptide capable of binding amyloid deposits, labeled non-radioactively or with a radio-isotope, as is well known in the art can be administered to an individual to diagnose the onset or presence of amyloid-related disease, discussed hereinabove. The binding of such a labeled peptide after administration to amyloid or amyloid-like deposits can be detected by in vivo imaging techniques known in the art.

The peptides of the present invention can be included in a diagnostic or therapeutic kit. For example, peptide sets of specific disease related proteins or antibodies directed thereagainst can be packaged in a one or more containers with appropriate buffers and preservatives and used for diagnosis or for directing therapeutic treatment.

Thus, the peptides can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added.

The peptides of such kits can also be attached to a solid support, such as beads, array substrate (e.g., chips) and the like and used for diagnostic purposes.

Peptides included in kits or immobilized to substrates may be conjugated to a detectable label such as described hereinabove.

The kit can also include instructions for determining if the tested subject is suffering from, or is at risk of developing, a condition, disorder, or disease associated with amyloid polypeptide of interest.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Alanine Scan of the hIAPP Basic Amylodogenic Unit—Rational and Peptide Synthesis Pancreatic amyloid is found in more than 95% of type II diabetes patients. Pancreatic amyloid is formed by the aggregation of a 37 amino acid long islet amyloid polypeptide (IAPP, GenBank Accession No. gi:4557655), the cytotoxicity thereof being directly associated with the development of the disease. IAPP amyloid formation follows a nucleation-dependent polymerization process, which proceeds through conformational transition of soluble IAPP into aggregated β-sheets. Recently it has been shown that a hexapeptide (22-27) (NFGAIL, SEQ ID NO: 111) of IAPP, also termed as the "basic amyloidogenic unit" is sufficient for the formation of β-sheet-containing amyloid fibrils [Konstantinos et al. (2000) J. Mol. Biol. 295:1055-1071].

Figures 3A, 3B, 3C:
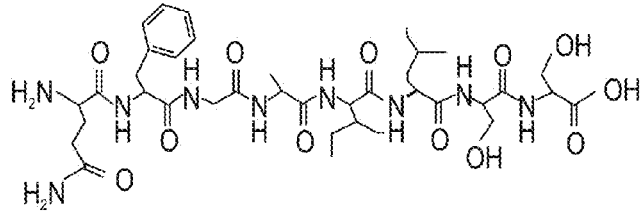
FIGS. 3a-c are schematic illustrations of a primary sequence comparison between human and rodent IAPP and the synthetic peptides of the present invention.

To gain further insight into the specific role of the residues that compose "the "basic amyloidogenic unit", a systematic alanine scan was performed. Amino-acids were replaced with alanine in order to specifically change the molecular interface of the peptides, without significantly changing their hydrophobicity or tendency to form β-sheet structures. Alanine-scan was preformed in the context of the block that is unique to human IAPP (FIG. 3a). This block includes two serine residues that follow the NFGAIL motif in the full-length polypeptide. These eight amino-acid peptide sequences were used since the shorter peptides are hydrophobic and as s such less soluble. FIG. 3b shows a schematic representation of the chemical structure of the wild-type peptide while FIG. 3c indicates the amino-acid substitutions in the different mutant peptides that were generated.

Methods and Reagents—Peptide synthesis was performed by PeptidoGenic Research & Co. Inc (Livermore, Calif. USA). The sequence identity of the peptides was confirmed by ion spray mass-spectrometry using a Perkin Elmer Sciex API I spectrometer. The purity of the peptides was confirmed by reverse phase high-pressure liquid chromatography (RP-HPLC) on a $C_{18}$ column, using a linear gradient of 10 to 70% acetonitrile in water and 0.1% trifluoroacetic acid (TFA).

Example 2

Kinetics of Aggregation of IAPP Peptide Fragment and Mutant Derivatives as Monitored by Turbidity Measurements To study self-assembly of the IAPP peptide derived fragments, aggregation and insolubilization kinetics were monitored using turbidity measurements at 405 nm.

Kinetic Aggregation Assay—Fresh peptide stock solutions were prepared by dissolving lyophilized form of the peptides in DMSO, a disaggregating solvent, at a concentration of 100 mM. To avoid any pre-aggregation, fresh stock solutions were prepared prior to each and every experiment. Peptide stock solutions were diluted into assay buffer and plated in 96-well plates as follows: 2 μl of peptides stock solutions were added to 98 μl of 10 mM Tris pH 7.2, resulting in a 2 mM final concentration of the peptide in the presence of 2% DMSO. Turbidity data was measured at 405 nm. A buffer solution including 2% DMSO was used as a blank. Turbidity was measured at room temperature over several time points.

Figure 4A:
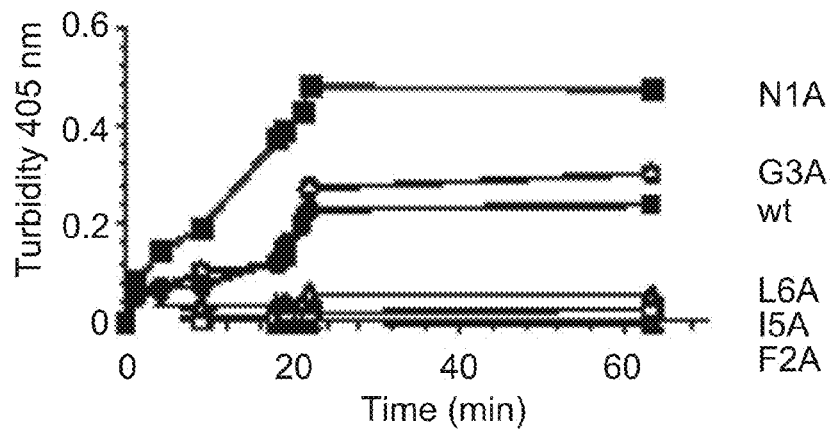
FIGS. 4a-b are graphs illustrating light absorbance at 405 nm as a function of time during fibril formation thus reflecting the aggregation kinetics of IAPP-derived peptides. The following symbols are used: closed squares—N1A, opened circles—G3A, closed circles—wild type, opened triangles—L6A, opened squares—I5A and closed triangles—F2A.
Figure 4B:
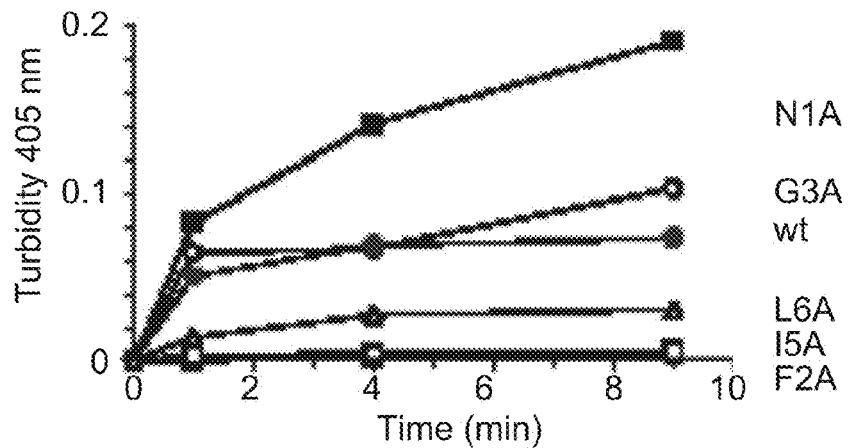

Results—As shown in FIG. 4a, wild-type peptide fragment (SEQ ID NO: 1) showed an aggregation kinetic profile that was very similar to those previously reported for non-seeded hIAPP hexapeptide [Tenidis et al. (2000) J. Mol. Biol. 295: 1055-71]. Such a profile is strongly indicative of a nucleation-dependent polymerization mechanism [Jarrett and Lansbury (1992) Biochemistry 31:6865-70]. Following a lag-time of 20 minutes, wild type peptide self-assembled into insoluble fibrils. Peptide G3A (SEQ ID NO: 4) showed essentially the same profile as that of wild type peptide. The N1A peptide (SEQ ID NO: 2) mediated higher kinetics of aggregation, albeit with different kinetic profile as compared to that of wild-type peptide. Interestingly, the aggregation of N1A seemed to be less nucleation-dependent. Substitution of the isoleucine or leucine to alanine (peptides I5A, SEQ ID NO: 5 and L6A, SEQ ID NO: 6 respectively) reduced the kinetics of aggregation but did not abolish it completely. Substitution of the phenylalanine residue to alanine (peptide F2A, SEQ ID NO:3) led to a total loss of peptide ability to aggregate. The F2A peptide was completely soluble in the aqueous assay buffer.

Altogether, kinetic aggregation studies of the amyloidogenic fragments suggested a major role to the phenylalanine residue in the process of amyloid formation by the IAPP active fragment.

Example 3

Measurement of Aggregate Mean Particle Size

While the turbidity assay provided an important estimate regarding the aggregation potential and kinetics of the various peptides, it did not provide information about the size of the actual aggregates formed. It will be appreciated that although the apparent hydrodynamic diameter of amyloid structures varies due to irregularity of the amyloid structure, it may still provide a clear indication about the order of magnitude of the structure formed and present a quantitative criterion for comparing the structures formed by the various peptides.

Therefore, the average size of the aggregates, formed by the various peptides, was determined using dynamic light scattering (DLS) experiments.

Method—Freshly prepared peptide stock solutions at a concentration of 10 mM were diluted in 10 mM Tris buffer pH 7.2 and further filtrated through a 0.2 μm filter to a final concentration of 100 μM peptide and 1% DMSO. Particle size measurement was conducted with a laser-powered ALV-NIBS/HPPS non-invasive backscattering instrument. Autocorrelation data was fitted using the ALV-NIBS/HPPS software to derive average apparent hydrodynamic diameters.

Figure 5:
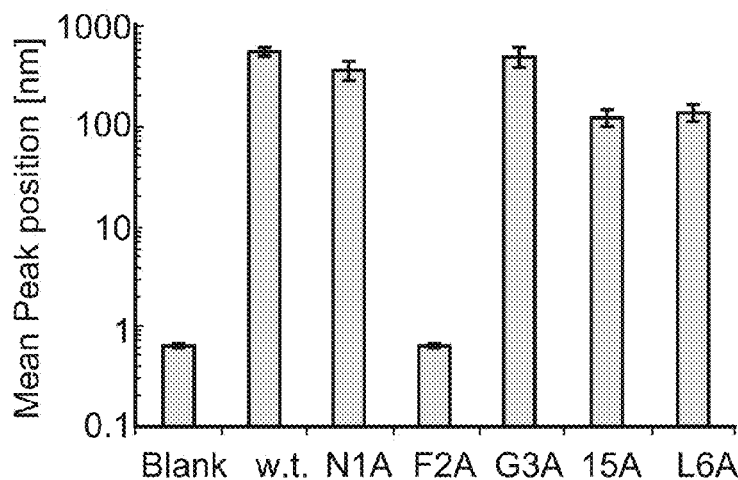
FIG. 5 is a histogram depicting mean particle size of assembled IAPP peptide and derivatives as measured by light scattering. Each column represents the results of 3-5 independent measurements.

Results—The average apparent hydrodynamic diameters of the structures that were formed by the various peptides are presented in FIG. 5.

Altogether, the apparent hydrodynamic diameter of the structures formed by the various peptides seemed to be consistent with the results obtained by the turbidity assay. As with the turbidity assay, the wild-type peptide and G3A peptide formed particles of very similar hydrodynamic diameters. Smaller structures were observed with the derivative peptides: N1A, I5A and L6A. Thus, in accordance with the turbidity assay, the DLS experiments clearly illustrate that no large particles were formed by the F2A peptide under the indicated experimental conditions.

Example 4

Examination of Amyloidogenic Performance of Wild Type Peptide and Derivatives Through Congo Red (CR) Binding Assay Congo red (CR) staining combined with polarization microscopy was utilized to test amyloidogenicity of the peptides of the present invention. Amyloid fibrils in general, and fibrilar IAPP in particular, bind CR and exhibit gold/green birefringence under polarized light [Cooper (1974) Lab. Invest. 31:232-8; Lansbury (1992) Biochemistry 31:6865-70].

Method and Reagents—Peptide solutions incubated in a 10 mM Tris buffer (pH 7) for four days were dried on a glass microscope slide. Staining was effected by the addition of 1 mM CR in 10 mM Tris buffer pH 7.2 followed by a 1 minute incubation. To remove excess CR, slides were rinsed with double-distilled water and dried. Saturated CR solutions solubilized in 80% ethanol (v/v) were used for poorly aggregating peptides. In such cases, staining was effected without rinsing. Birefringence was determined using a WILD Makroskop m420 (×70) equipped with a polarizing stage.

Results—Wild type, N1A and G3A peptides bound CR and exhibited the characteristic green/gold birefringence (see FIGS. 6g, 6a and 6e for normal field and FIGS. 6h, 6b and 6f for polarized light microscopy, respectively). Peptides I5A and L6A, bound CR and exhibited rare but characteristic birefringence (FIGS. 6i and 6k for normal field and FIGS. 6j and 6l for polarized light, respectively). Peptide F2A (NA-GAIL) showed no capability of binding CR (FIG. 6c for normal field and FIG. 6d for polarized light). Dried buffer solution stained with CR was used as a negative control (see FIGS. 6m and 6n for normal and polarized light, respectively). Interestingly, no significant difference in binding was observed for the negative control and the F2A peptide.

To substantiate the inability of F2A peptide to form fibrils, a peptide solution incubated for 14 days was used in the binding assay. Although some degree of aggregation was visually observed following two weeks of peptide "aging", CR staining showed no amyloid structure (results not shown). Under the same conditions wild-type peptide incubation resulted in significant CR birefringence.

Example 5

Ultrastructural Analysis of the Fibrillogenic Peptide and Mutants

The fibrillogenic potential of the various peptides was assessed by electron microscopy analysis.

Method—Peptide solutions (2 mM peptide in 10 mM Tris buffer pH 7.2), were incubated overnight at room temperature. Fibrils formation was assessed using 10 µl sample placed on 200-mesh copper grids, covered with carbon-stabilized formvar film (SPI Supplies, West Chester Pa.). Following 20-30 seconds of incubation, excess fluid was removed and the grids were negatively stained with 2% uranyl acetate in water. Samples were viewed in a JEOL 1200EX electron microscope operating at 80 kV.

Figure 7A:
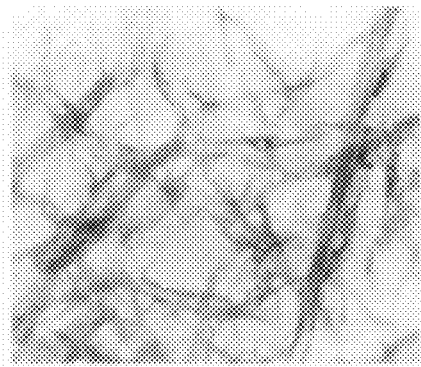
FIGS. 7a-f are electron micrographs of "aged" IAPP peptide and derivatives. N1A peptide (FIG. 7a), F2A peptide (FIG. 7b), G3A peptide (FIG. 7c), wild type peptide (FIG. 7d), I5A peptide (FIG. 7e) and L6A (FIG. 7f). The indicated scale bar represents 100 nm.
Figure 7B:
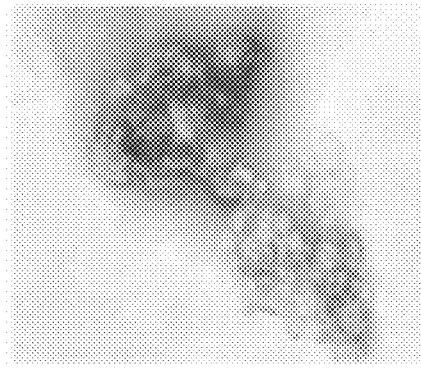
Figure 7C:
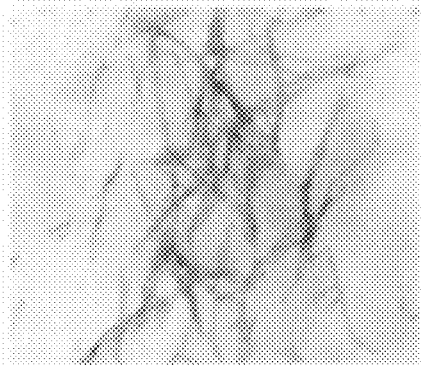
Figure 7D:
Figure 7E:
Figure 7F:
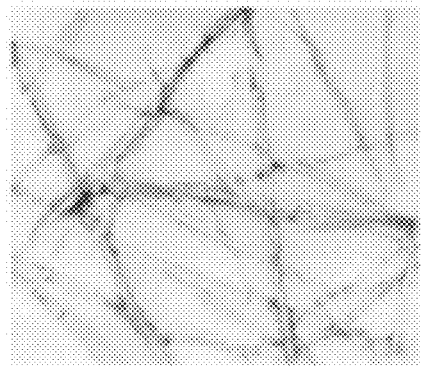

Results—To further characterize the structures formed by the various peptides, negative staining electron microscopy analysis was effected. In accordance with previous results, filamentous structures were observed for all peptides (FIGS. 7a-f) but F2A which generated amorphous fibrils (FIG. 7b). Frequency of appearance of fibrils formed by the I5A and L6A peptides (FIGS. 7e and 7f, respectively) was lower in comparison to that of wild type (FIG. 7d), N1A, and G3A peptides (FIGS. 7a and 7c, respectively). Although the EM fields shown for peptides F2A, I5A and L6A, were rarely observed, the results presented by these images support the quantitative results presented in the previous sections and thus provide qualitative analysis of fibril morphology.

The tangled net-like structures that were observed for the wild-type, N1A, and G3A peptides could be explained by the fast kinetics of formation of these fibrils (see Example 2). More distinct structures and longer fibrils, albeit less frequent, were observed with peptides I5A and L6A. These longer fibrils may be a result of a slower kinetics, which allow for a more ordered fibril organization.

Taken together, the qualitative results of the electron microscopy and CR analyses strongly suggest that the phenylalanine residue in the hexaamyloid peptide is crucial for its amyloidogenic potential.

Example 6

Mapping Recognition Domains in the hIAPP Basic Amyloidogenic Unit—Rational and MBP-IAPP Fusion Protein Synthesis To systematically map and compare potential recognition domains, the ability of hIAPP (GenBank Accession No. gi:4557655) to interact with an array of 28 membrane-spotted overlapping peptides that span the entire sequence of hIAPP (i.e., $hIAPP_{1-10}$, $hIAPP_{2-11}$ .... $hIAPP_{28-37}$) was addressed [Mazor (2002) J. Mol. Biol. 322:1013-24].

Materials and Experimental Procedures

Bacterial Strains—E. coli strain TG-1 (Amersham Pharmacia, Sweden) was used for molecular cloning and plasmid propagation. The bacterial strain BL21(DE3) (Novagen, USA) was used for protein overexpression.

Engineering Synthetic IAPP and MBP-IAPP Fusion Proteins—A synthetic DNA sequence of human IAPP modified to include a bacterial codon usage (SEQ ID NO: 58) was generated by annealing 8 overlapping primers (SEQ ID NOs. 50-57). PCR was effected through 30 cycles of 1 minute at 95° C., one minute at 55° C., and one minute at 72° C. The annealing product was ligated and amplified using primers IAPP1 (SEQ ID NO: 50) and IAPP8 (SEQ ID NO: 57). An MBP-IAPP (MBP GenBank Accession No. gi:2654021) fusion sequence was then constructed using the IAPP synthetic template, which was amplified using primer YAR2 (SEQ ID NO: 60) and primer YAR1 (SEQ ID NO. 59), thereby introducing a V8 Ek cleavage site and a $(His)_6$ tag at the N-terminus of IAPP. The two primers included a Not I and an Nco I cloning sites, respectively. The resultant PCR product was digested with Nco I and Not I and ligated into the pMALc2x-NN expression vector. The pMALc2x-NN expression vector was constructed by cloning the polylinker site of pMALc-NN[19] into pMALc2x (New England Biolabs, USA) [BACH (2001) J. Mol. Biol. 312:79-93].

Protein Expression and Purification—E. coli BL21 cells transformed with expression plasmid pMALc2x-IAPP encoding MBP-IAPP under the strong Ptac promoter were grown in 200 ml of LB medium supplemented with 100 µg/ml ampicillin and 1% (W/V) glucose. Once reaching an optical density of $A_{600}$=0.8, protein expression was induced with 0.1 or 0.5 mM IPTG at 30° C. for 3 hours (h).

Cell extracts were prepared in 20 mM Tric-HCl (pH 7.4), 1 mM EDTA, 200 mM NaCl and a protease inhibitors cocktail (Sigma) using a freeze-thaw followed by a brief sonication as previously described [Gazit (1999) J. Biol. Chem. 274:2652-2657]. Protein extracts were clarified by centrifugation at 20,000 g and stored at 4° C. MBP-IAPP fusion protein was purified by passing the extract over an amylose resin column (New England Biolabs, USA) and recovered by elution with 20 mM maltose in the same buffer. Purified MBP-IAPP was stored at 4° C. Protein concentration was determined using the Pierce Coomassie plus reagent (Pierce, USA) with BSA as a standard. MBP and MBP-IAPP protein fractions were analyzed on SDS/12% polyacrylamide gels, which were stained with GelCode Blue (Pierce, USA).

To study whether the disulfide bond in the MBP-IAPP are oxidized, purified MBP and MBP-IAPP proteins were reacted with 5 equivalents of N-iodoacetyl-N'-(8-sulfo-1-naphthyl)ethylenediamine (IAEDANS) (Sigma, Rehovot, Israel) for overnight at room temperature in the dark. Free dye was separated from labeled protein by gel filtration chromatography on a QuickSpin G-25 Sephadex column. MBP and MBP-IAPP fluorescence was then determined. Only small fluorescence labeling was detected (on average less than 0.1 probe molecules per protein molecules) and there was no significant difference between the labeling of MBP and MBP-IAPP, which suggested that the disulfide bridge in the expressed IAPP molecules was predominantly oxidized.

Results

Figure 8B:
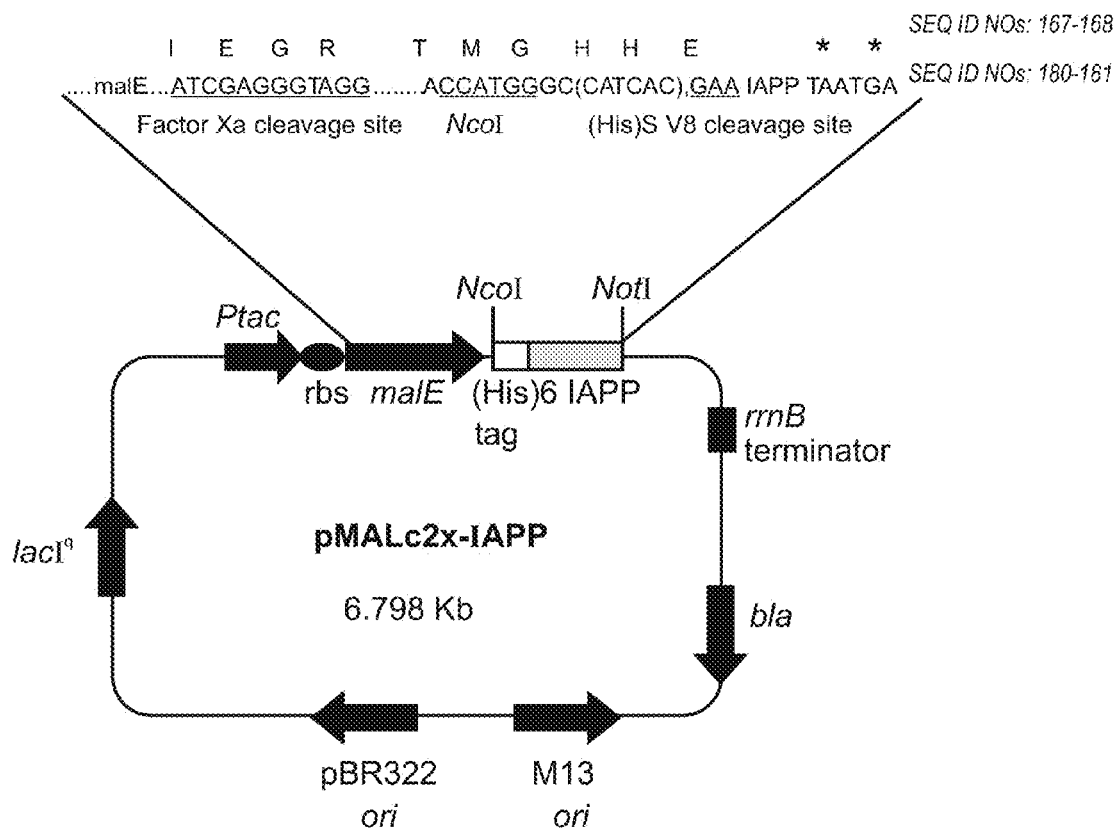
FIG. 8b is a schematic illustration of the pMALc2x-NN vector which is used for cytoplasmic expression of the 48 kDa MBP-IAPP protein. The V8 Ek cleavage site and the $(His)_6$ tag are fused C-terminally to the malE tag vector sequence. A factor Xa cleavage site for removal of the MBP tag is indicated.
Figure 9:
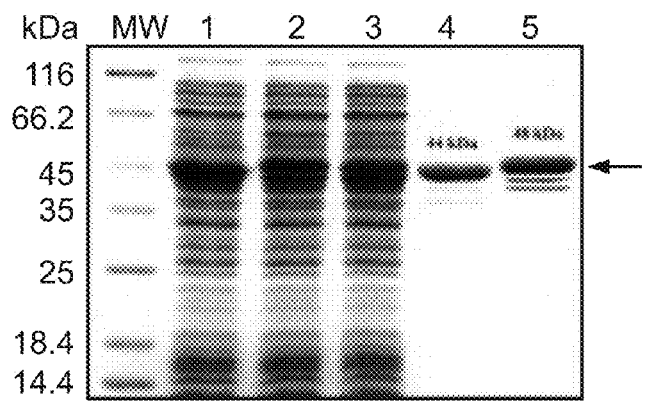
FIG. 9 is a protein gel GelCode Blue staining depicting bacterial expression and purification of MBP and MBP-IAPP fusion protein. Bacterial cell extracts were generated and proteins were purified on an amylose resin column. Samples including 25 μg protein were loaded in each of Lanes 1-3 whereas 5 μg protein were loaded on each of lanes 4-5. Proteins were resolved on a 12% SDS-PAGE and visualized with GelCode Blue staining. A molecular weight marker is indicated on the left. Lane 1-0.5 mM IPTG-induced soluble extract of MBP. Lane 2-0.1 mM IPTG-induced soluble extract of MBP-IAPP. Lane 3-0.5 mM IPTG-induced soluble extract of MBP-IAPP. Lane 4—purified MBP. Lane 5—purified MBP-IAPP. An arrow marks the MBP-IAPP.

Expression and Purification of Recombinant MBP-IAPP—Since previous attempts to express the intact hIAPP in bacteria were unsuccessful, the protein was expressed as an MBP fusion, which protected hIAPP from undesirable aggregation during expression [Bach (2001) J. Mol. Biol. 312:79-93]. Synthesis of the fusion protein was effected using a bacterial codon usage as shown in FIG. 8a. The resulting fusion sequence was cloned into pMALc2x-NN as shown in FIG. 8b and introduced into E. coli BL21(DE3). Growth conditions, cell extract preparation and protein purification were effected as described hereinabove. IPTG induction resulted in the accumulation of high levels of MBP-IAPP in the soluble fraction with less then 5% of the MBP-IAPP fusion protein was found in the insoluble fraction of the cell extract (data not shown). Aliquots from typical purification steps of MBP and MBP-IAPP are shown in FIG. 9. As shown, the 48 kDa MBP-IAPP accumulated to 25% of the total soluble protein as calculated by densitometric scanning of GelCode Blue-stained SDS/Polyacrylamide gels. When induced at 30° C. in a shake flask ($A_{600}$=2.0), MBP-IAPP accumulated as soluble protein in the cytoplasm at a level of about 150 mg/l of cell culture. Despite losses during purification, MBP-IAPP was purified to near-homogeneity at a yield of 80 mg/l of cells. For future application and convenient homogeneity purification of IAPP, in addition to the factor Xa cleavage site for removal of the MBP tag, an additional His-Tag was also included (FIG. 8b). The His-Tag could be removed by Ek V8 cleavage at the N-terminal Lys residue of the IAPP sequence, resulting in the release of wild type IAPP.

Example 7

Identification of Molecular Recognition Sequences in the hIAPP Polypeptide

IAPP Peptide Array Construction—Decamers corresponding to consecutive overlapping sequences of $hIAPP_{1-37}$ SEQ ID NOs. 61-88) were synthesizes on a cellulose membrane matrix using the SPOT technique (Jerini AG, Berlin, Germany). The peptides were covalently bound to a Whatman 50 cellulose support (Whatman, Maidstone, England) via the C-terminal amino-acids. N-terminal acetylation was used for peptide scanning because of higher stability to peptide degradation, and better representation of the native recognition motif.

Peptides Synthesis—Peptide synthesis was effected using solid-phase synthesis methods performed by Peptron, Inc. (Taejeon, Korea). Correct identity of the peptides was confirmed by ion spray mass-spectrometry using a HP 1100 series LC/MSD [Hewlett-Packard Company, Palo Alto, Calif.]. The purity of the peptides was confirmed by reverse phase high-pressure liquid chromatography (RP-HPLC) on a $C_{18}$ column, using a 30 minute linear gradient of 0 to 100% acetonitrile in water and 0.1% trifluoroacetic acid (TFA) at flow rate of 1 ml/min.

Binding Studies—The cellulose peptide array was initially blocked with 5% (V/V) non fat milk in Tris buffered saline (TBS, 20 mM Tris pH 7.5, 150 mM NaCl). Thereafter, cellulose membrane was incubated in the presence of 10 μg/ml $MBP-IAPP_{1-37}$ at 4° C. for 12 h in the same blocking buffer. The cellulose membrane was then washed repeatedly with 0.05% Tween 20 in TBS. $MBP-IAPP_{1-37}$ bound to the cellulose membrane was detected with an anti MBP monoclonal antibody (Sigma, Israel). HRP-conjugated goat anti mouse antibodies (Jackson Laboratories, USA) were used as a secondary antibody. Immunoblots were developed using the Renaissance western blot Chemiluminescence Reagent (NEN, USA) according to Manufacturer's instructions and signal was quantified using densitometry. Regeneration of the cellulose membrane for reuse was carried out by sequential washing with Regeneration buffer I including 62.5 mM Tris, 2% SDS, 100 Mm 2-mercaptoethanol, pH 6.7, and Regeneration buffer II including 8 M urea, 1% SDS, 0.1% 2-mercaptoethanol. Efficiency of the washing steps was monitored by contacting the membrane with the chemiluminescence reagent, as described.

Results

Identification of Binding Sequences in the IAPP Polypeptide—To identify structural motifs in the IAPP molecule that mediates the intermolecular recognition between hIAPP molecules, 28 possible overlapping decamers corresponding to amino acids 1-10 up to 28-37 of the $hIAPP_{1-37}$ molecule were synthesized on a cellulose membrane matrix. Cellulose membrane-bound peptides were incubated with $MBP-hIAPP_{1-37}$ overnight. Following washing of the cellulose membrane in a high-salt buffer, immunoblots on the cellulose membrane were analyzed and binding was quantified by densitometry (FIG. 10b). It will be appreciated that the measured binding is semiquantitative, since peptide coupling efficiency during synthesis can vary.

Figure 10A:
FIGS. 10a-b are a dot-blot image (FIG. 10a) and densitometric quantitation thereof (FIG. 10b) depicting putative amyloidogenic sequences in hIAPP.
Figure 10B:
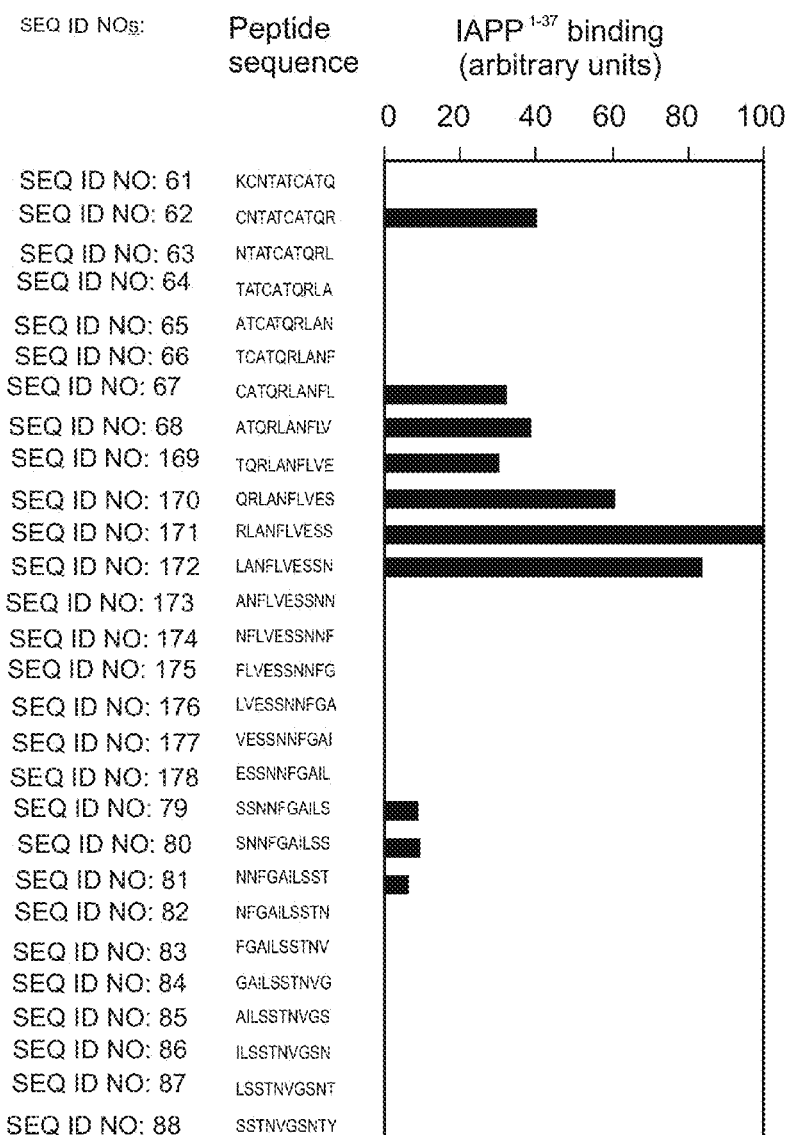

As shown in FIGS. 10a-b, a number of peptide segments exhibited binding to MBP-IAPP; An amino acid sequence localized to the center of the IAPP polypeptide (i.e., $hIAPP_{7-16}$ to $hIAPP_{12-21}$) displayed the most prominent binding to $MBP-hIAPP_{1-37}$. Another binding region was identified at the C-terminal part of IAPP ($hIAPP_{19-28}$ to $hIAPP_{21-30}$), although binding in this case was considerably less prominent; A third binding spot was located to the N-terminal part of IAPP ($hIAPP_{2-11}$), however, no typical distribution around a central motif was evident in this case, suggesting that this result may be false. Even after overexposure of the blot (data not shown), no binding near this peptide (to either $hIAPP_{1-10}$ or $hIAPP_{3-12}$) was detected. Furthermore given the close proximity of the 2-11 region to the disulfide bridge may not allow the process of fibrillization under physiological conditions.

To rule out involvement of MBP itself in binding the arrayed peptides, the peptide coupled cellulose membrane was incubated with MBP alone and analyzed by immunobloting. No binding was identified after development of the membrane (not shown).

These results identified in addition to the previously defined binding motif of hIAPP [i.e., basic amyloidogenic unit, hIAPP20-29, Westermark (1990) Proc. Natl. Acad. Sci. 13:5036-40; Tenidis (2000) J. Mol. Biol. 295:1055-1071; Azriel and Gazit (2001) J. Biol. Chem. 276:34156-34161], a major central domain of molecular recognition within hIAPP. The profile of the binding distribution of the peptide array (FIG. 10b), suggests that NFVLH (SEQ ID No. 17) may serve as the core recognition motif.

Example 8

Characterization of Aggregation Kinetics of hIAPP Peptide Fragments as Monitored by Turbidity Measurements Binding analysis of the recombinant MBP-hIAPP fusion protein to the hIAPP peptide array (Example 7), identified a putative self-assembly domain within the central part of the hIAPP protein.

In order to identify the minimal structural motif that is capable of forming amyloid fibrils, a series of peptides encompassed within the putative self-assembly domain were tested for aggregation as monitored using turbidity measurements at 405 nm.

Table 3 below, illustrates the examined peptides.

TABLE 3

| HIAPP peptide fragments (hIAPP coordinates) | SEQ ID NO: | Peptide sequence |
| --- | --- | --- |
| 14-22 | 14 | NFLVHSSNN |
| 14-20 | 15 | NFLVHSS |
| 15-20 | 16 | FLVHSS |
| 14-18 | 17 | NFLVH |

TABLE 3-continued

| HIAPP peptide fragments (hIAPP coordinates) | SEQ ID NO: | Peptide sequence |
|---|---|---|
| 15-19 | 18 | FLVHS |
| 15-18 | 19 | FLVH |

Materials and Experimental Procedures

Kinetic Aggregation Assay—freshly prepared peptide stock solutions were generated by dissolving the lyophilized form of the peptides in dimethyl sulfoxide (DMSO) at a concentration of 100 mg/ml. To avoid any pre-aggregation, fresh stock solutions were prepared for each experiment. Peptide stock solutions were diluted into the assay buffer in enzyme-linked immunosorbent assay (ELISA) plate wells as follows: 8 μL of peptide stock solutions were added to 92 μL of 10 mM Tris, pH 7.2 (hence the final concentration of the peptide was 8 mg/ml in the presence of 8% DMSO). Turbidity data were collected at 405 nm. Buffer solution containing the same amount of DMSO as the tested samples was used as blank, which was subtracted from the results. Turbidity was measured continuously at room temperature using THERMOmax ELISA plate reader (Molecular Devices, Sunnyvale Calif.).

Results

Figure 11:
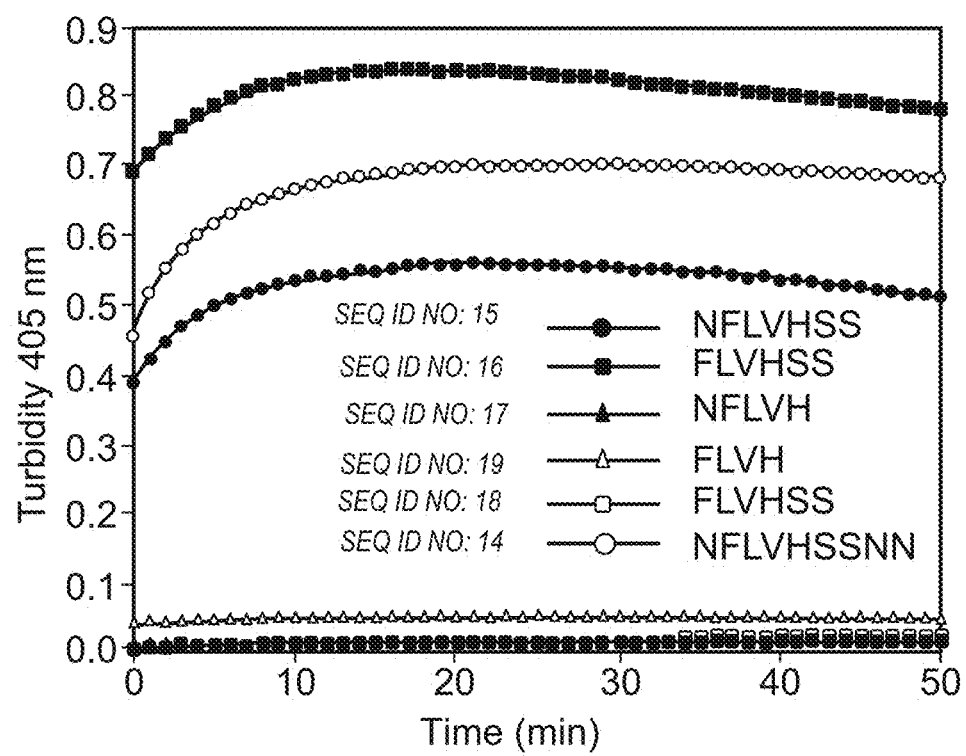
FIG. 11 is a graphic illustration depicting light absorbance at 405 nm as a function of time during fibril formation thus reflecting the aggregation kinetics of IAPP-derived peptides (SEQ ID NOs. 14-19).

Turbidity assay was performed in-order to determine the ability of the various peptides (Table 3) to aggregate in an aqueous medium. Fresh stock solutions of the different peptide fragments were made in DMSO, and then diluted into a Tris buffer solution and turbidity, as a hallmark of protein aggregation, was monitored for two hours. As shown in FIG. 11, the peptides NFLVHSS, FLVHSS and FLVHS exhibited high turbidity. It will be appreciated that the lag-time, as was previously reported for amyloid formation by the NFGAIL short peptide [Tenidis (2000) Supra], is very short or lacking at all and thus could not be detected under these experimental conditions, however the aggregation kinetic profiles were similar to those obtained for the hexapeptide hIAPP$_{22-27}$ (NFGAIL). On the other hand, the peptide NFLVHSSNN exhibited very low turbidity, while NFLVH and FLVH have shown almost no turbidity at all. Even after significantly longer incubation no significant turbidity was observed with the latter two peptides. The lack of amyloid fibrils formation may be due to electrostatic repulsion of the partially charged histidine residues.

Example 9

Examination of hIAPP Peptide Amyloidogenic Through Congo Red (CR) Binding Assay

Congo red (CR) staining combined with polarization microscopy was utilized to test amyloidogenicity of the peptides of the present invention. Amyloid fibrils bind CR and exhibit gold/green birefringence under polarized light [Puchtler (1966) J. Histochem. Cytochem. 10:355-364].

Materials and Experimental Procedures

Congo Red Staining and Birefringence—A 10 μL suspension of 8 mg/ml peptide solution in 10 mM Tris buffer, pH 7.2 aged for at least one day was allowed to dry overnight on a glass microscope slide. Staining was performed by the addition of a 10 μL suspension of saturated Congo Red (CR) and NaCl in 80% ethanol (v/v) solution as previously described [Puchtler (1966) Supra]. The solution was filtered via 0.45 μm filter. The slide was then dried for few hours. Birefringence was determined with a SZX-12 Stereoscope (Olympus, Hamburg, Germany) equipped with cross polarizers.

Results

Figure 12A:
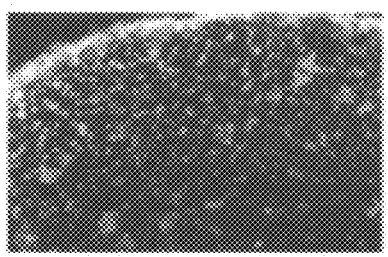
FIGS. 12a-f are photomicrographs illustrating Congo Red binding to pre-assembled IAPP peptides. Polarized field micrographs are shown for each of the following one day aged peptide suspensions: NFLVHSSNN peptide (FIG. 12a), NFLVHSS (FIG. 12b), FLVHSS (FIG. 12c), NFLVH (FIG. 12d), FLVHS (FIG. 12e) and FLVH (FIG. 12f).
Figure 12B:
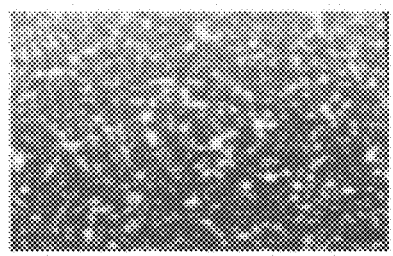
Figure 12C:
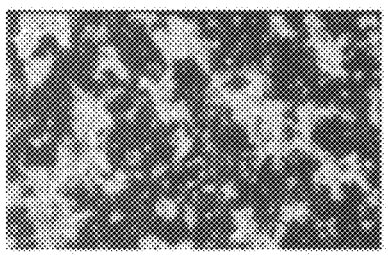
Figure 12D:
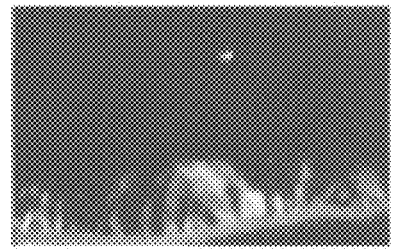
Figure 12E:
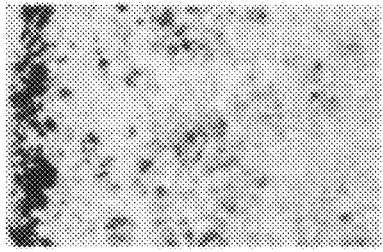
Figure 12F:
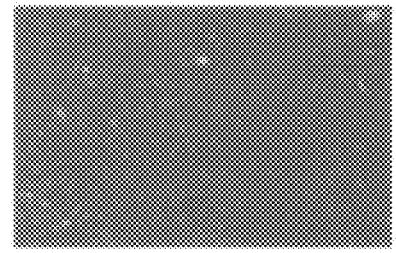

Congo Red Staining and Birefringence—In order to determine any possible amyloidal nature of the aggregates formed at the turbidity assay (see Example 8), a CR birefringence assay was performed. Peptide fragments were tested for amyloidogenecity by staining with CR and examination under a light microscope equipped with cross-polarizers. Consistent with the kinetic assay results, and as shown in FIGS. 12b-c and 12e, the peptides NFLVHSS, FLVHSS and FLVHS exhibited a typical birefringence. On the other hand, peptides NFLVHSSNN, NFLVH and FLVH exhibited very weak birefringence or no birefringence at all (FIGS. 12a, 12d and 12f). Peptide NFLVHSSNN exhibited a weaker characteristic birefringence (FIG. 12a). The peptide NFLVH exhibited a powerful smear of birefringence at the edges of the sample (FIG. 12d). The peptide FLVH exhibited no birefringence (FIG. 12f). In order to test whether the FLVH peptide did not form amyloid fibrils due to a long lag-time, a sample of five days aged peptide solution was examined. The same peptide was also tested in aqueous solution and at very high concentrations (10 mg/ml), however no Birefringence was detected in all cases indicating the peptide did not form amyloid (data not shown).

Example 10

Ultrastructural Analysis of the Fibrillogenic hIAPP Peptides

The fibrillogenic potential of the various peptides was assessed by electron microscopy analysis.

Materials and Experimental Procedures

Transmission Electron Microscopy—A 10 μL sample of 8 mg/ml peptide solution in 10 mM Tris buffer, pH 7.2 aged for at least one day was placed on 400-mesh copper grids (SPI supplies, West Chester Pa.) covered by carbon-stabilized Formvar film. Following 1 minute, excess fluid was removed, and the grid was then negatively stained with 2% uranyl acetate in water for another two minutes. Samples were viewed in a JEOL 1200EX electron microscope operating at 80 kV.

Results

Figure 13A:
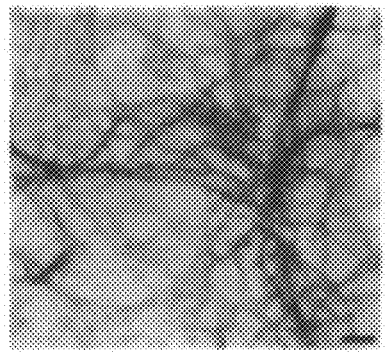
FIGS. 13a-f are electron micrographs of "aged" IAPP peptides. NFLVHSSNN peptide (FIG. 13a), NFLVHSS (FIG. 13b), FLVHSS (FIG. 13c), NFLVH (FIG. 13d), FLVHS (FIG. 13e) and FLVH (FIG. 13f). The indicated scale bar represents 100 nm.
Figure 13B:
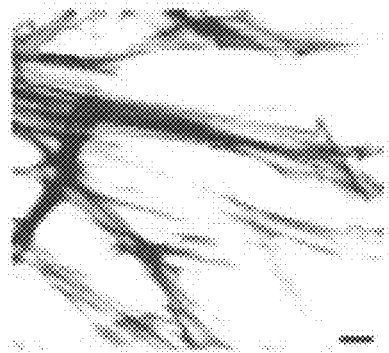
Figure 13C:
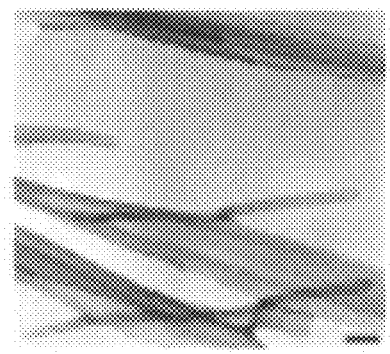
Figure 13D:
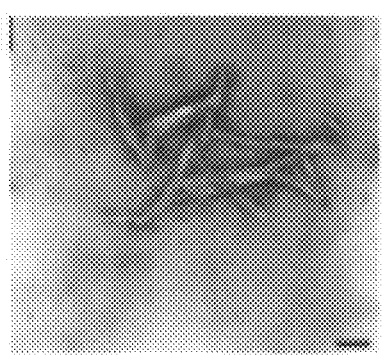
Figure 13E:
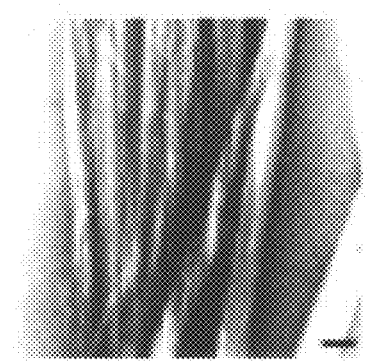
Figure 13F:
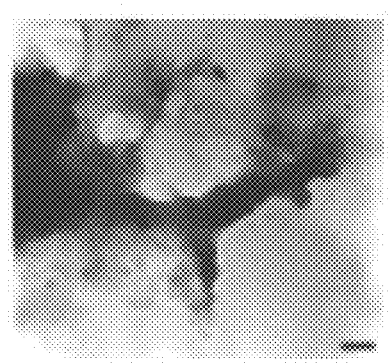

To further characterize the structures formed by the various peptides, negative staining electron microscopy analysis was effected. In accordance with previous results, all peptide fragments exhibited fibrillar structures except the FLVH peptide in which only amorphous aggregates were found (FIGS. 13a-f). NFLVHSSNN peptide exhibited long thin coiling filaments similar to those formed by the full-length peptide as described above (FIG. 13a). Peptides NFLVHSS, FLVHSS, FLVHS exhibited large broad ribbon-like fibrils as described for the NFGAIL fragment [Tenidis (2000) Supra., FIGS. 13c-e, respectively]. The fibrils formed by NFLVH peptide were thin and short and could be considered as protofilaments rather than filaments. Their appearance was at much lower frequency, and the EM picture does not represent the general fields but rather rare events (FIG. 13d). As shown in FIG. 13f, the FLVH peptide mediated the formation of amorphous aggregates.

Example 11

Secondary Structure Analysis of hIAPP Peptide Fragments

Fourier transform infrared spectroscopy (FT-IR) was effected to determine the secondary structure of the hIAPP amyloidogenic peptide fibrils and the non-fibrillar peptides.

Materials and Experimental Procedures

Fourier Transform Infrared Spectroscopy—Infrared spectra were recorded using a Nicolet Nexus 470 FT-IR spectrometer with a DTGS detector. Samples of aged peptide solutions, taken from turbidity assay, were suspended on a CaF$_2$ widows (Sigma)-plate and dried by vacuum. The peptide deposits were resuspended with double-distilled water and subsequently dried to form thin films. The resuspension procedure was repeated twice to ensure maximal hydrogen to deuterium exchange. The measurements were taken using a 4 cm$^{-1}$ resolution and 2000 scans averaging. The transmittance minima values were determined by the OMNIC analysis program (Nicolet).

Results

Figure 14:
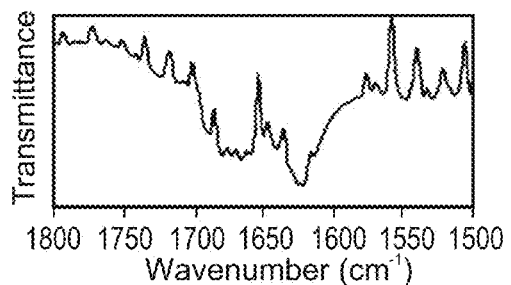
FIGS. 14a-f are graphs showing secondary structures in the insoluble IAPP aggregates as determined by Fourier transformed infrared spectroscopy. NFLVHSSNN peptide (FIG. 14a), NFLVHSS (FIG. 14b), FLVHSS (FIG. 14c), NFLVH (FIG. 14d), FLVHS (FIG. 14e) and FLVH (FIG. 14f).
Figure 14:
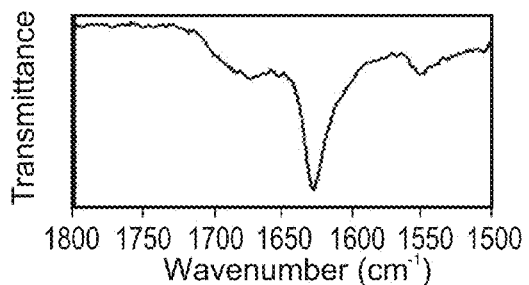
Figure 14:
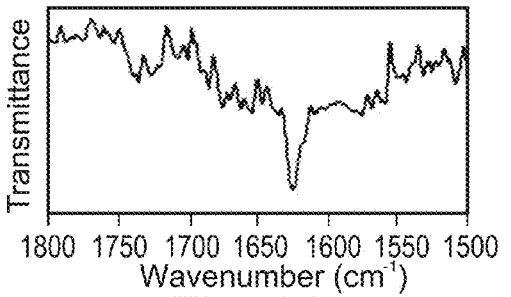
Figure 14:
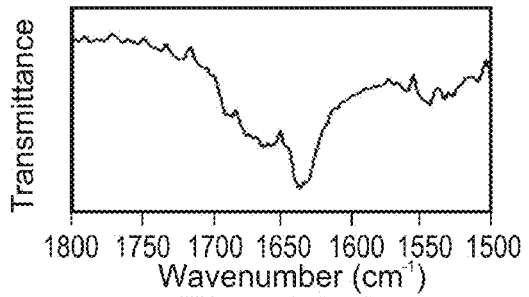
Figure 14:
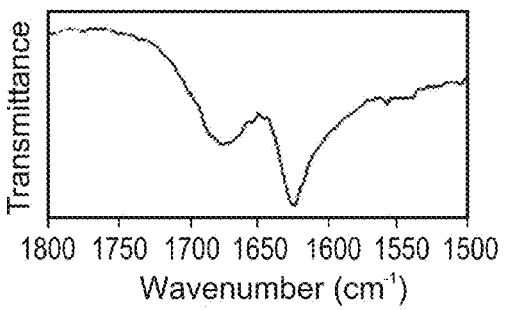
Figure 14:
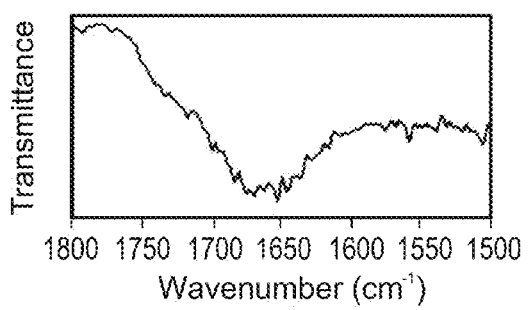

FT-IR Studies—As shown in FIG. 14a-f, all the fibrillar peptides exhibited FT-IR spectra with a well-defined minimum bands typical for β-sheet structure around 1620-1640 cm$^{-1}$. On the other hand the spectrum of the tetrapeptide FLVH that has no appearance for fibrils according to the other methods, is typical for a random coil structure. The NFLVHSSNN peptide spectrum exhibited a transmittance minimum at 1621 cm$^{-1}$ indicating a large β-sheet content, as well as minima at 1640 cm$^{-1}$ and 1665 suggesting presence of non-β structures. Another minor minimum was observed at 1688 cm$^{-1}$ indicative for anti-parallel β-sheet (FIG. 14a). The NFLVHSS peptide spectrum exhibited major minimum band at 1929 cm$^{-1}$ 1675 cm$^{-1}$. this spectrum is classical for an anti-parallel β-sheet structure (FIG. 14b). A similar spectrum was observed for the peptide FLVHS with a major minimum at 1625 cm$^{-1}$ and a minor minimum at 1676 cm$^{-1}$ (FIG. 14e). The spectrum of FLVHSS peptide showed also a major minimum at 1626 cm$^{-1}$. The spectrum had also some minor minima around 1637-1676 cm$^{-1}$ but those were shaped more like noise than signal (FIG. 14c). The spectrum of NFLVH peptide showed a minimum at 1636 cm$^{-1}$ which was also indicative of β-sheet, however, in comparison with the other spectra, this band was shifted which could indicate presence of non-β structures, as well as observed minima at 1654 cm$^{-1}$ and 1669 cm$^{-1}$ (FIG. 14d). By contrast, the FLVH peptide spectrum exhibited no minimum at 1620-1640 cm$^{-1}$, but showed multiple minima around 1646-1675 cm$^{-1}$ typical to random coil structure (FIG. 14f).

To study whether the FLVH tetrapeptide could not form amyloid fibrils at all or the undetectable fibrils formation was a result of a slow kinetics, a solution of the peptide at the same experimental conditions was incubated for two months and the existence of fibrils was tested. However, no evidence for amyloid fibril formation was detected using EM microscopy, CR staining, or FT-IR spectroscopy. These results may suggest that tetrapeptides are incapable of forming fibrils due to energetic consideration. That is, the energetic contribution of the stacking of a strand composed of three peptide bonds is lower than the entropic cost of oligomerization.

Taken together, the ultrastructural observations are consistent with the findings as determined by the turbidity and Congo red birefringence assays. All together the experimental data identified a novel pentapeptide element within the hIAPP peptide, the FLVHS peptides, which has strong amyloid forming capability. Interestingly, an NFLVH peptide found in the same central domain of the hIAPP polypeptide was found to be amyloidogenic however, the ability thereof to form fibrils was somehow inferior.

Example 12

Identification of the minimal amyloidogenic peptide fragment of Medin

Background

Medin (GenBank Accession No. gi:5174557) is the main constitute of aortic medial amyloid deposits [Häggqvist (1999) Proc. Natl. Acad. Sci. USA. 96:8674-8669]. Previous studies found aortic medial amyloid in 97% of the subjects above the age of 50 [Mucchiano (1992) Am. J. Pathol. 140: 811-877]. However, the pathological role of those amyloid deposits is still unknown. It was suggested that these amyloid play a role in the diminished elasticity of aortic vessels that is related to old age [Mucchiano (1992) Supra; Häggqvist (1999) Supra]. While the study clearly identified a tryptic peptide NFGSVQFV as the medin amyloidogenic peptide, the minimal sequence of the peptide that is still amyloidogenic and the molecular determinants that mediate the amyloid formation process were not determined. Such information is critical for true understanding of the fibrillization process in the specific case of Medin but also as a paradigm for the process of amyloid fibrils formation in general.

The minimal active fragment of Medin was determined using functional and structural analyses of truncated analogues derived from the published octapeptide [Häggqvist (1999) Supra].

Materials and Experimental Procedures

Peptide synthesis is described in Example 7.

Table 4 below illustrates the studied peptides.

TABLE 4

| Peptide sequence | SEQ ID NO: |
| --- | --- |
| NH$_2$-NFGSVQVF-COOH | 20 |
| NH$_2$-NFGSVQ-COOH | 21 |
| NH$_2$-NFGSV-COOH | 22 |
| NH$_2$-FGSVQ-COOH | 23 |
| NH$_2$-GSVQ-COOH | 24 |
| NH$_2$-FGSV-COOH | 25 |
| NH$_2$-NAGSVQ-COOH | 26 |

Results

Figure 15:
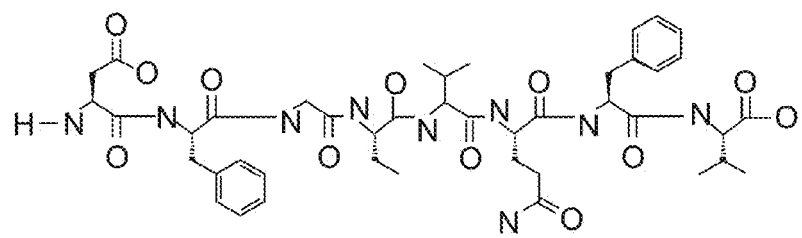
FIG. 15 is a chemical structure of a previously reported amyloidogenic peptide fragment of Medin [Haggqvist (1999) Proc. Natl. Acad. Sci. USA 96:8669-8674].

In order to get further insights into the structural elements of Medin that retain the molecular information needed to mediate a process of molecular recognition and self-assembly, the ability of short peptide fragments and analogues of Medin to form amyloid fibrils in vitro was studied. FIG. 15a shows a schematic representation of the chemical structure of the largest peptide fragment studied.

Example 13

Kinetics of Aggregation of Medin-Derived Peptide Fragments

Turbidity assay was effected as described in Example 8.

Figure 16A:
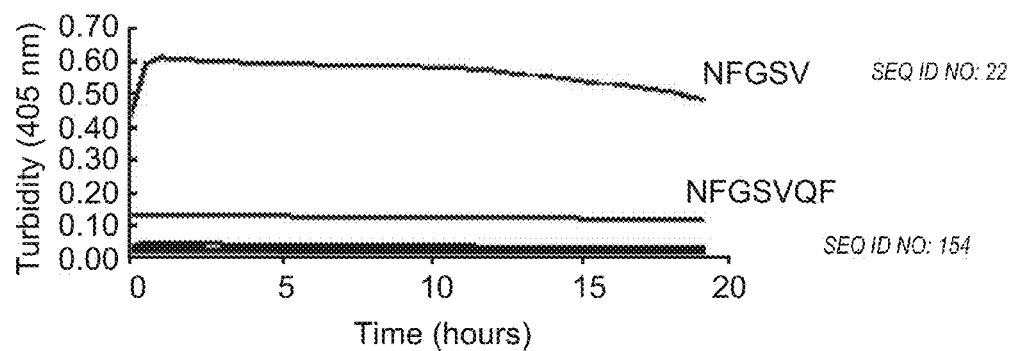
FIGS. 16a-b are graphs illustrating light absorbance at 405 nm as a function of time during fibril formation thus reflecting the aggregation kinetics of Medin-derived peptides.
Figure 16B:
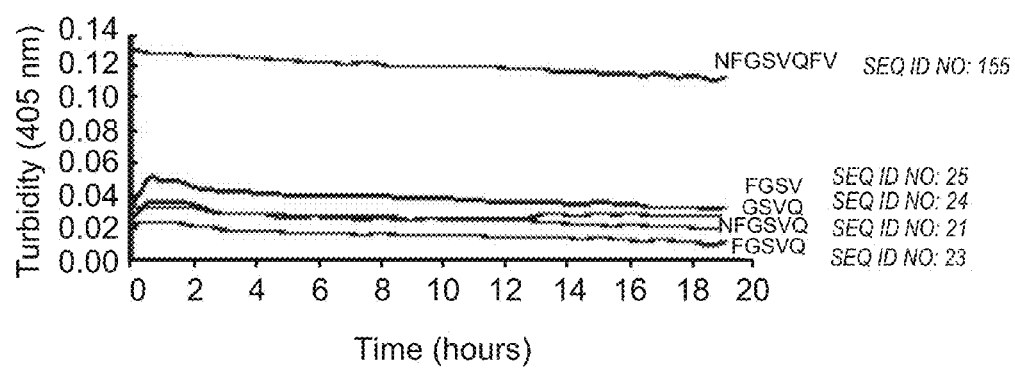

In order to get first insights regarding the aggregation potential of the various Medin derived peptides, turbidity assay was performed. Freshly made stocks of the amyloidogenic octapeptide and truncated analogues thereof were prepared in DMSO. The peptides were than diluted to aqueous solution and the turbidity was monitored by following the absorbance at 405 nm as a function of time. As shown in FIG. 16a, the NFGSV pentapeptide exhibited the highest degree of aggregation within minutes of incubation. Physical examination of the solution indicated that the peptide formed a gel structure. The kinetics of aggregation of the NFGSVQV octapeptide was too fast to be measured since turbidity was already observed immediately with the dilution into aqueous solution (FIGS. 16a-b). Similar fast kinetics were also observed with the GSVQ tetrapeptide. The truncated NFGSVQ, FGSVQ, and FGSV peptides showed a gradual increase in turbidity over ~30 minutes (FIG. 16b) which was followed by a slight decrease, which could be explained by sedimentation of large aggregates. Altogether, such kinetics and turbidity values were similar to those previously observed with amyloidogenic peptides of similar size (Azriel and Gazit, 2001).

Example 14

Ultrastructural Analysis of Medin-Derived Peptide Fragments

Electron microscopy analysis was effected as described in Example 10.

Figure 17A:
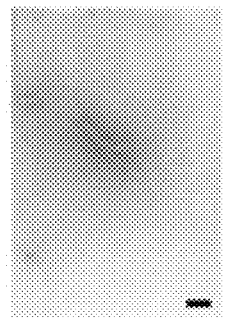
FIGS. 17a-f are electron micrographs of "aged" Medin-derived peptides. NFGSVQFA—FIG. 17a, NFGSVQ—FIG. 17b, NFGSV—FIG. 17c, FGSVQ—FIG. 17d, GSVQ—FIG. 17e and FGSV—FIG. 17f. The indicated scale bar represents 100 nm.
Figure 17B:
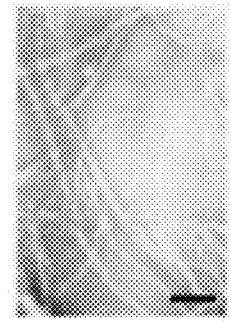
Figure 17C:
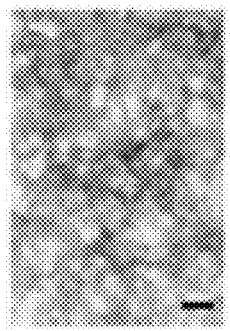
Figure 17D:
Figure 17E:
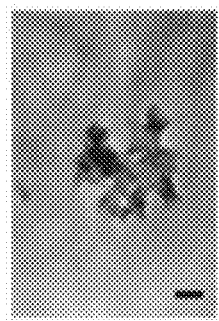
Figure 17F:
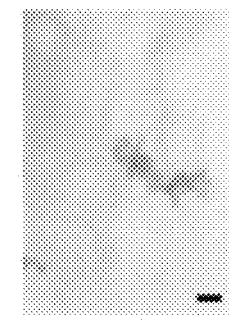

The fibrillization potential of Medin-derived peptide fragments was effected by electron microscopy (EM) using negative staining. Stock solutions of the peptide fragments were suspended and aged for 4 days. Fibrillar structures were clearly seen in solutions that contained both the NFGSVQFA octapeptide (FIG. 17a) and the truncated NFGSVQ (FIG. 17b). In both cases the structures were similar to those observed with much longer polypeptides, such the IAPP and the β-amyloid (Aβ) polypeptides. The shorter gel-forming NFGSV pentapeptide did not form a typical amyloid structure but a network of fibrous structures (FIG. 17c). It should be noted that fibrous networks were recently observed upon the gelation of the glutathione peptide [Lyon and Atkins, (2001) J. Am. Chem. Soc. 123:4408-4413]. No typical fibrils could be detected in solutions that contained the FGSVQ pentapeptide, the GSVQ tetrapeptide, or the FGSV tetrapeptide in spite of extensive search. While in the case of the FGSVQ peptide (FIG. 17d) somewhat fibrillar and ordered structure could be seen, although significantly different than those formed by typical amyloidogenic peptide), in the case of the GSVQ and the FGSV peptides, no fibrillar structures could be found (FIGS. 17e and 17f, respectively).

Example 15

Examination of Amyloidogenic Performance of Medin-Derived Peptides Through Congo Red (CR) Binding Assay CR staining was effected as described in Example 9.

A CR staining was effected to determine whether the structures formed by the various Medin-derived peptides show a typical birefringence. As shown in FIG. 18b, the NFGSVQ hexapeptide bound CR and exhibited a characteristic bright and strong green-gold birefringence. The NFGSVQFV octapeptide also exhibited significant birefringence (FIG. 18a), although less typical than that observed with the hexapeptide. The gel-forming NFGSV peptide deposits exhibited very low degree of birefringence (FIG. 18c). The FGSVQ and FGSV peptide showed no birefringence upon staining with CR (FIGS. 18d and 18f, respectively). There was clearly no significant difference between those two peptides and a negative control (i.e., buffer solution with no peptide) Interestingly, unexpected high level of birefringence was observed with the GSVQ tetrapeptide (FIG. 18e), while the morphology of the structures formed therefrom (FIG. 18e) was clearly different from that of amyloid fibrils, indicating that these structures may have a significant degree of order that is reflected in strong birefringence.

Example 16

The Effect of Phenylalanine Substitution on the Self-Assembly of Medin

T elucidate a possible role for the phenylalanine residue in the process of amyloid fibrils formation by the minimal amyloid-forming hexapeptide, the phenylalanine amino acids was replaced with an alanine. The alanine-substituted peptide was prepared and examined in the same way as described for the various fragments of Medin. As shown in FIG. 19a, a significantly lower turbidity was observed with the alanine-substituted peptide as compared to the wild-type hexapeptide. When aged solution of the NAGSVQ peptide was visualized by EM, no clear fibrillar structures could be detected (FIG. 19b). This is in complete contrast to the high abundance fibrillar structures seen with the wild-type peptide (FIG. 17b). Furthermore, the structures that were visualized did not show any degree of order as observed with the NFGSV and FGSVQ peptides as described above, FIGS. 17c-d, but were very similar to the completely non-fibrillar structures as were observed with the FGSV tetrapeptide (FIG. 17e). Interestingly, some degree of birefringence could still be detected (FIG. 19c) with the alanine-substituted peptide (as was observed with the GSVQ peptide, FIG. 18e). These results raise further doubts regarding the use of CR staining as a sole indicator of amyloid formation [Khurana (2001) J. Biol. Chem. 276:22715-22721].

Altogether these results show that the truncated fragment of Medin which is capable of forming amyloid fibrils is the hexapeptide NFGSVQ (SEQ ID NO: 21), although a shorter pentapeptide fragment, NFGSV (SEQ ID NO: 22), exhibited a network of fibrous structures which were not typical of amyloids. The amyloid forming NFGSVQ hexapeptide is noticeably similar to the minimal amyloidogenic fragment of the islet amyloid polypeptide (IAPP, see Examples 1-5). Taken together, the results are consistent with the assumed role of stacking interactions in the self-assembly processes that lead to the formation of amyloid fibrils and the suggested correlation between amyloid fibrils and β-helix structures.

Example 17

Identification of the Minimal Amyloidogenic Peptide Fragment of Human Calcitonin Human Calcitonin (hCT, GenBank Accession No. gi:179880) is a 32 amino acid long polypeptide hormone that is being produced by the C-cells of the thyroid and is involve in calcium homeostasis [Austin and Health (1981) N. Engl. J. Med. 304:269-278; Copp (1970) Annu. Rev. Physiol. 32:61-86; Zaidi (2002) Bone 30:655-663]. Amyloid fibrils composed of hCT were found to be associated with medullary carcinoma of the thyroid [Kedar (1976) Isr. J. Sci. 12:1137; Berger (1988) Arch. A. Pathol. Anat. Histopathol. 412:543-551; Arvinte (1993) J. Biol. Chem. 268:6415-6422]. Interestingly, synthetic hCT was found to form amyloid fibrils in vitro with similar morphology to the deposits found in the thyroid [Kedar (1976) Supra; Berger (1988) Supra; Arvinte (1993) Supra; Benvenga (1994) J. Endocrinol. Invest. 17:119-122; Bauer (1994) Biochemistry 33:12276-12282; Kanaori (1995) Biochemistry 34:12138-43; Kamihara (2000) Protein Sci. 9:867-877]. The in vitro process of amyloid formation is affected by the pH of the medium [23]. Electron microscopy experiments have revealed that the fibrils formed by hCT are approximately 80 Å in diameter and up to several micrometers in length. The fibrils are often associated with one another and in vitro amyloid formation is affected by the pH of the medium [Kamihara (2000) Supra.].

Calcitonin has been used as a drug for various diseases including Paget's disease and osteoporosis. However, the tendency of hCT to associate and form amyloid fibrils in aqueous solutions at physiological pH is a significant limit for its efficient use as a drug [Austin (1981) Supra; Copp (1970)

Supra; Zaidi (2002) Supra]. Salmon CT [Zaidi (2002) Supra], the clinically used alternative to hCT, causes immunogenic reaction in treated patients due to low sequence homology. Therefore, understanding the mechanism of amyloid formation by hCT and controlling this process is highly important not only in the context of amyloid formation mechanism but also as a step toward improved therapeutic use of Calcitonin.

Circular dichroism (CD) studies have shown that in water monomeric hCT has little ordered secondary structure at room temperature [Arvinte (1993) Supra]. However, studies of hCT fibrils using circular dichroism, fluorescence, and infrared spectroscopy revealed that fibrillated hCT molecules have both α-helical and β-sheet secondary structure components [Bauer (1994) Supra]. NMR spectroscopy studies have shown that in various structure promoting solvents like TFE/$H_2O$, hCT adopts an amphiphilic α-helical conformation, predominantly in the residue range 8-22 [Meadows (1991) Biochemistry 30:1247-1254; Motta (1991) Biochemistry 30:10444-10450]. In DMSO/$H_2O$, a short double-stranded antiparallel β-sheet form in the central region made by residues 16-21 [Motta (1991) Biochemistry 30:2364-71].

Based on this structural data and the proposed role of aromatic residues in the process of amyloid formation, the present inventor has identified a short peptide fragment, which is sufficient for mediating Calcitonin self-assembly [Reches (2002) J. Biol. Chem. 277:35475-80].

The Studied Peptides—Based on the previously reported susceptibility of amyloid formation to acidic pH [Kanaori (1995) Supra], it was suggested that negatively-charged amino-acids, which undergo protonation at low pH, may play a key role in the process of amyloid formation. The only negatively-charged amino-acid in hCT is $Asp^{15}$ (FIG. 20a). Furthermore, a critical role for residues $Lys^{18}$ and $Phe^{19}$ in the oligomerization state and bioactivity of hCT was recently shown [Kazantzis (269) Eur. J. Biochem. 269:780-91]. Together with the occurrence of two phenylalanine residues in the region focused the structural analysis of the amyloidogenic determinants in hCT to amino acids 15-19. FIG. 20b shows a schematic representation of the chemical structure of the longest peptide and Table 5 below, indicates the various peptide fragments that were used in the study.

TABLE 5

| Amino acid coordinates on hCT | Peptide sequence | SEQ ID NO: |
|---|---|---|
| 15-19 | $NH_2$-DFNKF-COOH | 27 |
| 16-19 | $NH_2$-FNKF-COOH | 28 |
| 15-18 | $NH_2$-DFNK-COOH | 29 |
| 15-17 | $NH_2$-DFN-COOH | 30 |
| F > A 15-19 | $NH_2$-DANKF-COOH | 31 |

Example 18

Ultrastructural Analysis of Calcitonin-Derived Peptide Fragments

Electron microscopy analysis was effected as described in Example 10.

The fibrillization potential of Calcitonin-derived peptide fragments was effected by electron microscopy (EM) using negative staining. Stock solutions of the peptide fragments were suspended in 0.02M NaCl, 0.01M Tris pH 7.2, aged for 2 days and negatively stained. Fibrillar structures, similar to those formed by the full-length polypeptide [Arvinte (1993) Supra; Benvenga (1994) Supra; Bauer (1994) Supra; Kanaori (1995) Supra; Kamihara (2000) Supra], were clearly seen with high frequency in solutions that contained the DFNKF pentapeptide (FIG. 21a). The shorter DFNK tetrapeptide also formed fibrillar structures (FIG. 21b). However, the structures formed were less ordered as compared to those formed by the DFNKF pentapeptide. The amount of fibrillar structures formed by DFNK was also lower as compared to the DFNKF peptapeptide. No clear fibrils could be detected using solutions that contained the FNKF tetrapeptide and the DFN tripeptide, in spite of extensive search. In the case of the FNKF tetrapeptide only amorphous aggregates could be found (FIG. 21c). The DFN tripeptide formed more ordered structures (FIG. 21d) that resembled the structure formed by gel-forming tripeptide [Lyon (2001) Supra]. To study whether the FNKF tetrapeptide and the DFN tripeptide peptide cannot form fibrils whatsoever or the observation is a result of slow kinetics, a solution of the peptides at the same experimental conditions was incubated for two weeks. Also in this case no clear fibrillar structures could be detected (data not shown).

Example 19

Examination of Amyloidogenic Performance of Calcitonin13 Derived Peptides Through Congo Red (CR) Binding Assay CR staining was effected as described in Example 9.

Figure 22A:
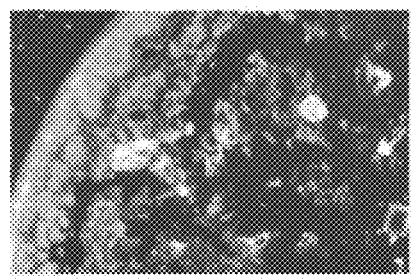
FIGS. 22a-d are photomicrographs illustrating Congo Red binding to pre-assembled Calcitonin-derived peptides. Polarized field micrographs are shown for each of the following aged peptide suspensions: DFNKF—FIG. 22a, DFNK—FIG. 22b, FNKF—FIG. 22c and DFN—FIG. 22d.
Figure 22B:
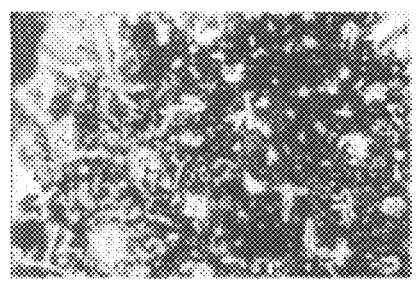
Figure 22C:
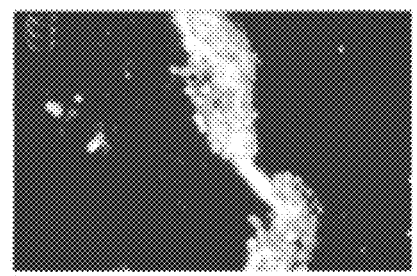
Figure 22D:
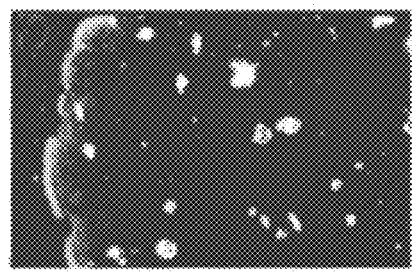

A CR staining was effected to determine whether the structures formed by the various hCT-derived peptides show a typical birefringence. As shown in FIGS. 22a-d, all the studies peptides showed some degree of birefringence. However, the green birefringence, which was observed with the DFNKF-pentapeptide was clear and strong (FIG. 22a). The level of birefringence that was observed with the other peptides was lower but significant since no birefringence could be detected using control solutions which did not contain the peptides. The lower level of birefringence of the DFNK tetrapeptide (FIG. 22b) was consistent with the lower extent of fibrillization as observed using EM (FIG. 21b). It will be appreciated, though, that the birefringence observed with the FNKF tetrapeptide and the DFN tripeptide might represent some degree of ordered structures [Lyon (2001) Supra].

Example 20

Secondary Structure of the Aggregated hCT—Derived Peptides

FT-IR spectroscopy was effected as described in Example 11.

Figure 23:
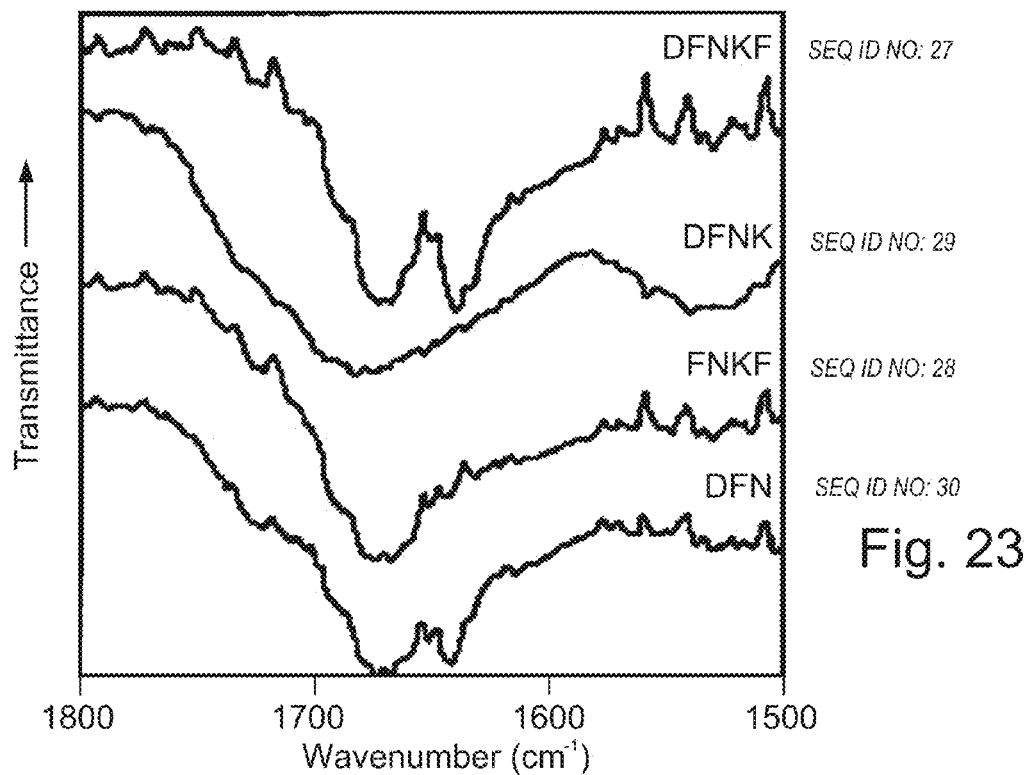
FIG. 23 is a graphic illustration showing secondary structures in the insoluble Calcitonin aggregates as determined by Fourier transformed infrared spectroscopy.

Amyloid deposits are characteristic of fibrils rich with β-pleated sheet structures. To get a quantitative information regarding the secondary structures that were formed by the various peptide fragments FT-IR spectroscopy was used. Aged peptide solutions were dried on $CaF_2$ plates forming thin films as described in Example 11. As shown in FIG. 23, the DFNKF pentapeptide exhibited a double minima (at 1639 $cm^{-1}$ and 1669 $cm^{-1}$) an amide I FT-IR spectrum that is consistent with anti-parallel β-sheet structure and is remarkably similar to the spectrum of the amyloid-forming hexapeptide fragment of the islet amyloid polypeptide [Tenidis (2000) Supra]. The amide I spectrum observed with the DFNK tetrapeptide (FIG. 23) was less typical of a β-sheet structure. While it exhibited a minimum at 1666 cm$^{-1}$ that may reflect an anti-parallel β-sheet it lacked the typical minimum around 1620-1640 cm$^{-1}$ that is typically observed with β-sheet structures. The FNKF tetrapeptide exhibited a FT-IR spectrum that is typical of a non-ordered structure (FIG. 23) and is similar to spectra of the short non-amyloidogenic fragments of the islet amyloid polypeptide [Tenidis (2000) Supra]. The DFN tripeptide exhibited a double minima (at 1642 cm$^{-1}$ and 1673 cm$^{-1}$, FIG. 23) amide I FT-IR spectrum that is consistent with a mixture of β-sheet and random structures. This may further indicate that the structures observed by EM visualization may represent some degree of ordered structure composed of predominantly β-sheet structural elements.

Example 21

Figure 24A:
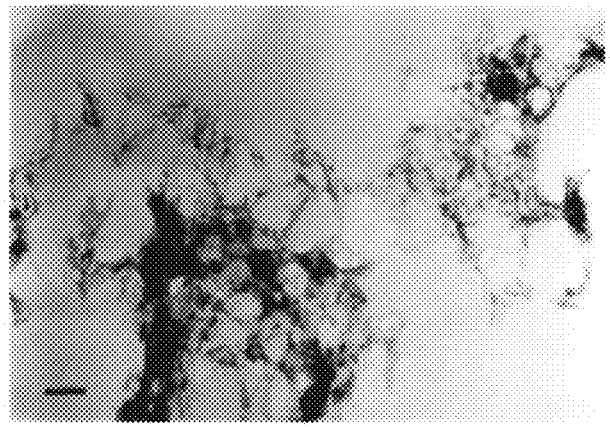
FIGS. 24a-c depict the effect an alanine mutation on the amyloidogenic features of the pentapeptide amyloidogenic fragment of Calcitonin.
Figure 24B:
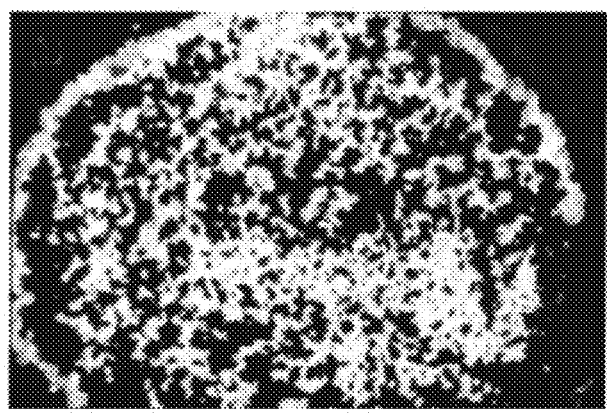
Figure 24C:
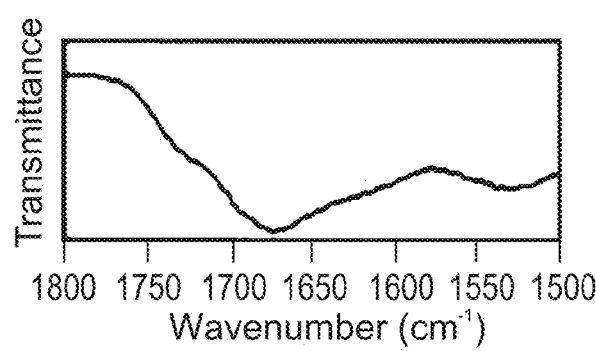

The Effect of Phenylalanine Substitution on the Self-Assembly of Calcitonin-Derived Peptides In order to get insight into a possible role for the phenylalanine residues in the process of Calcitonin self-assembly, the phenylalanine amino acids were replaced with alanine in the context of the pentapeptide (SEQ ID NO: 31). When aged solution of the DANKF pentapeptide was visualized by EM, no clear fibrillar structures could be detected (FIG. 24a). Structures that were visualized exhibited some degree of order (as compared to the amorphous aggregates seen with the FNKF tetrapeptide), however, no green-gold birefringence could be observed (FIG. 24b). The FT-IR spectrum of the DANKF pentapeptide was similar to that of the FNKF tetrapeptide and other short non-amyloidogenic peptide, typical of non-ordered structures [Tenidis (2000) Supra]. Taken together, the effect of the phenylalanine to alanine substitution is very similar to the effect of such a change in the context of a short amyloid-forming fragment of the islet amyloid polypeptide [Azriel (2001) Supra].

Altogether, the ability of an hCT-derived pentapeptide (SEQ ID NO: 27) to form well-ordered amyloid fibrils was demonstrated. The typical fibrillar structure as seen by electron microscopy visualization (FIG. 21a), the very strong green birefringence upon staining with CR (FIG. 22a), and the typical anti-parallel β-sheet structure (FIG. 23a), all indicate that the DFNKF pentapeptide is a very potent amyloid forming agent. Other pentapeptides capable of self-assembling were shown in hereinabove. Yet, in terms of the degree of birefringence and electron microscopy morphology, the hCT fragment seems to be the pentapeptide with the highest amyloidogenic potential similar to the potent amyloidogenic fragment of the 13-amyloid (Aβ) polypeptide, KLVFFAE [Balbach (2000) Biochemistry 39:13748-59]. It is possible that electrostatic interactions between the opposing charges on the lysine and aspartic acids direct the formation of ordered antiparallel structure. Interestingly, the DFNK polypeptide exhibited a significantly lower amyloidogenic potential as compared to the DFNKF peptide. It is possible that a pentapeptide is a lower limit for potent amyloid former. This is consistent with recent results that demonstrate that two pentapeptides of IAPP, NFLVH and FLVHS, can form amyloid fibrils, but their common denominator, the tetrapeptide FLVH, could not form such fibrils (see Examples 1-5).

Example 22

Identification of an Amyloidogenic Peptide from Lactotransferrin

Amyloid fibril formation by lactotransferrin (GenBank Accession No. gi:24895280) is associated familial subepithelial corneal amyloid formation [Sacchettini and Kelly (2002) Nat Rev Drug Discov 1:267-75]. Based on the proposed role of aromatic residues in amyloid self-assembly, the amyloidogenic features of a Lactotransferrin-derived peptide, LFNQTG (SEQ ID NO: 32) were studied.

Materials and Experimental Procedures—Described in Examples 7 and 10.

Figure 25:
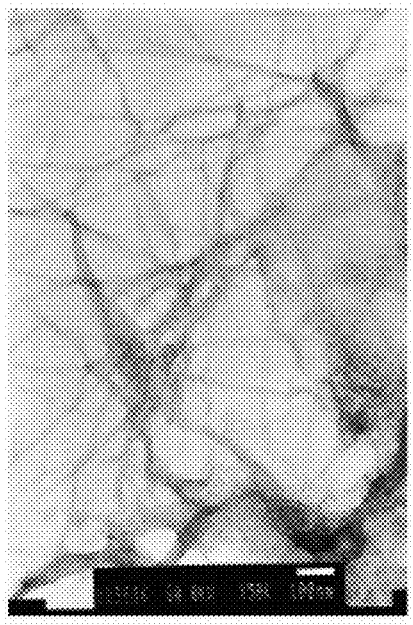
FIG. 25 is an electron micrograph depicting self-assembly of "aged" Lactotransferrin-derived peptide. The scale bar represents 100 nm.

Results—To characterize the ability of the Lactotransferrin-derived peptide to form fibrilar supramolecular ultrastructures, negative staining electron microscopy analysis was effected. As shown in FIG. 25, under mild conditions, filamentous structures were observed for the selected peptide, suggesting that LFNQTG of Lactotransferrin is important for the polypeptide self-assembly. These results further substantiate the ability of the present invention to predict amyloidogenic peptide sequences.

Example 23

Identification of an Amyloidogenic Peptide from Serum Amyloid a Protein

Fragments of Serum amyloid A proteins (GenBank Accession No. gi:134167) were found in amyloid-state in cases of Chronic inflammation amyloidosis (Westermark et al. (1992) Biochem. Biophys. Res. Commun. 182: 27-33). Based on the proposed role of aromatic residues in amyloid self-assembly, the amyloidogenic features of a Serum amyloid A protein-derived peptide, SFFSFL (SEQ ID NO: 33) were studied.

Materials and Experimental Procedures—Described in Examples 7 and 10.

Figure 26:
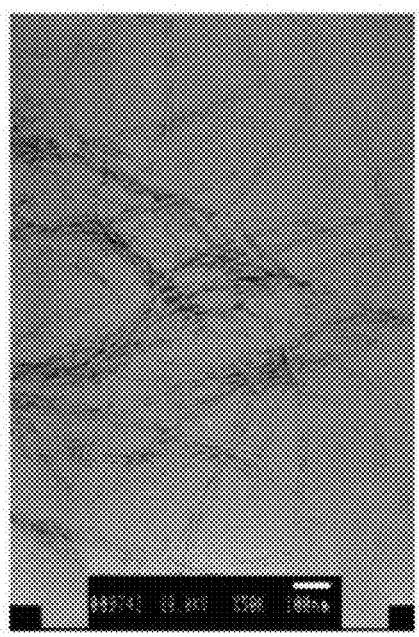
FIG. 26 is an electron micrograph depicting self-assembly of "aged" Serum amyloid A protein-derived peptide. The scale bar represents 100 nm.

Results—To characterize the ability of the Serum amyloid A protein-derived peptide to form fibrilar supramolecular ultrastructures, negative staining electron microscopy analysis was effected. As shown in FIG. 26, under mild conditions, filamentous structures were observed for the selected peptide, suggesting that SFFSFL of serum amyloid A protein is important for the polypeptide self-assembly. These results further substantiate the ability of the present invention to predict amyloidogenic peptide sequences.

Example 24

Identification of an Amyloidogenic Peptide from BriL

The human BRI gene is located on chromosome 13. The amyloid fibrils of the BriL gene product (GenBank Accession No. gi:12643343) are associated with neuronal dysfunction and dementia (Vidal et al (1999) Nature 399, 776-781). Based on the proposed role of aromatic residues in amyloid self-assembly, the amyloidogenic features of a BriL-derived peptide, FENKF (SEQ ID NO: 34) were studied.

Materials and Experimental Procedures—Described in Examples 7 and 10.

Figure 27:
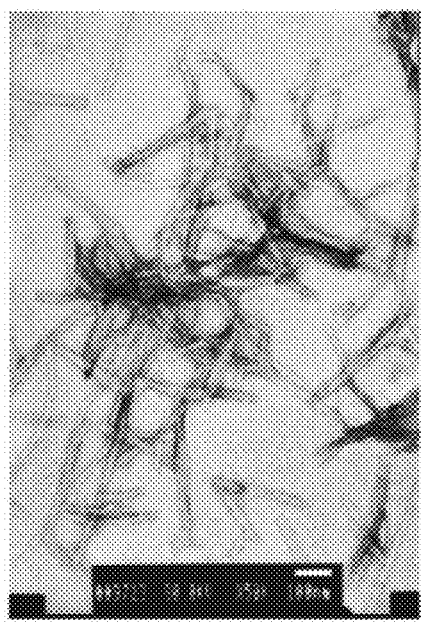
FIG. 27 is an electron micrograph depicting self-assembly of "aged" BriL-derived peptide. The scale bar represents 100 nm.

Results—To characterize the ability of the BriL-derived peptide to form fibrilar supramolecular ultrastructures, negative staining electron microscopy analysis was effected. As shown in FIG. 27, under mild conditions, filamentous structures were observed for the selected peptide, suggesting that FENKF of BriL is important for the polypeptide self-assembly. These results further substantiate the ability of the present invention to predict amyloidogenic peptide sequences.

Example 25

Identification of an Amyloidogenic Peptide from Gelsolin

Fragments of Gelsolin proteins (GenBank Accession No. gi:4504165) were found in amyloid-state in cases of Finnish hereditary amyloidosis [Maury and Nurmiaho-Lassila (1992) Biochem. Biophys. Res. Commun. 183: 227-31]. Based on the proposed role of aromatic residues in amyloid self-assembly, the amyloidogenic features of a Gelsolin-derived peptide, SFNNG (SEQ ID NO: 35) were studied.

Materials and Experimental Procedures—Described in Examples 7 and 10.

Figure 28:
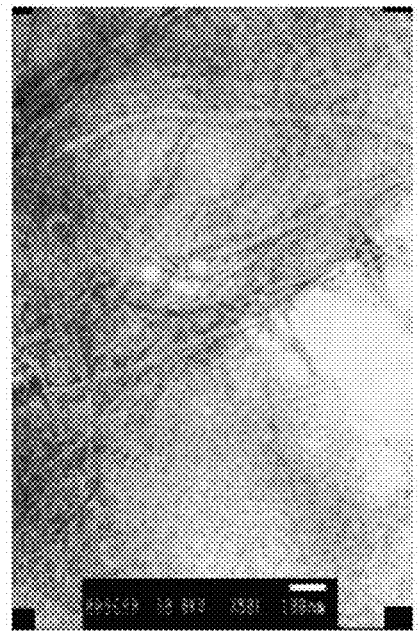
FIG. 28 is an electron micrograph depicting self-assembly of "aged" Gelsolin-derived peptide. The scale bar represents 100 nm.

Results—To characterize the ability of the Gelsolin-derived peptide to form fibrilar supramolecular ultrastructures, negative staining electron microscopy analysis was effected. As shown in FIG. 28, under mild conditions, filamentous structures were observed for the selected peptide, suggesting that SFNNG of BriL is important for the polypeptide self-assembly. These results further substantiate the ability of the present invention to predict amyloidogenic peptide sequences.

Example 26

Identification of an Amyloidogenic Peptide from Serum Amyloid P

Amyloid fibril formation by beta-amyloid is promoted by interaction with serum amyloid-P (GenBank Accession No. gi:2144884). Based on the proposed role of aromatic residues in amyloid self-assembly, the amyloidogenic features of a Serum amyloid P-derived peptide, LQNFTL (SEQ ID NO: 36) were studied.

Materials and Experimental Procedures—Described in Examples 7 and 10.

Figure 29:
FIG. 29 is an electron micrograph depicting self-assembly of "aged" Serum amyloid P-derived peptide. The scale bar represents 100 nm.

Results—To characterize the ability of the Serum amyloid P-derived peptide to form fibrilar supramolecular ultrastructures, negative staining electron microscopy analysis was effected. As shown in FIG. 29, under mild conditions, filamentous structures were observed for the selected peptide, suggesting that LQNFTL of Serum amyloid P is important for the polypeptide self-assembly. These results further substantiate the ability of the present invention to predict amyloidogenic peptide sequences.

Example 27

Identification of an Amyloidogenic Peptide from Immunoglobulin Light Chain

Amyloid fibrils formation by Immunoglobulin light chain (GenBank Accession No. gi:625508) is associated with primary systemic amyloidosis [Sacchettini and Kelly (2002) Nat Rev Drug Discov 1:267-75]. Based on the proposed role of aromatic residues in amyloid self-assembly, the amyloidogenic features of an Immunoglobulin light chain-derived peptide, TLIFGG (SEQ ID NO: 37) were studied.

Materials and Experimental Procedures—Described in Examples 7 and 10.

Figure 30:
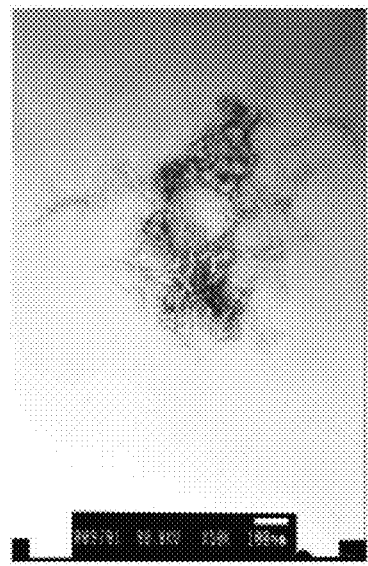
FIG. 30 is an electron micrograph depicting self-assembly of "aged" Immunoglobulin light chain-derived peptide. The scale bar represents 100 nm.

Results—To characterize the ability of the immunoglobulins light chain-derived peptide to form fibrilar supramolecular ultrastructures, negative staining electron microscopy analysis was effected. As shown in FIG. 30, under mild conditions, filamentous structures were observed for the selected peptide, suggesting that TLIFGG of the immunoglobulin light chain is important for the polypeptide self-assembly. These results further substantiate the ability of the present invention to predict amyloidogenic peptide sequences.

Example 28

Identification of an Amyloidogenic Peptide from Cystatin C

Amyloid fibril formation by Cystatin C (GenBank Accession No. gi:4490944) is associated with hereditary cerebral amyloid angiopathy [Sacchettini and Kelly (2002) Nat Rev Drug Discov 1:267-75]. Based on the proposed role of aromatic residues in amyloid self-assembly, the amyloidogenic features of a Cystatin C-derived peptide, RALDFA (SEQ ID NO: 38) were studied.

Materials and Experimental Procedures—Described in Examples 7 and 10.

Figure 31:
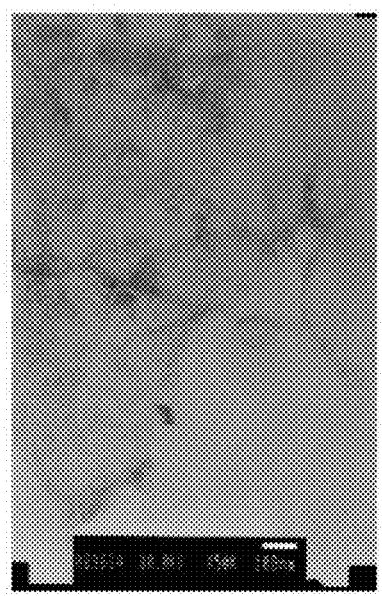
FIG. 31 is an electron micrograph depicting self-assembly of "aged" Cystatin C-derived peptide. The scale bar represents 100 nm.

Results—To characterize the ability of the Cystatin C-derived peptide to form fibrilar supramolecular ultrastructures, negative staining electron microscopy analysis was effected. As shown in FIG. 31, under mild conditions, filamentous structures were observed for the selected peptide, suggesting that RALDFA of the Cystatin C is important for the polypeptide self-assembly. These results further substantiate the ability of the present invention to predict amyloidogenic peptide sequences.

Example 29

Identification of an Amyloidogenic Peptide from Transthyretin

Amyloid fibril formation by Transthyretin (GenBank Accession No. gi:72095) is associated with familial amyloid polyneuropathy (Sacchettini and Kelly (2002) Nat Rev Drug Discov 1:267-75). Based on the proposed role of aromatic residues in amyloid self-assembly, the amyloidogenic features of an Transthyretin-derived peptide, GLVFVS (SEQ ID NO: 39) were studied.

Materials and Experimental Procedures—Described in Examples 7 and 10.

Figure 32:
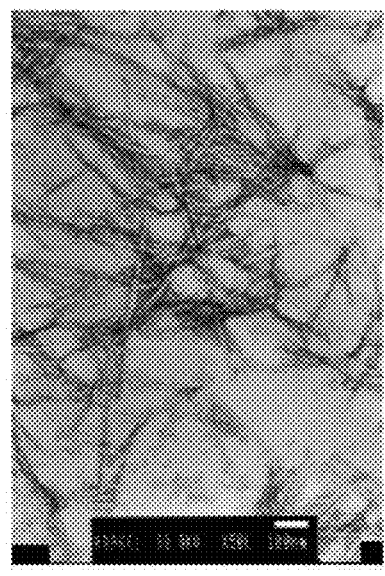
FIG. 32 is an electron micrograph depicting self-assembly of "aged" Transthyretin-derived peptide. The scale bar represents 100 nm.

Results—To characterize the ability of the Transthyretin-derived peptide to form fibrilar supramolecular ultrastructures, negative staining electron microscopy analysis was effected. As shown in FIG. 32, under mild conditions, filamentous structures were observed for the selected peptide, suggesting that GLVFVS of Transthyretin is important for the polypeptide self-assembly. These results further substantiate the ability of the present invention to predict amyloidogenic peptide sequences.

Example 30

Identification of an Amyloidogenic Peptide from Lysozyme

Amyloid fibril formation by Lysozyme (GenBank Accession No. gi:299033) is associated with familial non-neuropathic amyloidosis [Sacchettini and Kelly (2002) Nat Rev Drug Discov 1:267-75]. Based on the proposed role of aromatic residues in amyloid self-assembly, the amyloidogenic features of a Lysozyme-derived peptide, GTFQIN (SEQ ID NO: 40) were studied.

Materials and Experimental Procedures—Described in Examples 7 and 10.

Figure 33:
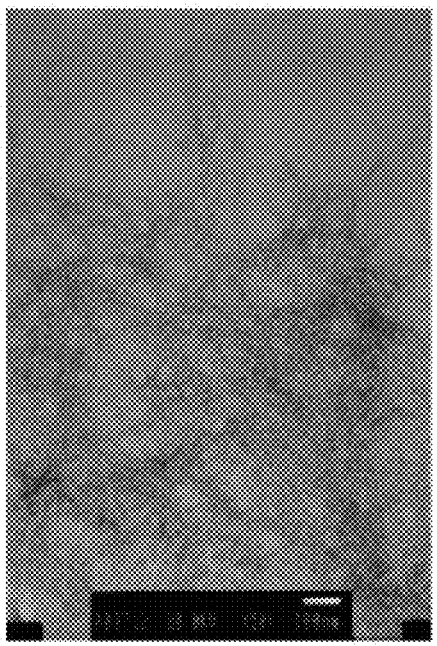
FIG. 33 is an electron micrograph depicting self-assembly of "aged" Lysozyme-derived peptide. The scale bar represents 100 nm.

Results—To characterize the ability of the Lysozyme-derived peptide to form fibrilar supramolecular ultrastructures, negative staining electron microscopy analysis was effected. As shown in FIG. 33, under mild conditions, filamentous structures were observed for the selected peptide, suggesting that GTFQIN of Lysozyme is important for the polypeptide self-assembly. These results further substantiate the ability of the present invention to predict amyloidogenic peptide sequences.

Example 31

Identification of an Amyloidogenic Peptide from Fibrinogen

Amyloid fibril formation by Fibrinogen (GenBank Accession No. gi:11761629) is associated with hereditary renal amyloidosis (Sacchettini and Kelly (2002) Nat Rev Drug Discov 1:267-75). Based on the proposed role of aromatic residues in amyloid self-assembly, the amyloidogenic features of a Fibrinogen-derived peptide, SGIFTN (SEQ ID NO: 41) were studied.

Materials and Experimental Procedures—Described in Examples 7 and 10.

Figure 34:
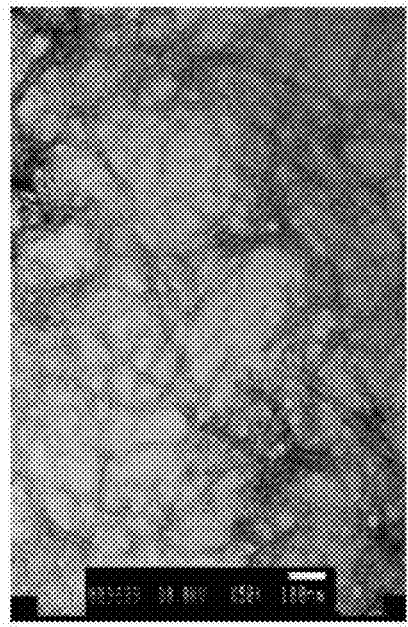
FIG. 34 is an electron micrograph depicting self-assembly of "aged" Fibrinogen-derived peptide. The scale bar represents 100 nm.

Results—To characterize the ability of the Fibrinogen-derived peptide to form fibrilar supramolecular ultrastructures, negative staining electron microscopy analysis was effected. As shown in FIG. 34, under mild conditions, filamentous structures were observed for the selected peptide, suggesting that SGIFTN of Fibrinogen is important for the polypeptide self-assembly. These results further substantiate the ability of the present invention to predict amyloidogenic peptide sequences.

Example 32

Identification of an Amyloidogenic Peptide from Insulin

Amyloid fibril formation by Insulin (GenBank Accession No. gi:229122) is associated with injection-localized amyloidosis [Sacchettini and Kelly (2002) Nat Rev Drug Discov 1:267-75]. Based on the proposed role of aromatic residues in amyloid self-assembly, the amyloidogenic features of an insulin-derived peptide, ERGFF (SEQ ID NO: 42) were studied.

Materials and Experimental Procedures—Described in Examples 7 and 10.

Figure 35:
FIG. 35 is an electron micrograph depicting self-assembly of "aged" Insulin-derived peptide. The scale bar represents 100 nm.

Results—To characterize the ability of the Insulin-derived peptide to form fibrilar supramolecular ultrastructures, negative staining electron microscopy analysis was effected. As shown in FIG. 35, under mild conditions, filamentous structures were observed for the selected peptide, suggesting that ERGFF of insulin is important for the polypeptide self-assembly. These results further substantiate the ability of the present invention to predict amyloidogenic peptide sequences.

Example 33

Identification of an Amyloidogenic Peptide from Prolactin

Amyloid fibrils formation by prolactin (GenBank Accession No. gi:4506105) is associated with pituitary-gland amyloidosis (Sacchettini and Kelly (2002) Nat Rev Drug Discov 1:267-75). Based on the proposed role of aromatic residues in amyloid self-assembly, the amyloidogenic features of a prolactin-derived peptide, RDFLDR (SEQ ID NO: 43) were studied.

Materials and Experimental Procedures—Described in Examples 7 and 10.

Figure 36:
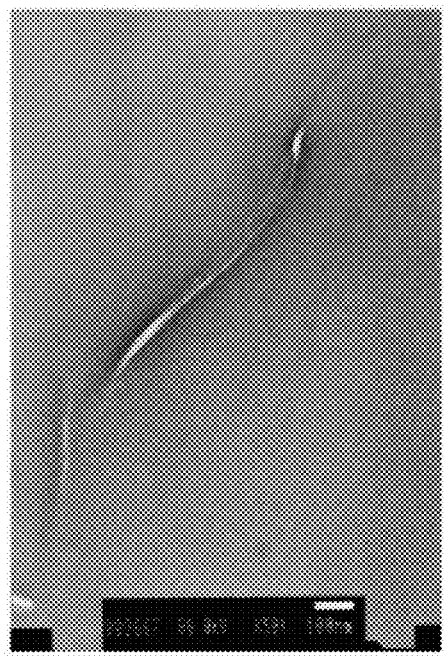
FIG. 36 is an electron micrograph depicting self-assembly of "aged" Prolactin-derived peptide. The scale bar represents 100 nm.

Results—To characterize the ability of the prolactin-derived peptide to form fibrilar supramolecular ultrastructures, negative staining electron microscopy analysis was effected. As shown in FIG. 36, under mild conditions, filamentous structures were observed for the selected peptide, suggesting that RDFLDR of prolactin is important for the polypeptide self-assembly. These results further substantiate the ability of the present invention to predict amyloidogenic peptide sequences.

Example 34

Identification of an Amyloidogenic Peptide from Beta-2-Microglobulin

Amyloid fibrils formation by beta-2-microtublin (GenBank Accession No. gi:70065) is associated haemodialysis-related amyloidosis (Sacchettini and Kelly (2002) Nat Rev Drug Discov 1:267-75). Based on the proposed role of aromatic residues in amyloid self-assembly, the amyloidogenic features of a beta-2-microtublin-derived peptide, SNFLN (SEQ ID NO: 44) were studied.

Materials and Experimental Procedures—Described in Examples 7 and 10.

Figure 37:
FIG. 37 is an electron micrograph depicting self-assembly of "aged" Beta 2 microglobulin-derived peptide. The scale bar represents 100 nm.

Results—To characterize the ability of the beta-2-microtublin-derived peptide to form fibrilar supramolecular ultrastructures, negative staining electron microscopy analysis was effected. As shown in FIG. 37, under mild conditions, filamentous structures were observed for the selected peptide, suggesting that SNFLN of beta-2-microtublin is important for the polypeptide self-assembly. These results further substantiate the ability of the present invention to predict amyloidogenic peptide sequences.

Example 35

Inhibition of Amyloid Formation an Amyloidogenic Peptide Identified According to the Teachings of the Present Invention The ability of amyloidogenic peptides of IAPP, identified according to the teachings of the present invention to inhibit amyloid formation by the full-length polypeptide was tested by the addition of beta-breaker proline residues to the recognition sequence as set forth in the peptide sequence NFLVHPP (SEQ ID NO: 45).

The degree of amyloid fibrils formation with and without the inhibitor was assessed using thioflavin T (ThT) as molecular indicator. The degree of fluorescence of the ThT dye is directly correlated with the amount of amyloid fibrils in the solution [LeVine H 3rd. (1993) Protein Sci. 2:404-410. IAPP solutions (4 μM hIAPPin 10 mM Tris buffer pH 7.2), were incubated in the presence or absence of 40 μM of the modified peptide (i.e., NFLVHPP) at room temperature. Fibril formation was determined by a ten fold dilution of the solutions into a solution that contained 3 μM thioflavin T (ThT) in 50 mM sodium phosphate pH 6.0 and determination of fluorescence at 480 nm with excitation at 450 nm using a LS50B spectroflurimeter (Perkin Elmar, Wellesley, Mass.). As a control 10 mM Tris buffer pH 7.2 were diluted into the ThT solution and fluorescence was determined as described.

Figure 38:
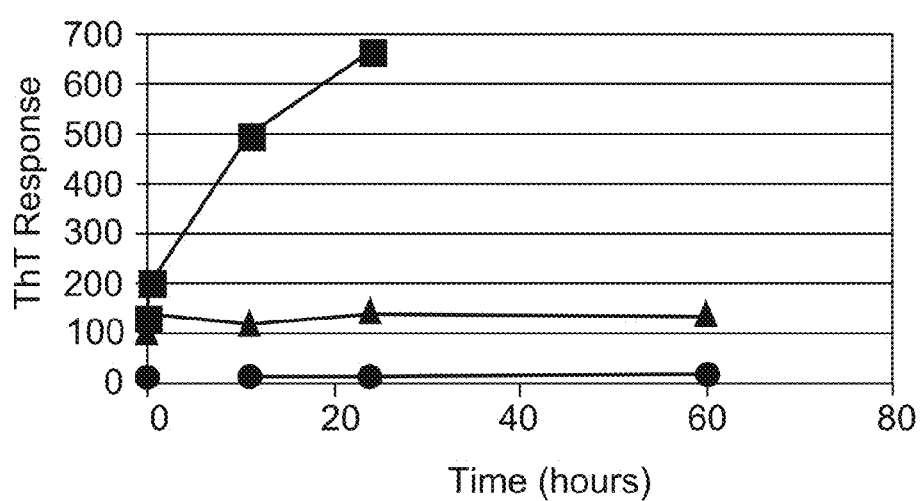
FIG. 38 is a graphic representation of the effect of an inhibitory peptide on IAPP self-assembly. Squares—wild type (wt) IAPP peptide; triangles—wt-IAPP+inhibitory peptide; circles—no peptides.

Result—As shown in FIG. 38, while the IAPP alone showed high levels of ThT fluorescence as expected for amyloidogenic protein, there was a significant increase in fluorescence in the presence of the inhibitory peptide. Thus, these results validate the NFLVH sequence as the amyloidogenic determinant in the IAPP polypeptide.

Example 36

Significance of Hydrophobic Residues in Amyloid Assembly

The significance of an aromatic residue in the basic amyloidogenic unit of IAPP has been demonstrated in Examples 1-5. As described, substitution of a phenylalanine to an alanine abolished the ability of an amyloidogenic fragment (NAGAIL, SEQ ID NO: 9) to form amyloid fibrils in vitro. Based on this observation, the remarkable occurrence of aromatic residues in other short amyloid related sequences (Examples 12-35), and the well-known role of π-stacking in processes of self-assembly in chemistry and biochemistry, it was suggested that stacking of aromatic residues may play a role in the process of amyloid fibrils formation [Gazit (2002) FASEB J. 16:77-83].

The study was further extended to indicate whether the phenylalanine residue is critical due to aromaticity thereof, or rather due to its hydrophobic nature. The effect of phenylalanine substitution with hydrophobic residues on the self assembly of the basic amyloidogenic unit of IAPP (i.e., NFGAIL peptide) was addressed.

The list of peptides used in the study and designation thereof is presented in Table 6, below.

TABLE 6

| Amino acid substitution and coordinates on hIAPP | Peptide sequence | SEQ ID NO: |
|---|---|---|
| WT 22-29 | NH$_2$-NFGAILSS-COOH | 46 |
| F > I 22-29 | NH$_2$-NIGAILSS-COOH | 47 |
| F > L 22-29 | NH$_2$-NLGAILSS-COOH | 48 |
| F > V 22-29 | NH$_2$-NVGAILSS-COOH | 49 |
| F > A 22-29 | NH$_2$-NAGAILSS-COOH | 89 |

It will be appreciated that while these hydrophobic amino acids are similar or even slightly more hydrophobic than phenylalanine [Wolfenden (1981) Biochemistry 20:849-855; Kyte (1982) J. Mol. Biol. 157:105-132; Radzicka (1988)], they are not aromatic. Furthermore, valine and isoleucine, are considered to be very strong β-sheet formers [Chou (1974) Biochemistry 13:211-222; Chou (1978) Annu. Rev. Biochem. 47:251-276], which is assumed to be important to the formation of β-sheet rich amyloid fibrils.

Example 37

Characterization of the Aggregation Kinetics of Hydrophobically Modified hIAPP Peptide Fragments as Monitored by Turbidity Measurements Experimental Procedures—Effected as described in Example 8.

Results

Figure 39:
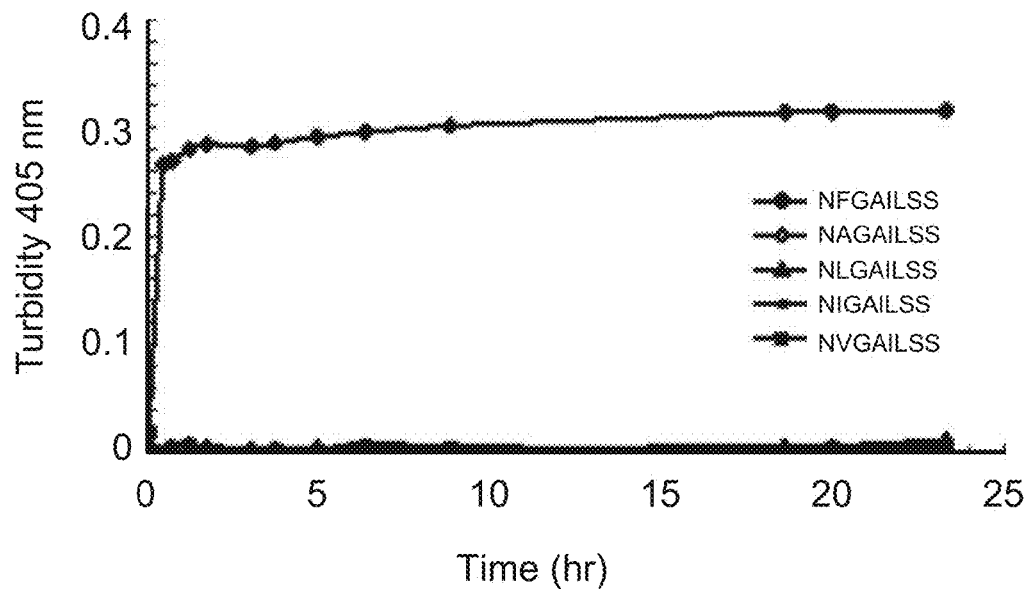
FIG. 39 is a graphic illustration depicting light absorbance at 405 nm as a function of time during fibril formation thus reflecting the aggregation kinetics of IAPP-derived peptides (SEQ ID NOs. 46-49, 89).

To get insight into the aggregation potential of the hydrophobically-modified IAPP-derived peptide analogues, turbidity assay was performed. Freshly made stock solutions of the wild-type peptide and the various peptide mutants were made in DMSO. The peptides were then diluted to a buffer solution and the turbidity was monitored by following the absorbance at 405 nm as a function of time. As shown in FIG. 39, significant increase in turbidity was observed for the wild-type NFGAILSS octapeptide within minutes following dilution thereof into the aqueous solution. The shape of the aggregation curve resembled that of a saturation curve, with a rapid increase in turbidity in the first hour, followed by a much slower increase in turbidity over the entire incubation time monitored. This probably reflects a rapid aggregation process, with the number of free building blocks as the rate limiting factor. In contrast, none of the analogue peptides revealed any significant aggregative behavior and the turbidity of all the hydrophobic analogues as well as the alanine-substituted analogues remained very low for at least 24 hours (FIG. 39).

Figure 40:
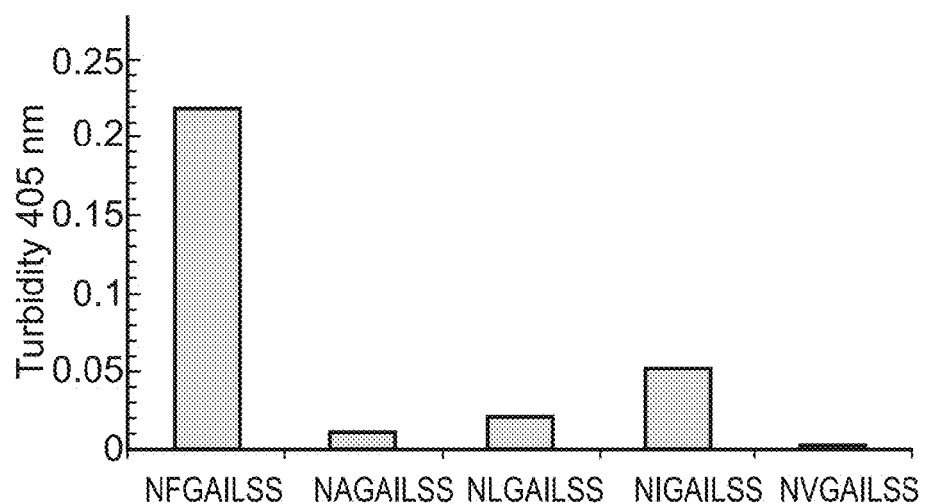
FIG. 40 is a histogram representation illustrating turbidity of IAPP analogues following seven day aging.

To determine whether the non-aggregative behavior of the hydrophobic analogues is a result of extremely slow kinetics, peptide analogue solutions were incubated for 1 week in the same experimental conditions and endpoint turbidity values were determined. As shown in FIG. 30, some low degree of turbidity was observed with the NIGAILSS, and lower extent for the NLGAILSS, NAGAILSS, and NVGAILSS peptides in decreasing order of turbidity. However, even for the NIGAILSS, the degree of turbidity was significantly lower as compared to the wild-type NFGAILSS protein (FIG. 40). Moreover, there was no correlation between aggregation potential and hydrophobicity or β-sheet forming tendency, since the lower degree of aggregation was observed with the substitution to the highly hydrophobic and β-sheet former, valine. The slight decrease in the endpoint turbidity value of the NFGAILSS wild-type peptide, as compared to the values obtained after 24 hours incubation, could reflect the formation of very large aggregates that adhere to the cuvette surface.

Example 38

Ultrastructural Analysis of Hydrophobically Modified hIAPP Peptide Fragments

Electron microscopy analysis was effected as described in Example 10.

Figure 41A:
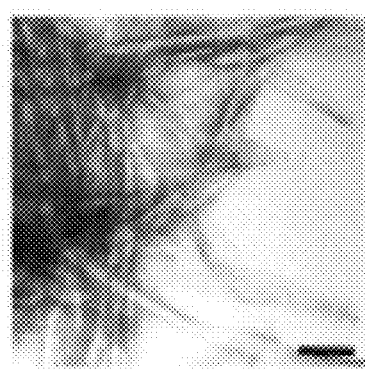
FIG. 41a-f are electron micrographs of "aged" IAPP analogues. NFGAILSS—FIG. 41a; NFGAILSS—FIG. 41b; NIGAILSS—FIG. 41c; NLGAILSS—FIG. 41d; NVGAILSS—FIG. 41e and NAGAILSS—FIG. 41f. The indicated scale bar represents 100 nm.
Figure 41B:
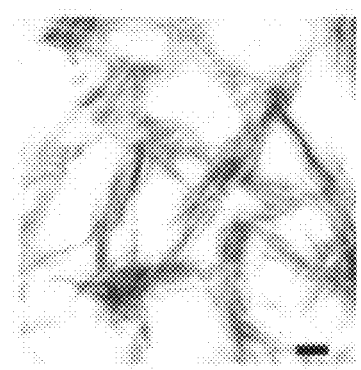
Figure 41C:
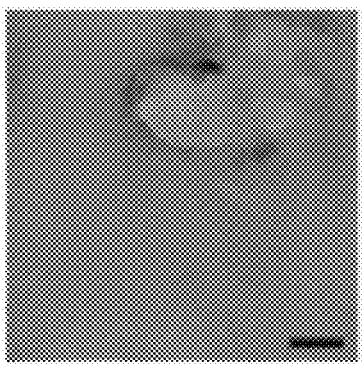
Figure 41D:
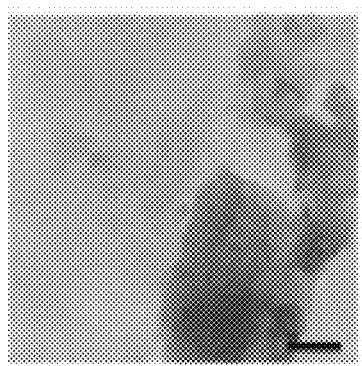
Figure 41E:
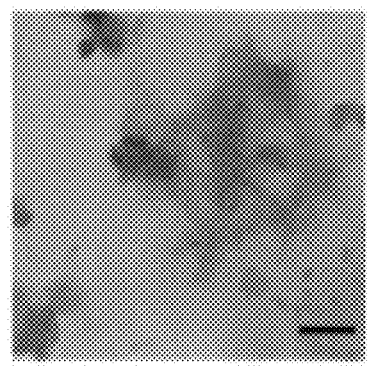
Figure 41F:
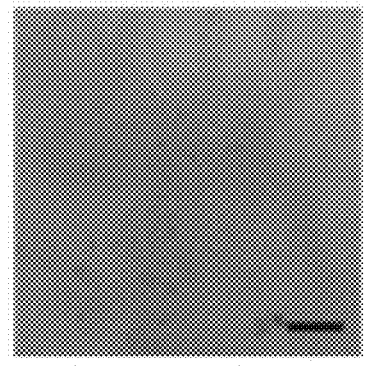

An ultrastructural visualization of any possible structures formed by the various analogous peptides was effected following five days of incubation. This structural analysis represents the most sensitive method since various aggregates were visualized individually. For that aim, the occurrence and characteristics of the formed structures were studied by electron microscopy using negative staining, with the same of peptide solution which were incubated in the aggregation assay (Example 32). As expected, well-ordered fibrils were observed with the wild-type peptide NFGAILSS peptide fragment (FIGS. 41a-b). Some amorphous aggregates could be also seen with the modified fragments (FIGS. 41c-f). However, those structures were significantly less abundant on the microscope grid. Larger aggregative structures were observed with the more hydrophobic substitutions as compared to the alanine analogues. Yet, unlike the ordered fibrillar structures that were seen with the NFGAILSS peptide, as mentioned above, these aggregates were quite rare and did not have ordered structures (FIGS. 41c-f). Those irregular and sporadic structures are consistent with some degree of non-specific aggregation as expected after long incubation of rather hydrophobic molecules.

Example 39

Determination of the Specific Function of Phenylalanine in the IAPP Self Assembly To determine the specific role of the phenylalanine residue in IAPP-self assembly, a membrane-based binding assay was preformed in order to systematically explore the molecular determinants that facilitate the ability of the full-length hIAPP to recognize the "basic amyloidogenic unit". To this end, the ability of MBP-IAPP (see Example 6) to interact with an array of peptides in which the phenylalanine position was systematically altered (SEQ ID NOs. 91-110), was addressed.

Materials and Experimental Procedures—see Examples 6-7.

Results

A peptide array corresponding to the SNNXGAILSS motif (SEQ ID NO: 90), where X is any natural amino-acid but cysteine was constructed. As shown in FIG. 42a, binding of MBP-IAPP was clearly observed to peptides which contained the aromatic tryptophan and phenylalanine residues at the X position (FIG. 42a). Interestingly, binding was also observed upon substitution of phenylalanine with basic amino acids such as arginine and lysine. In contrast, no binding was observed with any of the hydrophobic substitutions of the position, even after long exposure of the membrane (FIG. 42b).

The short exposure binding was assessed using densitometry (FIG. 42c). It will be appreciated though, that the measured binding should be interpreted as semiquantitative since the coupling efficiency during synthesis and therefore the amount of peptide per spot may vary. In this case, however, the marked difference in binding between the various peptide variants was very clear.

Taken together, all these observations substantiate the role of aromatic residues in the acceleration of amyloid formation processes.

Example 40

Design and Configuration of α-Aminoisobutyric Acid (Aib) Substituted Amyloid Forming Peptides The minimal amyloid forming region of IAPP polypeptide (i.e., IAPP 14-20, see Table 3 above) was selected as the target sequence for designing inhibitors which are able to bind thereto, block it and prevent aggregation thereof.

Experimental Approach

Figure 43A:
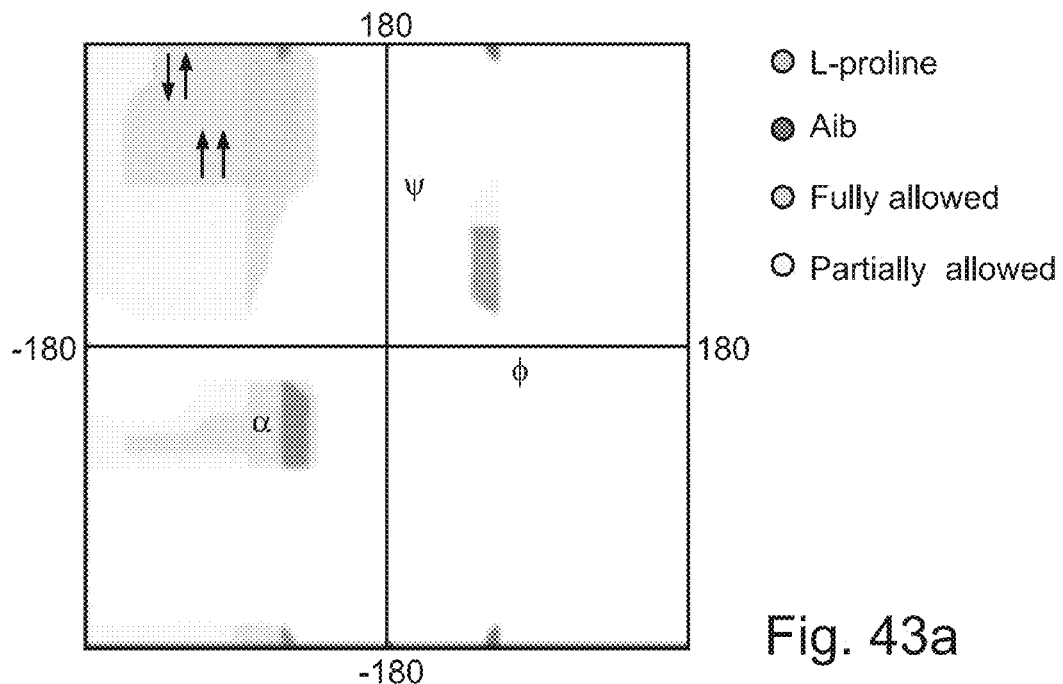
FIG. 43a is a Ramachandran plot showing the sterically allowed regions for all residues (yellow for fully allowed, orange for partially allowed), for L-Proline (blue) and for the achiral Aib residue (magenta).

To abolish the aggregation ability of amyloid forming peptides, β-sheet breakers are incorporated into the target sequence, such that the peptides cannot display a β-sheet conformation by which the monomers are stacked together to form fibrils. α-aminoisobutyric acid (Aib) is an unnatural amino acid which contains two methyl residues attached to C, of the carboxylic group. Unlike natural amino acids, this molecule does not have a hydrogen atom attached to the C. This affects widely the sterical properties of the amino acid especially with respect to the φ and ψ angels of the amide bond. While alanine has a wide range of allowed φ and ψ conformations, Aib, which is a α-methylated alanine has limited φ and ψ conformations. FIG. 43a shows the conformational map of Aib derived from the superposition of the Ramachandran plots of L-alanine and D-alanine. As is evident for FIG. 43a, the allowed angels are limited to small regions and the overall structure is much more suitable for an α-helix conformation rather than a β-strand conformation.

Hence, Aib can be used to prevent β-sheet conformation which is central to amyloid aggregation. Notably, a comparison between the Ramachandran plots of Aib and proline shows that Aib is a more potent β-sheet breaker than proline (FIG. 43a).

Figure 43B:
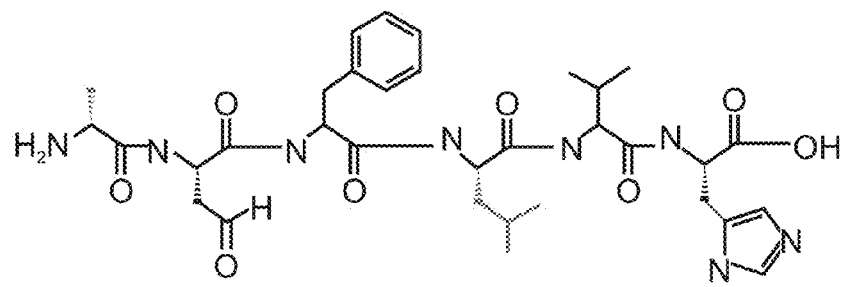
FIGS. 43b-c are schematic illustrations showing the chemical structure of the longer wild-type IAPP peptide (AN-FLVH, SEQ ID NO: 124, FIG. 43b) and the Aib modified structure thereof peptide (Aib-NF-Aib-VH, SEQ ID NO: 125, FIG. 43c). Functional groups suitable for modicifcation are marked in blue (FIG. 43b) while modified groups are marked in red (FIG. 43c).
Figure 43C:
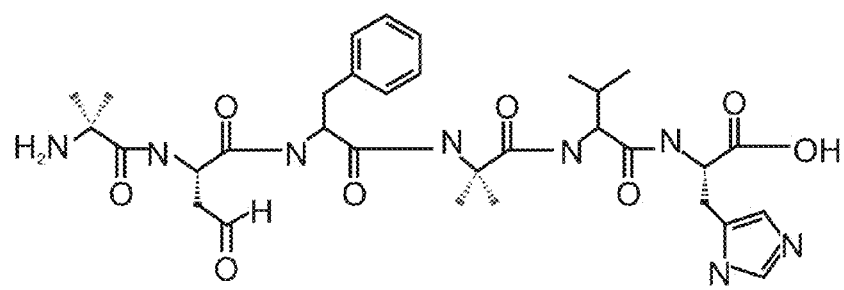

Two peptides including IAPP amyloid forming regions (i.e., ANFLVH and ANFLV, SEQ ID NOs: 124 and 126, respectively) were synthesized to include Aib substituting the alanine and the leucine residues. The newly synthesized peptides including the following amino acid sequences Aib-NF-Aib-VH (SEQ ID NO: 125) and Aib-NF-Aib-V (SEQ ID NO: 127), are illustrated in FIGS. 43b-c, respectively.

Peptides Synthesis—Peptides were synthesized by Peptron, Inc. (Taejeon, Korea) using solid-phase techniques. The correct identity of the peptides was confirmed by ion spray mass-spectrometry using a HP 1100 series LC/MSD. The purity of the peptides was confirmed by reverse phase high-pressure liquid chromatography (RP-HPLC) on a $C_{18}$ column, using a 30 minutes linear gradient of 0 to 100% acetonitrile in water and 0.1% trifluoroacetic acid (TFA) at flow rate of 1 ml/min.

Peptide Solutions—freshly prepared stock solutions were prepared by dissolving the lyophilized form of the peptides in dimethyl sulfoxide (DMSO) at a concentration of 100 mM. To avoid any pre-aggregation, fresh stock solutions were prepared for each experiment. Peptide stock solutions were diluted into microtubes as follows: 5 μL of peptides stock solutions added to 95 μL of 10 mM Tris, pH 7.2 (hence the final concentration of the peptide was 5 mM in the presence of 5% DMSO).

Example 41

Ultrastructural Analysis of Wild-Type and Aib Modified hIAPP Peptides

The fibrillogenic potential of the peptides described in Example 40 above, was assessed by electron microscopy analysis.

Materials and Experimental Procedures

Transmission Electron Microscopy—a 10 μL sample of 5 mM peptide solution in 10 mM Tris buffer, pH 7.2 aged for 4 days (for wt peptides) and for 10 days (for modified peptides) was placed on 400-mesh copper grids (SPI supplies, West Chester Pa.) covered by carbon-stabilized Formvar film. After 1 minute, excess fluid was removed, and the grid was then negatively stained with 2% uranyl acetate in water for another 2 minutes. Samples were viewed in a JEOL 1200EX electron microscope operating at 80 kV.

Results

Figure 44A:
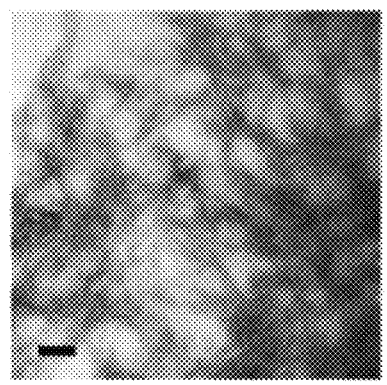
FIGS. 44a-d are electron micrographs of "aged" IAPP analogues.
Figure 44B:
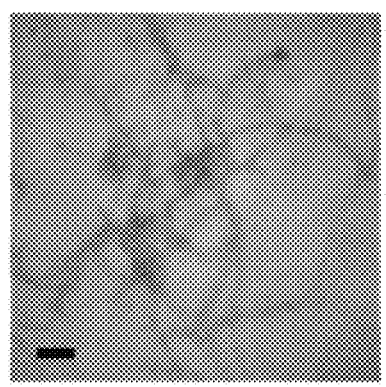
Figure 44C:
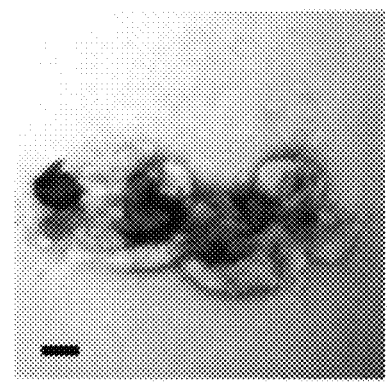
Figure 44D:
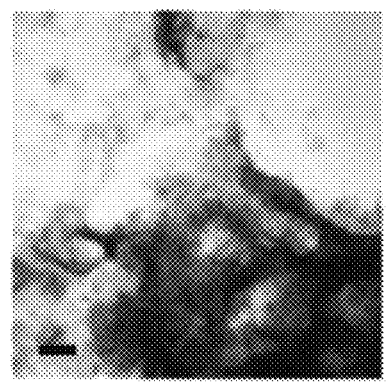

The ability of Aib containing peptides to form amyloid fibrils was examined in comparison to native IAPP peptides. Aged solutions of the Aib-modified and wild-type peptides were examined under electronic microscope (EM) using negative staining. As is shown in FIGS. 44a-b, both native peptides, ANFLVH (FIG. 44a) and ANFLV (FIG. 44a), formed fibrillar structures with high resemblense to the fibrils formed by the full-length IAPP protein. On the other hand, no fibrillar structures were evident for the Aib containing peptides, Aib-NF-Aib-VH (FIG. 44c) and Aib-NF-Aib-V (FIG. 44d), even after longer periods of incubation, while amorphous aggregates were still evident, suggesting that the Aib substituted peptides of the present invention are incapable of fibril formation.

Example 42

Examination of the Amyloidogenic Properties of Wild-Type and Aib Substituted IAPP Peptides by Congo Red Binding Assay Materials and Experimental Procedures Congo Red Staining and Birefringence—A 10 µL suspension of 5 mM peptide solution in 10 mM Tris buffer, pH 7.2 aged for 10 days was allowed to dry overnight on a glass microscope slide. Staining was performed by the addition of a 10 µL suspension of saturated Congo Red (CR) and NaCl in 80% ethanol (v/v) solution. The solution was filtered via 0.2 µm filter. The slide was then dried for a few hours. Birefringence was determined with a SZX-12 Stereoscope (Olympus, Hamburg, Germany) equipped with cross polarizers. 100× magnification is shown.

Results

Figure 45A:
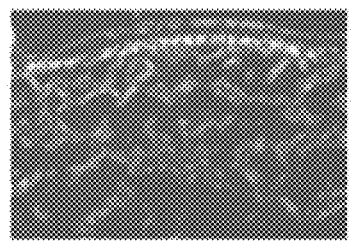
FIGS. 45a-d are photomicrographs illustrating Congo Red binding to pre-assembled wild type and Aib modified IAPP peptides. Polarized field micrographs are shown for each of the following aged (i.e., 11 days) peptide suspensions.
Figure 45B:
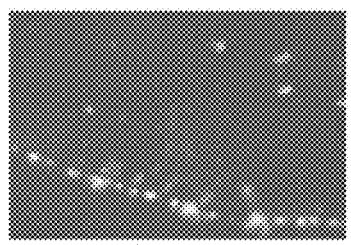
Figure 45C:
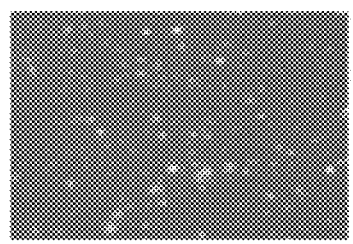
Figure 45D:
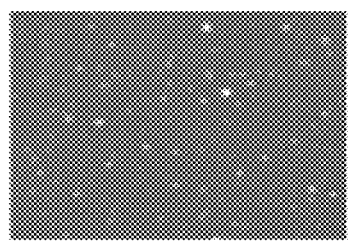

Congo red staining was used to assess the aamyloidogenic properties of Aib modified peptides. Slides were examined under the microscope using cross-polarizers. FIGS. 45a-b show a typical yellow-green birefringence for both ANFLVH and ANFLV peptides (FIG. 45a and b, respectively). However, in accordance with the EM studies, the Aib-modified peptides, Aib-NF-Aib-VH and Aib-NF-Aib-V, exhibited no birefringence suggesting that Aib modified peptides can not form amyloid fibrils (FIGS. 45c-d).

Example 43

Secondary Structure Analysis of Aib-Modified IAPP Peptide Fragments

Fourier transform infrared spectroscopy (FT-IR) was effected to determine the secondary structure of the Aib-modified hIAPP.

Materials and Experimental Procedures

Fourier Transform Infrared Spectroscopy—Infrared spectra were recorded using a Nicolet Nexus 470 FT-IR spectrometer with a DTGS detector. Samples of two week aged peptide solutions, were suspended on a $CaF_2$ plate and dried by vacuum. The peptide deposits were resuspended with $D_2O$ and subsequently dried to form thin films. The resuspension procedure was repeated twice to ensure maximal hydrogen to deuterium exchange. The measurements were taken using a 4 $cm^{-1}$ resolution and 2000 scans averaging. The transmittance minima values were determined by the OMNIC analysis program (Nicolet).

Results

Figure 46A:
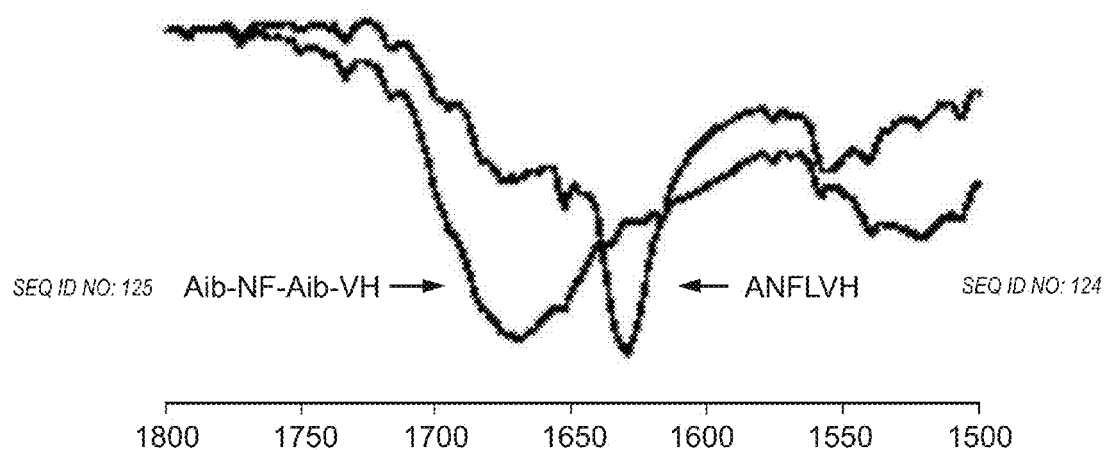
FIGS. 46a-b are graphs showing secondary structures in the insoluble wild type and Aib modified hIAPP aggregates as determined by Fourier transformed infrared spectroscopy (FT-IR).
Figure 46B:
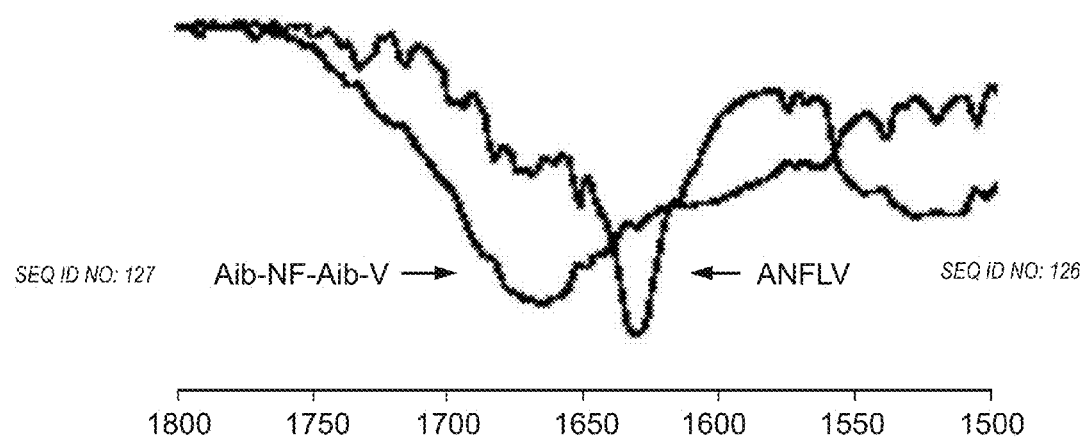

FT-IR spectroscopy was used to elucidate the internal conformation of the observed structures (see Examples 42 and 43, above). As shown in FIGS. 46a-b upon incorporation of Aib, IAPP peptides displayed a sharp change in the IR spectra. Whereas the ANFLVH and ANFLV peptides spectra were typical of β-sheet spectra, with minima at 1630 $cm^{-1}$ and 1632 $cm^{-1}$ respectively, the Aib-NF-Aib-VH and Aib-NF-Aib-V peptides displayed minima at 1670 $cm^{-1}$ and 1666 $cm^{-1}$, respectively, which are characteristic to a random coil conformation.

Taken together, these results suggest a fundamental difference between the native IAPP peptide and the Aib containing peptides. Whereas the native peptides are highly amiloidogenic, the modified Aib containing peptides are not able to form amyloid fibrils (Examples 41-43).

Example 44

Aib Modified Peptides Inhibit Amyloid Formation by IAPP Polypeptide

The degree of amyloid fibril formation with and without the Aib inhibitor was assessed using thioflavin T (ThT) as molecular indicator. The degree of fluorescence of the ThT dye is directly correlated with the amount of amyloid fibrils in the solution [LeVine H 3rd. (1993) Protein Sci. 2:404-410].

Materials and Experimental Procedures

Fourier Transform Infrared Spectroscopy—IAPP solutions (4 µM peptide in 10 mM Tris buffer pH 7.2), were incubated with or without 40 µM of the various peptide solutions at room temperature. Fibril formation was assessed by a ten fold dilution of the solutions into a solution which contained 3 µM thioflavin T (ThT) in 50 mM sodium phosphate pH 6.0 and determination of fluorescence at 480 nm with excitation at 450 nm using a Perkin Elmar LS50B spectroflurimeter. As a control a 10 mM Tris buffer pH 7.2 was diluted into the ThT solution and fluorescence was determined as described.

Results

Figure 47:
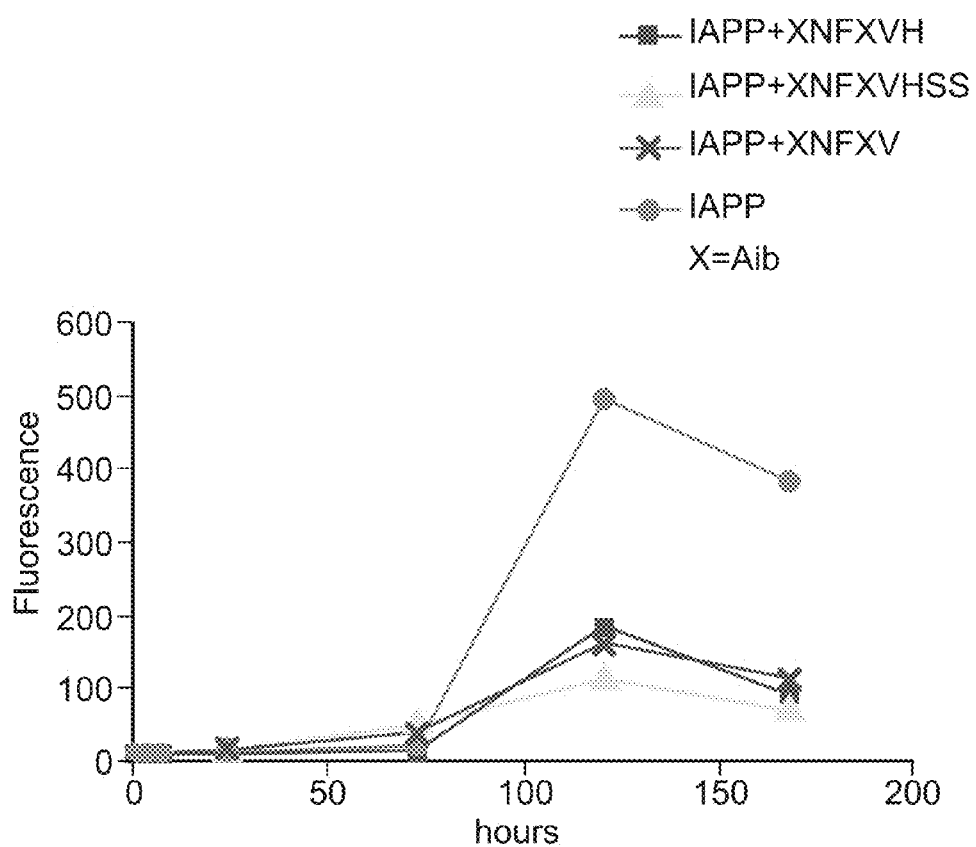
FIG. 47 is a graph showing the inhibitory effect of Aib modified peptides on amyloid fibril formation. Wild type IAPP was incubated alone or with the various peptides of the present invention. Fibril formation as a function of time was determined using ThT fluorescence.

As shown in FIG. 47, all Aib-modified peptides were able to inhibit the assembly of full-length IAPP polypeptide, suggesting that Aib modification of amyloid forming peptides can serve as strong inhibitory tool in various therapeutic applications.

Example 45

Di- and Tri-Aromatic Peptides can Inhibit Aggregation of IAPP Polypeptide

In order to study the ability of short aromatic amino acid sequences to inhibit the assembly of amyloid polypeptides and to address the ability of β-sheet breaker amino acids to facilitate such inhibition, an array of tetra-, tri- and dipeptides was synthesized and assayed.

Experimental Procedures

Peptide Synthesis—The list of peptides used in the present and Examples 46-47, which follow and designation thereof is presented in Table 7, below. Peptide synthesis is described in Examples 46-47, which follow.

TABLE 7

| Identification | Amino acid sequence | SEQ ID NO: |
|---|---|---|
| EG01 | D-Phe-D-Phe-D-Pro | 128 |
| EG02 | Aib-D-Phe-D-Asn-Aib | 129 |
| EG03 | D-Phe-D-Asn-D-Pro | 130 |
| EG04 | Aib-Asn-Phe-Aib | 131 |
| EG05 | Gln-Lys-Leu-Val-Phe-Phe | 132 |
| EG06 | Tyr-Tyr | 133 |
| EG07 | D-Phe-D-Phe-D-Pro | 112 |
| EG08 | Aib-D-Phe-D-Asn-Aib | 113 |
| EG09 | Aib-Asn-Phe-Aib | 114 |
| EG10 | Tyr-Tyr | 115 |

TABLE 7-continued

| Identification | Amino acid sequence | SEQ ID NO: |
|---|---|---|
| EG11 | Tyr-Tyr-NH2 | 116 |
| EG12 | Aib-Phe-Phe | 117 |
| EG13 | Asn-Tyr-Aib | 118 |
| EG14 | Asn-Tyr-Pro | 119 |
| EG15 β-aminoisobutyric acid (Aib) | D-Pro-D-Tyr-D-Asn | 120 |
| EG16 | D-Tyr-Aib | 121 |
| EG17 | D-Pro-D-Tyr | 122 |
| EG18 | D-Tyr-D-Pro | 123 |
| EG19 | Asn-Tyr-Tyr-Pro | 134 |
| EG20 | Tyr-Tyr-Aib | 135 |
| EG21 | Aib-Tyr-Tyr | 136 |
| EG22 | Aib-Tyr-Tyr-Aib | 137 |
| EG23 | D-Asn-Tyr-Tyr-D-Pro | 138 |
| EG24 | Pro-Tyr-Tyr | 139 |
| EG25 | Tyr-Tyr-Pro | 140 |
| EG26 | Pro-Tyr-Tyr-Pro | 141 |
| EG27 | D-Tyr-D-Tyr | 142 |
| EG28 | D-Pro-Aib | 143 |
| EG29 | D-Phe-D-Pro | 144 |
| EG30 | D-Trp-Aib | 145 |
| EG31 | D-Trp-D-Pro | 146 |
| d-F-P | D-Phe-Pro | 147 |
| P-d-F | Pro-D-Phe | 148 |

ThT Fluorescence Assay—See Example 44 Above.

Results

Figure 48:
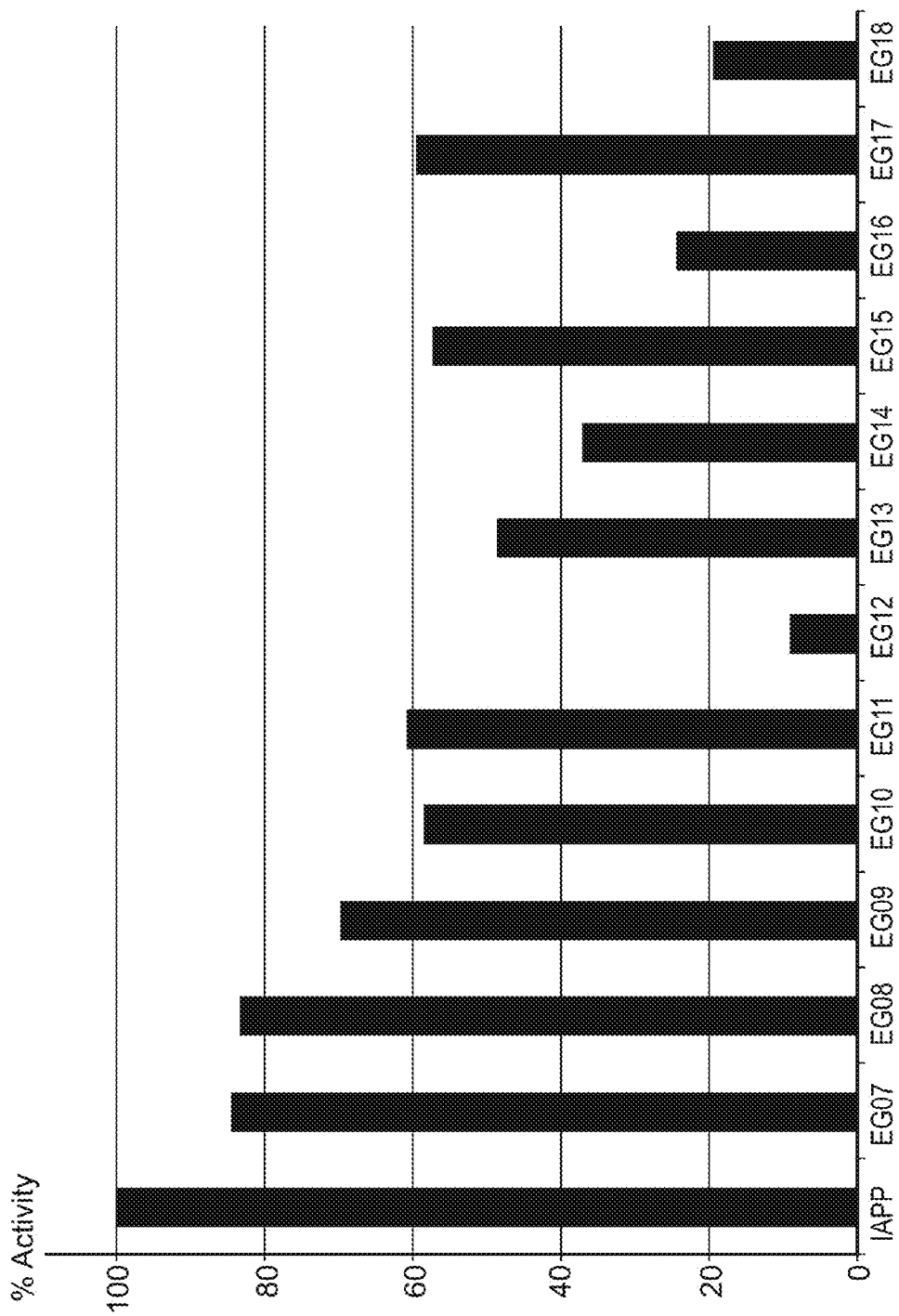
FIG. 48 is a histogram showing the inhibitory effect of short aromatic sequences (SEQ ID NOs. 112-123) on IAPP self-assembly.

The inhibitory peptides were assayed using standard ThT fluorescence assay (as described). FIG. 48 shows endpoint values after IAPP aggregation reaches a plateau, following 142 hours of incubation. The aggregation assay was preformed in the presence of IAPP polypeptide (4 µM) and the inhibitory peptides (40 µM).

As is clearly shown in FIG. 48, short aromatic amino acid sequences mediate recognition to IAPP polypeptide while inhibiting aggregation thereof. The best inhibitor was the Aib-Phe-Phe peptide (EG12) in which the Aib residue is conjugated to the shortest recognition element which can form amyloid-related structures [Reches and Gazit, Science (2003) 300(2619):625-7]. D-Tyr-D-Pro (EG18) and D-Tyr-D-Aib (EG16) displayed a significant inhibitory effect on IAPP aggregation substantiating the ability of a single aromatic residue to mediate molecular-recognition. Interestingly, Aib displayed a higher inhibitory activity than Proline. Furthermore, the significant difference in activity between peptide EG17 and EG18 which differ in the position of the β-sheet breaker amino acid relatively to the aromatic amino acid, suggests a role for the order and not only the composition of the peptides.

Example 46

Selection of Best Performing IAPP Fibrilization Inhibitors and Criteria for Selecting Same Peptides Synthesis—Peptide synthesis (excluding EG5, EG6, and EG7, D-Phe-Pro, and D-Pro-Phe), was effected by using solid-phase synthesis (Peptron, Inc., Taejeon, Korea). Peptide identity was confirmed by ion spray mass-spectrometry. Peptide purity was confirmed by reverse phase high-pressure liquid chromatography (RP-HPLC). EG5, EG6, and EG7, D-Phe-Pro, and D-Pro-Phe were purchased from Bachem (Bubendorf, Switzerland). Islet amyloid polypeptide (IAPP) was purchase from CalBiochem (La Jolla Calif., USA).

Thioflavin T Fluorescence Assay—hIAPP fibrillization was monitored by Thioflavin T dye binding assay. $hIAPP_{1-37}$ stock solution was diluted to a final concentration of 4 µM in 10 mM sodium acetate buffer (pH 6.5) with or without inhibitors (40 µM), and a final concentration of HFIP of 1% (vol). Immediately after dilution, sample was centrifuged for 20 minutes in 20,000×g at 4° C. and the supernatant fraction was used for fluorescence measurements. In every measurement Tht was added to a 1 ml sample at a final concentration of 3 µM and measurements were effected by using Perkin-Elmer (excitation 450 nm, 2.5 nm slit; emission 480 nm 10 nm slit). Background was subtracted from all samples.

Results

Identification of Potent Inhibitors and Rules for Inhibitor Design—In order to identify small peptide inhibitors of IAPP fibrillization and to optimize a minimal length of the inhibitors and maximal stability thereof, iterative cycles of peptide selection were effected using D-amino acids analogues.

Figure 49A:
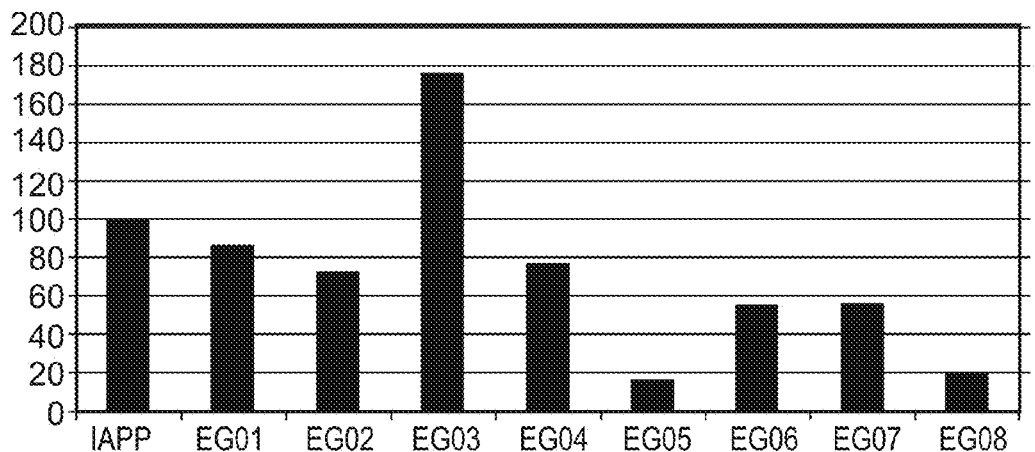
FIGS. 49a-d are graphs depicting iterative cycles of selection of IAPP fibrilization inhibitors. Fibrilization was monitored by ThT fluorescence assay. Fluorescence values of IAPP alone (4 µM) or in the presence of assayed compounds (40 µM) were tested. Measurements were taken once IAPP fluorescence reached a plateau. IAPP fluorescence was arbitrary set as 100.

The first round of selection shown in FIG. 49*a* demonstrated that peptides as short as tripeptides can efficiently inhibit the formation of amyloid by IAPP. Comparison of EG01 and EG03 suggests that presence of Asn residue within the short peptide does not contribute to the inhibition of amyloid formation and further supports the use of aromatic moieties along with beta-breakers for optimal inhibition. The effective inhibition of IAPP fibrillization by EGOS, a known inhibitor of amyloid formation [Tjernberg et al. (1996) J. Biol. Chem. 271: 8545-854], suggests a generic inhibition of amyloid formation by aromatic residues. Indeed, the similar activity of the EGOS and the much shorter EG08 (Aib conjugated to the Phe-Phe) element clearly suggest that the generic inhibition of EGOS stems from its aromatic nature.

Figure 49B:
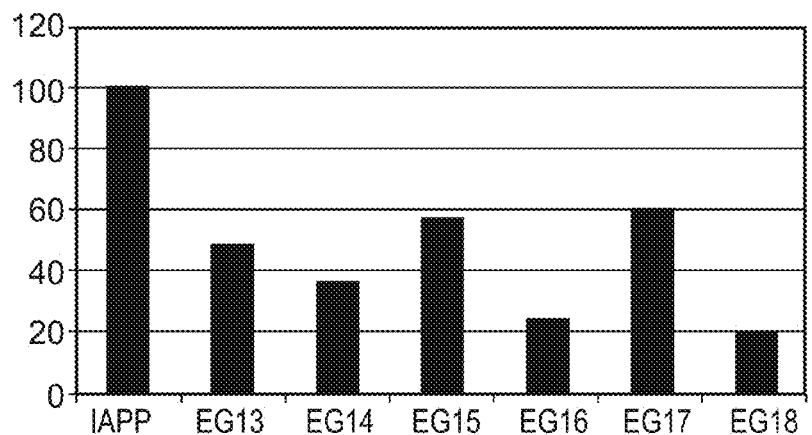
Figure 49C:
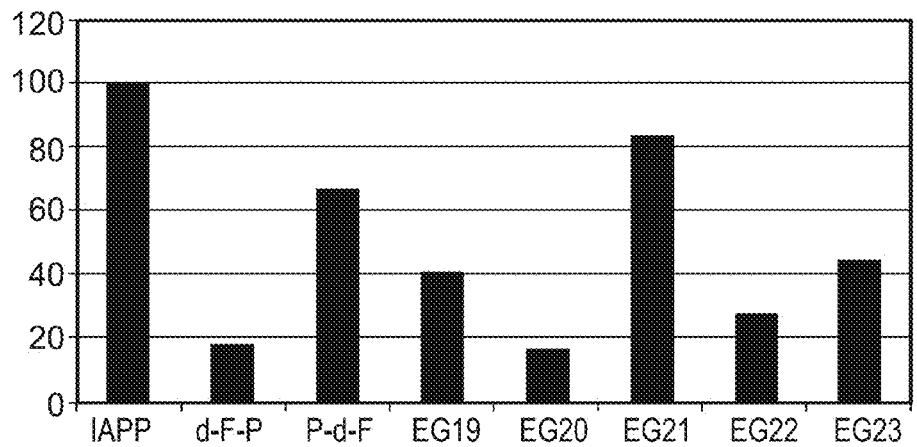
Figure 49D:
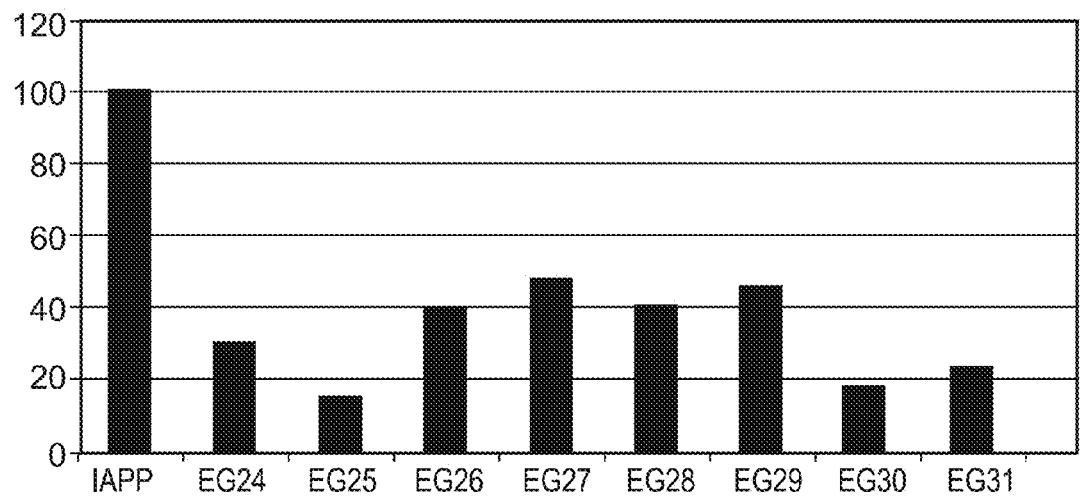

The second round of selection shown in FIG. 49*b* demonstrated that effective inhibition could be achieved not only by tripeptide but also by dipeptides (EG16, EG17, EG18). In all cases the conjugation of a D-isomer to an aromatic moiety was used. The difference between EG16 and EG17 was further studied in the next round to establish rules for the design of inhibitors. FIG. 49*c* shows the results of a third round of selection. The comparison in the third round (FIG. 49*c*) of EG20 vs. EG 21 (d-F-P vs. P-d-F) along with the results obtained by comparing EG16 and EG17 in the second round, and the results obtained by comparing EG24 and EG35 (in the forth round—FIG. 1*d*), suggest a general formula for the design of dipeptide inhibitors as set forth in: (Aromatic D or L)-(beta-breaker). These selection steps further provided a general formula for tripeptide inhibitors as set forth in: (Aromatic D or L)-(Aromatic D or L)-(beta-breaker).

The forth round also demonstrated the inhibition potential of four putuavely metabolically stable dipeptides EG28, EG29, EG30, EG31. Again, stressing the value of beta-breakers and aromatic amino acids for the inhibitory sequences.

Example 47

Inhibition of β-Amyloid Polypeptide Fibril Formation by D-Trp-Aib

Peptides Synthesis—See Example 46 above. Recombinant β-amyloid (Aβ 1-40, >98% pure) was purchase from rPeptide (Athens Ga., USA).

Thioflavin T Fluorescence Assay—Fibrillization of Aβ 1-40 was monitored by Thioflavin T dye binding assay. Aβ 1-40 stock solution was diluted to a final concentration of 5 μM in 100 mM NaCl, 10 mM sodium phosphate buffer (pH 7.4) with or without inhibitors. In every measurement Tht was added to 0.1 ml sample to a final concentration of 0.3 μM ThT and 0.4 μM polypeptide. Measurements were effected using Jobin Yvon FluoroMax-3 (excitation 450 nm, 2.5 nm slit; emission 480 nm 5 nm slit, integration time 1 second). Background was subtracted from all samples.

Transmission Electron Microscopy—10 μL samples were placed on 400-mesh copper grids (SPI supplies, West Chester Pa.) covered with carbon-stabilized Formvar film. Following 1 minute, excess fluid was removed, and the grids were negatively stained with 2% uranyl acetate in water for another two minutes. Samples were viewed by a JEOL 1200EX electron microscope operating at 80 kV.

Results

Figure 50:
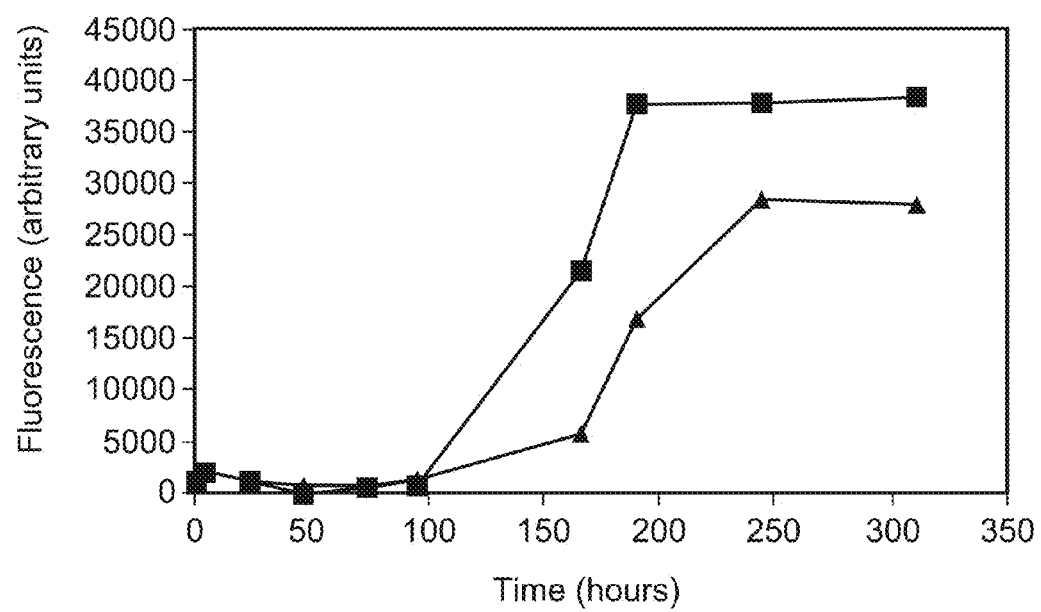
FIG. 50 is a graph depicting Inhibition of Aβ (1-40) fibril formation by D-Trp-Aib. Aβ 1-40 stock solution was diluted to a final concentration of 5 µM in 100 mM NaCl, 10 mM sodium phosphate buffer (pH 7.4) with 10 µM D-Trp-Aib (triangles) or without any addition (squares). Fluorescence values were measured after addition of 0.3 µM Tht to each sample. The results represent the mean of two independent measurements.

Fluorescence Measurements of Inhibition—To test whether the D-Trp-Aib can inhibit amyloid formation by molecules other than IAPP, Alzheimer's β-amyloid 1-40 (Aβ) was served as a model system. As shown in FIG. 50, in the absence of inhibitor, Aβ displayed a lag phase in fibrilization of about 100 hours which was followed by a fast enhancement in fluorescent levels. In the presence of 10 μM of EG30, the lag time was significantly increased and the overall fluorescence upon reaching a plateau was significantly lower than that observed without the inhibitor. This further suggests that aromatic inhibitors may serve as generic amyloid inhibitors and a common mechanism of assembly [Gazit (2002) FASEB J. 16, 77-83].

Figure 51A:
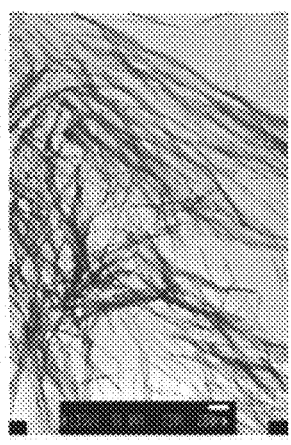
FIGS. 51a-c are photomicrographs depicting the inhibitory effect of D-Trp-Aib on the fibrilization of Aβ as visualized by TEM.
Figure 51B:
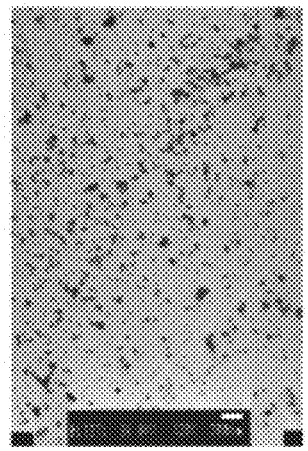
Figure 51C:

Ultrastructural Analysis—To get information on the mechanism of inhibition, samples taken from the fluorsence assay upon its termination assay were viewed by electron microscopy (FIG. 51*a-c*). Distinct and well-defined amyloid fibers were present in samples of Aβ not including the inhibitor (FIG. 51*a*). In contrast, in the presence of EG30, Aβ was detected mostly as amorphous aggregates (FIG. 51*b*) or as fragmented fibrils (FIG. 51*c*). This suggests that even those fibrils generated in the presence of the inhibitor were short and probably dysfunctional.

Thus, the D-Trp-Aib compound offers a unique combination of pharmaceutical properties in an extremely small molecule:

1. Hetero-aromatic interactions: The interaction between the tryptophan indole and the aromatic recognition interfaces of the growing amyloid fibrils (Gazit, 2002) allows specific and oriented binding that directly and precisely blocks further homo-molecular self-assembly of the growing chain.

2. The Aib conformational restriction: The conjugation of the O-aminoisobutyric acid (Aib), an amino acid with exceptional geometrical constrain, induce a very strong β-sheet breakage effect, a key measure to halt the growing of amyloid fibrils. This β-breakage strategy shows clear a advantage as compared to prior art (proline introduction) in terms of size and complexity of the molecule.

3. A stable D-isomer conformation: The inhibitor is built of a D-amino acid and a non-chiral Aib moiety. This results in the formation of a non-cleavable peptide bond and thus with a presumably high physiological stability.

4. Peptide bond stacking: In spite of its small size, a typical peptide bond (although isomerically stable one) is retained within the molecule. The unique planar characteristic of such a peptide bond allows a specific and geometrically-constrained stacking of the molecule on the growing amyloid chain, due to their partially planar resonating structures with the exact gemetry that is consistant with β-strand interaction.

5. Electrostatic repulsion: The existence of charged terimi results in electrostatic repulsion of further binding monomers. Such repulsion is achieved by introduction of a charge aspartic acid in other peptide inhibitors [Soto et al. (2003) J. Biol. Chem. 278:13905] as there is a need to block the termini of these peptides to decrease proteolyic degradation. The non-native stable isomeric configuration of the D-Trp-Aib allows the retention of charged termini within the minimal framework resulting in a significantly small molecule.

6. Bulky hydrophobic moiety: The trypotophan indole group offers a unique bulkiness and hydrophobic nature in a very small molecular system. It is well established that tryptophan moieties have among the highest membrane partition coefficients. It is speculated that this property should have a key advantage for oral bioavailability and blood brain barrier (BBB) transfer.

7. Antioxidant activity: The indole group is also known to act as antioxidant by the scavenging of free-radicals. Indeed some of the drug candidates for treating AD are based on this property (e.g. indole-3-propionic acid of MindSet). However, while such molecules are effective in the protection of neural cells from AD related oxidation stress, they lack the unique fibrillization inhibitory properties of the D-Trp-Aib molecular frame.

8. Small size: D-Trp-Aib is a remarkably small active molecule. All the unique properties that were described in the previous paragraphs (1-7) are maintained within a molecule of less than 300 Da. The small size of this non-cleavable molecule suggests an oral bioavailability, long half-life, and transfer of the BBB, while maintaining low immunogenic potential.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A method of treating an amyloid-associated disease in an individual in need thereof, the method comprising systemically administering to the individual a therapeutically effective amount of a synthetic dipeptide having the general Formula:

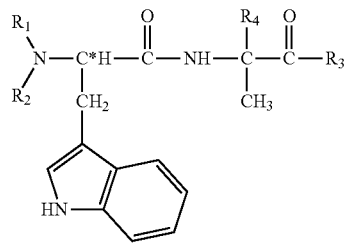

wherein:

C* is a chiral carbon having a D configuration;

$R_1$ and $R_2$ are each independently selected from the group consisting of hydrogen, alkyl, cycloalkyl, aryl, carboxy, C-thiocarb;

$R_3$ is selected from the group consisting of hydroxy, alkoxy, aryloxy, thiohydroxy, thioalkoxy, thioaryloxy, halo and amine; and $R_4$ is alkyl, thereby treating the amyloid-associated disease in the individual.

2. The method of claim 1, wherein the amyloid-associated disease is Alzheimer's disease.

3. The method of claim 1 wherein said systemically administering comprises parenteral administration.

4. The method of claim 1, wherein said systemically administering is by oral administration, rectal administration, transmucosal administration, transnasal administration, intramuscular administration, subcutaneous administration, intramedullar injection, intrathecal administration, direct intraventricular administration, intravenous administration, intraperitoneal administration and intranasal injection.

5. The method of claim 1, wherein $R_4$ is methyl or alkyl substituted by halo.

6. The method of claim 5, wherein $R_1$ and $R_2$ are each hydrogen and $R_3$ is hydroxy.

7. The method of claim 1, wherein said dipeptide is as set forth in SEQ ID NO: 145.

\* \* \* \* \*